United States Patent [19]
Spaete et al.

[11] Patent Number: 5,925,751
[45] Date of Patent: Jul. 20, 1999

[54] HUMAN CYTOMEGALOVIRUS DNA SEQUENCES

[75] Inventors: Richard Spaete, Belmont; Tai-An Cha, San Ramon, both of Calif.

[73] Assignee: Aviron, Mountain View, Calif.

[21] Appl. No.: 08/926,922

[22] Filed: Sep. 10, 1997

Related U.S. Application Data

[62] Division of application No. 08/414,926, Mar. 31, 1995, Pat. No. 5,721,354.

[51] Int. Cl.⁶ ........................ C07H 21/04; A61K 39/245; C12Q 1/70; C12N 15/00
[52] U.S. Cl. ................................... 536/23.72; 424/230.1; 424/30.1; 435/5; 435/172.3; 435/252.3; 435/320.1; 435/69.1
[58] Field of Search ................................ 536/23.1, 23.72; 435/320.1, 252.3, 69.1, 172.3, 5; 424/230.1, 30.1

[56] References Cited

U.S. PATENT DOCUMENTS 5,075,213  12/1991  Pande et al. ................................. 435/5
5,194,256  3/1993  Rasmussen et al. ...................... 424/89

OTHER PUBLICATIONS

Chou et al., Analysis of Interstrain Variation in Cytomegalovirus Glycoprotein B Sequences Encoding Neutraliztion–Related Epitopes, The Journal of Infectious Diseases, vol. 163, pp. 1229–1234, especially p. 1229, col. 2, second full paragraph, Jun. 1991.
Zaia et al., Comparative Analysis of Human Cytomegalovirus alpha–Sequence in Multiple Clinical Isolates by Using Polymerase Chain Reaction and Restriction Fragment Length Polymorphism Assays, Journal of Clinical Microbiology, vol. 28, No. 12, pp. 2602–2 Dec. 1990.
Pande et al., Human Cytomegalovirus Strain Towne pp65 Gene: Nucleotide Sequence and Expression in Escherichia coli, Virology, vol. 182, pp. 220–228, see Abstract, Jan. 1991.
Pande et al., Human Cytomegalovirus Strain Towne pp28 Gene: Sequence Comparison to pp28 of HCMV AD169 and Stable Expression in Chinese Hamster Ovary Cells, Virology, vol. 184, pp. 762–767, see Abtract and Fig. 3, Jul. 1991.
Zaia, Comparative Analysis of Human Cytomegalivirus a–Sequence in Multiple Clinical Isolates etc., J Clin. Microbio. 28 (1990) 2602–07.
Pande, Human Cytomegalovirus Strain Towne pp65 Gene: Nucleotide Sequence and Expression in Escherichia coli, Virology 182 (1991) 220–28.
Pande, Human Cytomegalovirus Strain pp28 Gene: Comparison to pp28 of HCMV AD169 etc, Virology 194 (1991) 762–67.
Chou, Analysis of Interstrain Variation in Cytomegalovirus Glycoprotein B etc, J Inf Diseases 163 (1991) 1229–34.
Robson, Primate Cytomegalovirus Assembly Protein: Genome Location and Nucleotide Sequence, J Virol 63 (1989) 669–76.
Lehner, Comparative Sequence Analysis of Human Cytomegalovirus Strains, J Clin Microbiol 29 (1991) 2494–2502.
Fries, Frequency Distribution of Cytomegalovirus Envelop Glycoprotein Geneotypes etc, J Inf Diseases 169 (1994) 478–83.

(List continued on next page.)

*Primary Examiner*—Jeffrey Stucker
*Assistant Examiner*—Hankyel T. Park
*Attorney, Agent, or Firm*—Luann Cserr; Tracy Dunn

[57] ABSTRACT

Provided are novel Toledo and Towne human cytomegalovirus DNA sequences (HCMV) and proteins encoded thereby. The sequences are useful in methods and compositions for detecting HCMV infections and in immunogenic compositions for preventing HCMV infections.

5 Claims, 53 Drawing Sheets

OTHER PUBLICATIONS

Quinnan, Comparative Virulence and Immunogenicityt of the Towne Strain etc, Annals of Int Med 101 (1984) 478–83.

Plotkin, Lancet 1 (1984) 528–30.

Plotkin, Protective Effects of Towne Cytomegalovirus Vaccine etc, J Inf Disease 159 (1989) 860–65.

Huang, Detection of Human Cytomegalovirus and Analysis of Strain Variation, Yale J Biol and Med 49 (9176) 29–43.

Kilpatrick, Analysis of Cytomegalovirus Genomes with Restriction Endonucleases etc, J virol 18 (1976) 1095–1105.

LaFemina, Structural Organization of the DNA Molecules from Human Cytomegalovirus, in "Animal Virus Genetics", Field, BN and R Joenish, eds., Academic Press, NY 1980, pp. 39–53.

Chandler, Comparison of Restriction Site Polymorphisms Among Clinical Isolates and Laboratory Strains of Hukman Cytomegalovirus, J Gen Virol 67 (1986) 2179–92.

Spaete, Human Cytomegalovirus Strain Towne Glycoprotein B etc, Virology 167 (1988) 207–25.

Marsh Cytomegalovirus Vaccines, in "The Human Herpesvirus," RJ Whitley, B Roizman and C Lopez, eds., Raven Press, NY, pp. 381–395, (1993).

Alford, Cytomegalovirus, in "The Human Herpesviruses," RJ Whitley, B Roizman and C Lopez, eds. Raven Press, NY, pp. 227–255, (1993).

Chou, Differentiation of Cyutomegalovirus Strains by Restriction Analysis etc, J Inf Diseases 162 (1990) 738–42.

Pritchett, DNA Nucleotide Sequence Heterogeneity Between the Towne and AD 169 Strains of Cytomegalovirus, J Virol 36 (1980) 152–61.

```
         10         20         30         40         50    UL133  60
CGCTGTAGGG ATAAATAGTG CGATGGCGTT TGTGGGAGAA CGCAGTAGCG ATGGGTTGCG
GCGACATCCC TATTTATCAC GCTACCGCAA ACACCCTCTT GCGTCATCGC TACCCAACGC 70         80         90        100        110        120
ACGTGCACGA TCCTTCGTGG CAATGCCAAT GGGGCGTTCC CACGGATTATC GTGGCCTGGA
TGCACGTGCT AGGAAGCACC GTTACGGTTA CCCCGCAAGG GTGCTAATAG CACCGGACCT 130        140        150        160        170        180
TAACATGCGC GGCTTTAGGA ATTTGGTGTT TGGCGGGATC GTCGGCGGAT GTCTCTTCGG
ATTGTACGCG CCGAAATCCT TAAACCACAA ACCGCCCTAG CAGCCGCCTA CAGAGAAGCC 190        200        210        220        230        240
GACCCGGCAT CGCAGCCGTA GTCGGCTGTT CTGTTTTCAT GATTTTCCTC TGCGCGTATC
CTGGGCCGTA GCGTCGGCAT CAGCCGACAA GACAAAAGTA CTAAAAGGAG ACGCGCATAG 250        260        270        280        290        300
TCATCCGTTA CCGGGAATTC TTCAAAGACT CCGTAATCGA CCTCCTTACC TGCCGATGGG
AGTAGGCAAT GGCCCTTAAG AAGTTTCTGA GGCATTAGCT GGAGGAATGG ACGGCTACCC 310        320        330        340        350        360
TTCGCTACTG CAGCTGCAGC TGTAAGTGCA GCTGCAAATG CATCTCGGGC CCCTGTAGCC
AAGCGATGAC GTCGACGTCG ACATTCACGT CGACGTTTAC GTAGAGCCCG GGGACATCGG 370        380        390        400        410        420
GCTGCTGTTC AGCGTGTTAC AAGGAGACGA TGATTTACGA CATGGTCCAA TACGGTCATC
CGACGACAAG TCGCACAATG TTCCTCTGCT ACTAAATGCT GTACCAGGTT ATGCCAGTAG 430        440        450        460        470        480
GACGGCGTCC CGGACACGGC GACGATCCCG ACAGGGTGAT CTGCGAGATA GTCGAGAGTC
CTGCCGCAGG GCCTGTGCCG CTGCTAGGGC TGTCCCACTA GACGCTCTAT CAGCTCTCAG
```

```
         490        500        510        520        530        540
   CCCCGGTTTC GGCGCCGACG GTGTCCGTCC CCCCGCCGTC GGAGGAGTCC CACCAGCCCG
   GGGGCCAAAG CCGCGGCTGC CACAGGCAGG GGGGCGGCAG CCTCCTCAGG GTGGTCGGGC

UL134
         550        560        570        580        590        600
   ┌TCATCCCACC GCAGCCGCCA GCACCGACAT CGGAACCCAA ACCGAAGAAA GGTAGGGCGA
    AGTAGGGTGG CGTCGGCGGT CGTGGCTGTA GCCTTGGGTT TGGCTTCTTT CCATCCCGCT
    ↓

610        620        630        640        650        660
   AAGATAAACC GAAGGGTAGA CCGAAAGACA AACCTCCGTG CGAACCGACG GTGAGTTCAC
   TTCTATTTGG CTTCCCATCT GGCTTTCTGT TTGGAGGCAC GCTTGGCTGC CACTCAAGTG 670        680        690        700        710        720
   AACCACCGTC GCAGCCGACG GCAATGCCCG GCGGTCCGCC CGACGCGCCT CCCCCGCCA
   TTGGTGGCAG CGTCGGCTGC CGTTACGGGC CGCCAGGCGG GCTGCGCGGA GGGGGCGGGT 730        740        750        760        770        780
   TGCCGCAGAT GCCACCCGGC CGGTACGAGG CGGTACAAGC TGCCGTGCAG GCGGCCGTGG
   ACGGCGTCTA CGGTGGGCCG GCCATGTTCC GCCATGTTCG ACGGCACGTC CGCCGGCACC

UL133
         790        800        810    820 ↑ 830        840
   CCGCGGCTCT ACAACAACAG CAGCAGCATC AGACCGGAAC┌GTAA CCCGCC CCCGGTGCGA
   GGCGCCGAGA TGTTGTTGTC GTCGTCGTAG TCTGGCCTTG CATT GGGCGG GGGCCACGCT 850        860        870        880        890        900
  ┌TAAGGAATTT TCCGACTTGG CGCACATCTC CTTCCTCAAT GTTTGGACAA TAAACACATT
   ATTCCTTAAA AGGCTGAACC GCGTGTAGAG GAAGGAGTTA CAAACCTGTT ATTTGTGTAA

UL135
         910        920        930     940 ↑    950        960
   CCTTGCCAAA AAATGACGTT TCCAGAAATC CAAGGCATAA ┌ATGTCCGTAC ACCGGCCCTT
   GGAACGGTTT TTTACTGCAA AGGTCTTTAG GTTCCGTATT  TACAGGCATG TGGCCGGGAA
```

```
      970        980        990       1000       1010       1020
CCCAACACGG AGTTTGAGAT TCCAAGCAGG AGAGAAGATC ATGGTGTGGA TATGGCTCGG
GGGTTGTGCC TCAAACTCTA AGGTTCGTCC TCTCTTCTAG TACCACACCT ATACCGAGCC 1030       1040       1050       1060       1070       1080
CATCGGGCTC CTCGGCGGTA CCGGACTGGC TTCCCTGGTC CTGGCCATTT CCTTATTTAC
GTAGCCCGAG GAGCCGCCAT GGCCTGACCG AAGGGACCAG GACCGGTAAA GGAATAAATG
                                              ▼UL134

1090       1100       1110       1120       1130       1140
CCAGCGCCGA GGCCGCAAGC GATCCGACGA GACTTCGTCG CGAGGCCGGC TCCCGGGTGC
GGTCGCGGCT CCGGCGTTCG CTAGGCTGCT CTGAAGCAGC GCTCCGGCCG AGGGCCCACG 1150       1160       1170       1180       1190       1200
TGCTTCTGAT AAGCGTGGTG CCTGCGCGTG CTGCTATCGA AATCCGAAAG AAGACGTCGT
ACGAAGACTA TTCGCACCAC GGACGCGCAC GACGATAGCT TTAGGCTTTC TTCTGCAGCA 1210       1220       1230       1240       1250       1260
CGAGCCGCTG GATCTGGAAC TGGGGCTCAT GCGGGTGGAC ACCCACCCGC CGACGCCGCA
GCTCGGCGAC CTAGACCTTG ACCCCGAGTA CGCCCACCTG TGGGTGGGCG GCTGCGGCGT 1270       1280       1290       1300       1310       1320
GGTGCCGCGG TGTACGTCGC TCTACATAGG AGAGGATGGT CTGCCGATAG ATAAACCCGA
CCACGGCGCC ACATGCAGCG AGATGTATCC TCTCCTACCA GACGGCTATC TATTTGGGCT 1330       1340       1350       1360       1370       1380
GCGCGGTTCG AGATCCCCGA CGTATCCACG CCGGGAACGC CGACCAGCAT CGGGAAGCAT
CGCGCCAAGC TCTAGGGGCT GCATAGGTGC GGCCCTTGCG GCTGGTCGTA GCCCTTCGTA 1390       1400       1410       1420       1430       1440
GTTTCCTCCG CCGTCGCATT GCTCCTCGTC TCGTCCTCGA CCAGGTCGA CCAGGTCGA
CAAAGGAGGC GGCAGCGTAA CGAGGAGCAG AGCAGGAGCT GGTCGCAGCT GGTCGCAGCT
```

```
1450       1460       1470       1480       1490       1500
CACGGTGCTG TATCAGCCGC CGCCATCCTG GAAGCCACCT CCGCCGCCCG GGCGCAAGAA
GTGCCACGAC ATAGTCGGCG GCGGTAGGAC CTTCGGTGGA GGCGGCGGGC CCGCGTTCTT 1510       1520       1530       1540       1550       1560
GCGGCCGCCT ACGCCCGCCGG TCCGGGCCCC CACCACGCGG CTGTCGTGCG ACAGACCCCC
CGCCGGCGGA TGCGGGCGGCC AGGCCCGGGG GTGGTGCGCC GACAGCAGCG TGTCTGGGGG 1570       1580       1590       1600       1610       1620
GACGCCGATA CCCGCGCCGC GTAAGAACCT GAGCACGCCG CCCACCAAGA AAACGCCGCC
CTGCGGCTAT GGGCGCGGCG CATTCTTGGA CTCGTGCGGC GGGTGGTTCT TTTGCGGCGG 1630       1640       1650       1660       1670       1680
GCCCACGAAA CCCAAGCCGG TCGGCTGGAC ACCGCCGGTG ACACCCAGGC CCTTCCCGAA
CGGGTGCTTT GGGTTCGGCC AGCCGACCTG TGGCGGCCAC TGTGGGTCCG GGAAGGGCTT 1690       1700       1710       1720       1730       1740
AACGCCGACG CCACAAAAGC CGCCGCGGAA TCCGAGACTA CCGGCACCCG TCGGTCTGGA
TTGCGGCTGC GGTGTTTTCG GCGGCGCCTT AGGCTCTGAT GGCCGTGGGC AGCCAGACCT 1750       1760       1770       1780       1790       1800
GAATCTCTCG AAGGTGGGAC TCTCGTGTCC CTGTCCCCGA CCCCGCACGC CGACGGAGCC
CTTAGAGAGC TTCCACCCTG AGAGCACAGG GACAGGGGCT GGGGCGTGCG GCTGCCTCGG 1810       1820       1830       1840       1850       1860
GACCACGCTG CCTATCGTGT CGGTTTCCGA GCTAGCCCCG CCTCCTCGAT GGTCGGACAT
CTGGTGCGAC GGATAGCACA GCCAAAGGCT CGATCGGGGC GGAGGAGCTA CCAGCCTGTA
```

```
        1870       1880       1890       1900       1910       1920
  CGAGGAACTC TTGGAACAGG CGGTGCAGAG CGTCATGAAG GACGCCGAGT CGATGCAGAT
  GCTCCTTGAG AACCTTGTCC GCCACGTCTC GCAGTACTTC CTGCGGCTCA GCTACGTCTA

UL135 1930     1940       1950       1960       1970       1980
  GACCTGAGAC CGAAAGAGCG AGCGGCGTCCG TTGTACAGTT GTATAGCAGC ACACGCCTTC
  CTGGACTCTG GCTTTCTCGC TCGCGCAGGC AACATGTCAA CATATCGTCG TGTGCGGAAG 1990       2000       2010  2020 UL136  2030       2040
  CCTCTTTTTC ACCGCAGCTA AGAGAGAGAA AGAGAGTATG TCAGTCAAGG GCGTGGAGAT
  GGAGAAAAAG TGGCGTCGAT TCTCTCTCTT TCTCTCATAC AGTCAGTTCC CGCACCTCTA 2050       2060       2070       2080       2090       2100
  GCCAGAAATG ACGTGGGACT TGGACGTTAG AAATAAATGG CGGCGTCGAA AGGCCCTGAG
  CGGTCTTTAC TGCACCCTGA ACCTGCAATC TTTATTTACC GCCGCAGCTT TCCGGGACTC 2110       2120       2130       2140       2150       2160
  TCGCATTCAC CGGTTCTGGG AATGTCGGCT ACGGGTGTGG TGGCTGAGTG ACGCCGGCGT
  AGCGTAAGTG GCCAAGACCC TTACAGCCGA TGCCCACACC ACCGACTCAC TGCGGCCGCA 2170       2180       2190       2200       2210       2220
  AAGAGAAACC GACCCACCGC GTCCCCGACG CCGCCCGACT TGGATGACCG CGGTGTTTCA
  TTCTCTTTGG CTGGGTGGCG CAGGGGCTGC GGCGGGCTGA ACCTACTGGC GCCACAAAGT 2230       2240       2250       2260       2270       2280
  CGTTATCTGT GCCGTTTTGC TTACGCTTAT GATTATGGCC ATCGGCGCGC TCATCGCGTA
  GCAATAGACA CGGCAAAACG AATGCGAATA CTAATACCGG TAGCCGCGCG AGTAGCGCAT 2290       2300       2310       2320       2330       2340
  CTTAAGATAT TACCACCAGG ACAGTTGGCG AGACATGCTC CACGATCTAT TTTGCGGCTG
  GAATTCTATA ATGGTGGTCC TGTCAACCGC TCTGTACGAG GTGCTAGATA AAACGCCGAC
```

*FIG._1C-1*

|  | 2350 | 2360 | 2370 | 2380 | 2390 | 2400 |
|---|---|---|---|---|---|---|
|  | TCATTATCCC | GGATGTGCCC | GTCGGCACCA | CGAGCGGCAG | AGAAGGAGAC | GGCAAGCCAT |
|  | AGTAATAGGG | CTCTTCACGG | CAGCCGTGGT | GCTCGCCGTC | TCTTCCTCTG | CCGTTCGGTA |

|  | 2410 | 2420 | 2430 | 2440 | 2450 | 2460 |
|---|---|---|---|---|---|---|
|  | GGATGTGCCC | GACCCCGAAC | TCGGCGACCC | GGCCCGCCGG | CCGTTGAACG | GAGCTATGTA |
|  | CCTACACGGG | CTGGGGCTTG | AGCCGCTGGG | CCGGGCGGCC | GGCAACTTGC | CTCGATACAT |

|  | 2470 | 2480 | 2490 | 2500 | 2510 | 2520 |
|---|---|---|---|---|---|---|
|  | CTACGGCAGC | GGCTGTCGCT | TCGACACGGT | GGAAATGGTG | GACGAGACGA | GACCCGCGCC |
|  | GATGCCGTCG | CCGACAGCGA | AGCTGTGCCA | CCTTTACCAC | CTGCTCTGCT | CTGGGGCGGG |

|  | 2530 | 2540 | 2550 | 2560 | 2570 | 2580 |
|---|---|---|---|---|---|---|
|  | GCCGGCGCTG | TCATCGCCCG | AAACCGGCGA | CGATAGCAAC | GACGACGCGG | TTGCCGGCGG |
|  | CGGCCGCGAC | AGTAGCGGGC | TTTGGCCGCT | GCTATCGTTG | CTGCTGCGCC | AACGGCCGCC |

|  | 2590 | 2600 | 2610 | 2620 | 2630 | 2640 |
|---|---|---|---|---|---|---|
|  | AGGTGCTGGC | GGGGTAACAT | CACCCGCGAC | TCGTACGACG | TCGCCGAACG | CACTGCTGCC |
|  | TCCACGACCG | CCCCATTGTA | GTGGGCGCTG | AGCATGCTGC | AGCGGCTTGC | GTGACGACGG |
|  |  | UL137 |  |  |  |  |

|  | 2650 | 2660 | 2670 | 2680 | 2690 | 2700 |
|---|---|---|---|---|---|---|
|  | AGAATGGATG | GATGCGGTGC | ATGTGGCGGT | CCAAGCCGCC | GTTCAAGCGA | CCGTGCAAGT |
|  | TCTTACCTAC | CTACGCCACG | TACACCGCCA | GGTTCGGCGG | CAAGTTCGCT | GGCACGTTCA |

|  | 2710 | 2720 | 2730 | UL136 2740 | 2750 | 2760 |
|---|---|---|---|---|---|---|
|  | AAGTGCCCCG | CGGGAGAACG | CCGTATCTCC | CGCTACGTAA | GAGGGTTGAG | GGGGCCGTTC |
|  | TTCACGGGGC | GCCCTCTTGC | GGCATAGAGG | GCGATGCATT | CTCCCAACTC | CCCCGGCAAG |

|  | 2770 | 2780 | 2790 | 2800 | 2810 | 2820 |
|---|---|---|---|---|---|---|
|  | CCGCGCGAGT | GCTGTACAAA | AGAGAGAGAC | TGGGACGTAG | ATCCGGACAG | AGGACGGTCA |
|  | GGCGCGCTCA | CGACATGTTT | TCTCTCTCTG | ACCCTGCATC | TAGGCCTGTC | TCCTGCCAGT |

```
UL138  2830                 2840       2850       2860       2870       2880
       CCATGGACGA TCTGCCGCTG AATGTCGGGT TACCCATCAT CGGCGTGATG CTCGTGCTGA
       GGTACCTGCT AGACGGCGAC TTACAGCCCA ATGGGTAGTA GCCGCACTAC GAGCACGACT 2890       2900       2910       2920       2930       2940
       TCGTGGCCAT CCTCTGCTAT CTGGCTTACC ACTGGCACGA CACCTTCAAA CTGGTGCGCA
       AGCACCGGTA GGAGACGATA GACCGAATGG TGACCGTGCT GTGGAAGTTT GACCACGCGT
UL137

2950       2960       2970       2980       2990       3000
       TGTTTCTGAG CTACCGCTGG CTGATCCGCT GTTGCGAGCT GTACGGGGAG TACGAGCGCC
       ACAAAGACTC GATGGCGACC GACTAGGCGA CAACGCTCGA CATGCCCCTC ATGCTCGCGG 3010       3020       3030       3040       3050       3060
       GGTTCGCGGA CCTGTCGTCT CTGGGCCTCG GCGCCGTACG GCGGGAGTCG GACAGACGAT
       CCAAGCGCCT GGACAGCAGA GACCCGGAGC CGCGGCATGC CGCCCTCAGC CTGTCTGCTA 3070       3080       3090       3100       3110       3120
       ACCGTTTCTC CGAACGGCCC GACGAGATCT TGGTCCGTTG GGAGGAAGTG TCTTCCCAGT
       TGGCAAAGAG GCTTGCCGGG CTGCTCTAGA ACCAGGCAAC CCTCCTTCAC AGAAGGGTCA 3130       3140       3150       3160       3170       3180
       GCAGCTACGC GTCGTCGCGG ATAACAGACC GCCGTGTGGG TTCATCGTCT TCGTCGTCGG
       CGTCGATGCG CAGCAGCGCC TATTGTCTGG CGGCACACCC AAGTAGCAGA AGCAGCAGCC 3190       3200       3210       3220       3230       3240
       TCCACGTCGC TAGCCAGAGA AACAGCGTGC CTCCGCCGGA CATGGGCGTG ACGGCGCCGC
       AGGTGCAGCG ATCGGTCTCT TTGTCGCACG GAGGCGGCCT GTACCGCCAC TGCCGCGGCG 3250       3260       3270       3280       3290       3300
       TGACCGACGT CGATCTGTTG AAACCCGTGA CGGGATCCGC GACGCAGTTC ACCACCGTAG
       ACTGGCTGCA GCTAGACAAC TTTGGGCACT GCCCTAGGCG CTGCGTCAAG TGGTGGCATC
```

```
       3310        3320        3330        3340        3350        3360
CCATGGTACA TTATCATCAA GAGTACACGT GAATGAGAAA AAGAAAAAAG AGGGGAGCGG
GGTACCATGT AATAGTAGTT CTCATGTGCA CTTACTCTTT TTCTTTTTTC TCCCCTCGCC
                                UL138

3370        3380        3390        3400        3410        3420
ATCGCGATAA TGTCGCTTTG ACATTCTCTG CTCGATCTAC TCAGCGTCTG CACGAAACGG
TAGCGCTATT ACAGCGAAAC TGTAAGAGAC GAGCTAGATG AGTCGCAGAC GTGCTTTGCC 3430        3440        3450        3460        3470        3480
CATCCGCACG GAGGCGAGCC CAAGCGTATC TGCAGCAAGC GGTTCTTTCC CTCGGTGATG
GTAGGCGTGC CTCCGCTCGG GTTCGCATAG ACGTCGTTCG CCAAGAAAGG GAGCCACTAC 3490        3500        3510        3520        3530        3540
GTGGCAGCAT CGGTGGCGGG AGCTTGTTCG GACGATGGAC GGTGAGGAGT CCCTGGCGAT
CACCGTCGTA GCCACCGCCC TCGAACAAGC CTGCTACCTG CCACTCCTCA GGGACCGCTA 3550        3560        3570        3580        3590        3600
CAGGCGGCTC CCGGTGTGG AGTTCAACGG GTGGTAAATGG TGGCGGTGAT CGGTGTTAGA
GTCCGCCGAG GGCCACACC TCAAGTTGCC CACCATTACC ACCGCCACTA GCCACAATCT 3610        3620        3630        3640        3650        3660
AAACGGTGGC CCTGGCAAAC ATATATCTAC TGTAAACCCT CTGCTCTGTT AATAAAAAGC
TTTGCCACCG GGACCGTTTG TATATAGATG ACATTTGGGA GACGAGACAA TTATTTTTCG 3670        3680        3690        3700        3710        3720
ACACTTTTCA CATGAGTTCG TAATTTTATT GTGTAGTGGA AATTTTTACG TCATTGGGAA
TGTGAAAAGT GTACTCAAGC ATTAAAATAA CACATCACCT TTAAAAATGC AGTAACCCTT 3730        3740        3750        3760        3770        3780
ACCCCAGAAT GAAAGAGTAT AATGTGCATA TCACCGGGGG TTCCCTGTCA GTACGAATGT
TGGGGTCTTA CTTTCTCATA TTACACGTAT AGTGGCCCCC AAGGGACAGT CATGCTTACA
```

*FIG._1D-2*

```
3790       3800       3810       3820       3830       3840
ACACAACGCG GGTTACATTA CGATAAACTT TCCGGTAAAA CGATGCCGAT ACAGCGTGTA
TGTGTTGCGC CCAATGTAAT GCTATTTGAA AGGCCATTTT GCTACGGCTA TGTCGCACAT 3850       3860       3870       3880       3890       3900
TAACGCTGAT TGTTACGACA AACGAGTTGG TATATCCATT ATATAGTAAC GAACATGCTG
ATTGCGACTA ACAATGCTGT TTGCTCAACC ATATAGGTAA TATATCATTG CTTGTACGAC
                                                       ↑
                                                      UL139

3910       3920       3930       3940       3950       3960
TGGATATTAG TTTTATTTGC ACTCGCCGCA TCGGCGAGTG AAACCACTAC AGGTACCAGC
ACCTATAATC AAAATAAACG TGAGCGGCGT AGCCGCTCAC TTTGGTGATG TCCATGGTCG 3970       3980       3990       4000       4010       4020
TCTAATTCCA GTCAATCTAC TAGTGCTACC GCCAACACGA CCGTATCGAC ATGTATTAAT
AGATTAAGGT CAGTTAGATG ATCACGATGG CGGTTGTGCT GGCATAGCTG TACATAATTA 4030       4040       4050       4060       4070       4080
GCCTCTAAAC GCAGTAGCTG GACAGTACCA CAGCTCGAGC TGCTTGCCGC TAGCGGCTGG
CGGAGATTTG CGTCATCGAC CTGTCATGGT GTCGAGCTCG ACGAACGGCG ATCGCCGACC 4090       4100       4110       4120       4130       4140
ACATTATCTG GACTCCTTCT CTTATTTACC TGCTGCTTTT GCTGCTTTTG GCTAGTACGT
TGTAATAGAC CTGAGGAAGA GAATAAATGG ACGACGAAAA CGACGAAAAC CGATCATGCA 4150       4160       4170       4180       4190       4200
AAAATCTGCA GCTGCTGCGG CAACTCCTCC GAGTCAGAGA GCAAAACAAC CCACGCGTAC
TTTTAGACGT CGACGACGCC GTTGAGGAGG CTCAGTCTCT CGTTTTGTTG GGTGCGCATG 4210       4220       4230       4240       4250       4260
ACCAATGCCG CATTCACTTC TTCCGACTTC ACGTTACCCA TGGGCACTAC AGGGTCGTAC
TGGTTACGGC GTAAGTGAAG AAGGCTGAAG TGCAATGGGT ACCCGTGATG TCCCAGCATG
```

*FIG.\_1E-1*

```
      4270         4280         4290         4300         4310         4320
ACTCCCCCAC   AGGACGGCTC   ATTTCCACCT   CCGCCTCGGT   GACGTAGGCT   AAACCGAAAC
TGAGGGGGTG   TCCTGCCGAG   TAAAGGTGGA   GGCGGAGCCA   CTGCATCCGA   TTTGGCTTTG
                                                   └─UL139

4330         4340         4350         4360         4370         4380
CCACGTTGAA   CCTAACGCGG   TTTCGGAAGG   CCTGAGACGT   CACTTTCACA   ATGACGTCCG
GGTGCAACTT   GGATTGCGCC   AAAGCCTTCC   GGACTCTGCA   GTGAAAGTGT   TACTGCAGGC 4390         4400         4410         4420         4430         4440
TATACACGTT   CATCATAAAA   CACCGTAGAG   GCTAAGGCTT   CGGTAGGGAG   AGACCTCAAC
ATATGTGCAA   GTAGTATTTT   GTGGCATCTC   CGATTCCGAA   GCCATCCCTC   TCTGGAGTTG 4450         4460         4470         4480    UL140  4490    4500
TGTTCCTGAT   GAGCACCCGT   GCTCTCATCT   CTTCAGACTT   GTC ATGACCC   CCGCTCAGAC
ACAAGGACTA   CTCGTGGGCA   CGAGAGTAGA   GAAGTCTGAA   CAG TACTGGG   GGCGAGTCTG 4510         4520         4530         4540         4550         4560
TAACGCGACT   ACCACCGTGC   ACCCGCACGA   CGCAAAAAAC   GGCAGCGGCG   GTAGTGCCCT
ATTGCGCTGA   TGGTGGCACG   TGGGCGTGCT   GCGTTTTTTG   CCGTCGCCGC   CATCACGGGA 4570         4580         4590         4600         4610         4620
GCCGACCCTC   GTCGTTTTCG   GCTTTATCGT   TACGCTACTT   TTCTTTCTCT   TTATGCTCTA
CGGCTGGGAG   CAGCAAAAGC   CGAAATAGCA   ATGCGATGAA   AAGAAAGAGA   AATACGAGAT 4630         4640         4650         4660         4670         4680
CTTTTGGAAC   AACGACGTGT   TCCGTAAGCT   GCTCCGTGCG   CTTGGATCCA   GCGCTGTTGC
GAAAACCTTG   TTGCTGCACA   AGGCATTCGA   CGAGGCACGC   GAACCTAGGT   CGCGACAACG 4690         4700         4710         4720         4730         4740
GACCGCTTCG   ACGCGTGGCA   AGACGAGGTC   ATCTACCGTC   GTCCATCACG   TCGTTCCCAG
CTGGCGAAGC   TGCGCACCGT   TCTGCTCCAG   TAGATGGCAG   CAGGTAGTGC   AGCAAGGGTC
```

FIG.–1E-2

FIG._1F-1

```
      5230       5240       5250       5260       5270       5280
TCAGTTGCGG GCATCCCGGG CGAGAAGCTG CGTCGCACGG TGGTCACCAC CACGCCGGCC
AGTCAACGCC CGTAGGGCCC GCTCTTCGAC GCAGCGTGCC ACCAGTGGTG GTGCGGCCGG 5290       5300       5310       5320       5330       5340
CGACGTTTGA GCGGCCGACA CACGGAGCAG GAGCAGGCGG GCATGCGTCT CTGTGAAAAA
GCTGCAAACT CGCCGGCTGT GTGCCTCGTC CTCGTCCGCC CGTACGCAGA GACACTTTTT 5350       5360       5370       5380       5390       5400
GGGAAGAAAA GAATCATCAT GTGCCGCCGG GAGTCGCTCC GAACTCTGCC GTGGCTGTTC
CCCTTCTTTT CTTAGTAGTA CACGGCGGCC CTCAGCGAGG CTTGAGACGG CACCGACAAG 5410       5420       5430       5440       5450       5460
TGGGTGCTGT TGAGCTGCCC GCGACTCCTC GAATATTCTT CCTCTTCGTT CCCCTTCGCC
ACCCACGACA ACTCGACGGG CGCTGAGGAG CTTATAAGAA GGAGAAGCAA GGGGAAGCGG 5470       5480       5490       5500       5510       5520
ACCGCTGACA TTGCCGAAAA GATGTGGGCC GAGAATTATG AGACCACGTC GCCGGCGCCG
TGGCGACTGT AACGGCTTTT CTACACCCGG CTCTTAATAC TCTGGTGCAG CGGCCGCGGC 5530       5540       5550       5560       5570       5580
GTGTTGGTCG CCGAGGGAGA GCAAGTTACC ATCCCCTGCA CGGTCATGAC ACACTCCTGG
CACAACCAGC GGCTCCCTCT CGTTCAATGG TAGGGGACGT GCCAGTACTG TGTGAGGACC 5590       5600       5610       5620       5630       5640
CCCATGGTCT CCATTCGCGC ACGTTTCTGT CGTTCCCACG ACGGCAGCGA CGAGCTCATC
GGGTACCAGA GGTAAGCGCG TGCAAAGACA GCAAGGGTGC TGCCGTCGCT GCTCGAGTAG
```

*FIG._1F-2*

```
5650       5660       5670       5680       5690       5700
CTGGACGCCG TCAAAGGCCA TCGGCTGATG AACGGACTCC AGTACCGCCT GCCGTACGCC
GACCTGCGGC AGTTTCCGGT AGCCGACTAC TTGCCTGAGG TCATGGCGGA CGGCATGCGG 5710       5720       5730       5740       5750       5760
ACTTGGAATT TCTCGCAATT GCATCTCGGC CAAATATTCT CGCTTACTTT TAACGTATCG
TGAACCTTAA AGAGCGTTAA CGTAGAGCCG GTTTATAAGA GCGAATGAAA ATTGCATAGC 5770       5780       5790       5800       5810       5820
ATGGACACAG CCGGCATGTA CGAATGCGTG CTACGCAACT ACAGCCACGG CCTCATCATG
TACCTGTGTC GGCCGTACAT GCTTACGCAC GATGCGTTGA TGTCGGTGCC GGAGTAGTAC 5830       5840       5850       5860       5870       5880
CAACGCTTCG TAATTCTCAC GCAGCTGGAG ACGCTCAGCC GGCCCGACGA ACCTTGCTGC
GTTGCGAAGC ATTAAGAGTG CGTCGACCTC TGCGAGTCGG CCGGGCTGCT TGGAACGACG 5890       5900       5910       5920       5930       5940
ACACCGGCGT TAGGTCGCTA CTCGCTGGGA GACCAGATCT GGTCGCCGAC GCCCTGGCGT
TGTGGCCGCA ATCCAGCGAT GAGCGACCCT CTGGTCTAGA CCAGCGGCTG CGGGACCGCA 5950       5960       5970       5980       5990       6000
CTACGGAATC ACGACTGCCG AACGTACCGC GGCTTTCAAC GCAACTACTT CTATATCGGC
GATGCCTTAG TGCTGACGCC TTGCATGGCG CCGAAAGTTG CGTTGATGAA GATATAGCCG 6010       6020       6030       6040       6050       6060
CGCGCCGACG CCGAGGATTG CTGGAAACCC GCATGTCCGG ACGAGGAACC CGACCGCTGT
GCGCGGCTGC GGCTCCTAAC GACCTTTGGG CGTACAGGCC TGCTCCTTGG GCTGGCGACA 6070       6080       6090       6100       6110       6120
TGGACAGTGA TACAGCGTTA CCGGCTCCCC GGCGACTGCT ACCGTTCGCA GCCACACCCG
ACCTGTCACT ATGTCGCAAT GGCCGAGGGG CCGCTGACGA TGGCAAGCGT CGGTGTGGGC
```

*FIG._1G-1*

```
                6130                  6140                  6150                  6160                  6170                  6180
           CCGAAATTTT            TACCGGTGAC            GCCAGCACCG            CCGGCCGACA            TAGACACCGG            GATGTCTCCC
           GGCTTTAAAA            ATGGCCACTG            CGGTCGTGGC            GGCCGGCTGT            ATCTGTGGCC            CTACAGAGGG 6190                  6200                  6210                  6220                  6230                  6240
           TGGGCCACTC            GGGGAATCGC            GGCGTTTTTG            GGGTTTTGA             GTATTTTTAC            CGTATGTTTC
           ACCCGGTGAG            CCCCTTAGCG            CCGCAAAAAC            CCCAAAACCT            CATAAAAATG            GCATACAAAG 6250                  6260                  6270                  6280                  6290                  6300
           CTATGCTACC            TGTGTTATCT            GCAGTGTTGT            GGACGCTGGT            GTCCCACGCC            GGGAAGGGGA
           GATACGATGG            ACACAATAGA            CGTCACAACA            CCTGCGACCA            CAGGGTGCGG            CCCTTCCCCT 6310                  6320                  6330                  6340                  6350                  6360
           CGACGAGGCG            GTGAGGGCTA            TCGACGCCTA            CCGACTTACG            ATAGTTACCC            CGGTGTTAGA
           GCTGCTCCGC            CACTCCCGAT            AGCTGCGGAT            GGCTGAATGC            TATCAATGGG            GCCACAATCT

UL141    6380                  6390                  6400                  6410                  6420
           6370                  GGTGAGAACA            CGTATAAAAT            AAAAAAATAA            TATGTTAAAA            AATGCAGTGT
           AAGATGAAGA            CCACTCTTGT            GCATATTTTA            TTTTTTTATT            ATACAATTTT            TTACGTCACA
           TTCTACTTCT 6430                  6440                  6450    UL142    6460                  6470                  6480
           GTGAAGTGTG            AATAGTGTGA            TTAAAATATG            CGGATTGAAT            GGGTGTGGTG            GTTATTCGGA
           CACTTCACAC            TTATCACACT            AATTTTATAC            GCCTAACTTA            CCCACACCAC            CAATAAGCCT 6490                  6500                  6510                  6520                  6530                  6540
           TACTTTGTGT            CATCCGTTGG            GAGCGAACGG            TCATTATCCT            ATCGTTACCA            CTTGGAATCT
           ATGAAACACA            GTAGGCAACC            CTCGCTTGCC            AGTAATAGGA            TAGCAATGGT            GAACCTTAGA 6550                  6560                  6570                  6580                  6590                  6600
           AATTCATCTA            CCAACGTGGT            TTGCAACGGA            AACATTCCG             TGTTTGTAAA            CGGCACCCTA
           TTAAGTAGAT            GGTTGCACCA            AACGTTGCCT            TTGTAAAGGC            ACAAACATTT            GCCGTGGGAT
```

*FIG._1G-2*

```
6610       6620       6630       6640       6650       6660
GGTGTGCGGT ATAACATTAC GGTAGGAATC AGTTCGTCTT TATTAATAGG ACACCTTACT
CCACACGCCA TATTGTAATG CCATCCTTAG TCAAGCAGAA ATAATTATCC TGTGGAATGA 6670       6680       6690       6700       6710       6720
ATACAAGTAT TGGAATCATG GTTCACACCC TGGGTCCAAA ATAAAAGTTA CAACAAACAA
TATGTTCATA ACCTTAGTAC CAAGTGTGGG ACCCAGGTTT TATTTTCAAT GTTGTTTGTT 6730       6740       6750       6760       6770       6780
CCCCTAGGTG ACACTGAAAC GCTTTATAAT ATAGATAGCG AAAACATTCA TCGCGTATCT
GGGGATCCAC TGTGACTTTG CGAAATATTA TATCTATCGC TTTTGTAAGT AGCGCATAGA 6790       6800       6810       6820       6830       6840
CAATATTTTC ACACAAGATG GATAAAATCT CTGCAAGAGA ATCACACTTG CGACCTCACA
GTTATAAAAG TGTGTTCTAC CTATTTTAGA GACGTTCTCT TAGTGTGAAC GCTGGAGTGT 6850       6860       6870       6880       6890       6900
AACAGTACAC CTACCTATAC ATATCAAGTA AACGTGAACA ACACGAATTA CCTAACACTA
TTGTCATGTG GATGGATATG TATAGTTCAT TTGCACTTGT TGTGCTTAAT GGATTGTGAT 6910       6920       6930       6940       6950       6960
ACATCCTCGG GATGGCAAGA CCGTCTAAAT TACACCGTCA TAAATAGTAC ACACTTTAAC
TGTAGGAGCC CTACCGTTCT GGCAGATTTA ATGTGGCAGT ATTTATCATG TGTGAAATTG 6970       6980       6990       7000       7010       7020
CTCACAGAAT CGAACATAAC CAGCATTCAA AAATATCTCA ACACTACCTG CATAGAAAGA
GAGTGTCTTA GCTTGTATTG GTCGTAAGTT TTTATAGAGT TGTGATGGAC GTATCTTTCT 7030       7040       7050       7060       7070       7080
CTCCGTAACT ACCCTTTGGA GTCCGTATAC ACCACAACTG TGCCTCAAAA CATAACAACA
GAGGCATTGA TGGGAAACCT CAGGCATATG TGGTGTTGAC ACGGAGTTTT GTATTGTTGT
```

FIG._1H-1

```
                    7090                     7100                     7110                     7120                     7130                     7140
TCTCAACACG    CAACAACCAC    TATGCACACA    ATACCTCCAA    ATACAATAAC    AATTCAAAAT
AGAGTTGTGC    GTTGTTGGTG    ATACGTGTGT    TATGGAGGTT    TATGTTATTG    TTAAGTTTTA 7150                     7160                     7170                     7180                     7190                     7200
ACAACTCAAA    GCCATACTGT    ACAGACGCCG    TCTTTTAACG    ACACACATAA    CGTGACGAAA
TGTTGAGTTT    CGGTATGACA    TGTCTGCGGC    AGAAAATTGC    TGTGTGTATT    GCACTGCTTT 7210                     7220                     7230                     7240                     7250                     7260
CACACGTTAA    ACATAAGCTA    CGTTTTATCA    CAAAAAACGA    ATAACACAAC    ATCACCGTGG
GTGTGCAATT    TGTATTCGAT    GCAAAATAGT    GTTTTTTGCT    TATTGTGTTG    TAGTGGCACC 7270                     7280                     7290                     7300                     7310                     7320
ATATATGCCA    TACCTATGGG    CGCTACAGCC    ACAATAGGCG    CCGGTTTATA    TATCGGGAAA
TATATACGGT    ATGGATACCC    GCGATGTCGG    TGTTATCCGC    GGCCAAATAT    ATAGCCCTTT

7330         UL143  7350                     7360    UL142  7370                     7380
CACTTTACGC    CGGTTAAGTT    CGTATACGAG    GTATGGCGCG    GTCAGTAAAG    ACGATTCGGA
GTGAAATGCG    GCCAATTCAA    GCATATGCTC    CATACCGCGC    CAGTCATTTC    TGCTAAGCCT 7390                     7400                     7410                     7420                     7430                     7440
TTCAACACAT    ATACTCCCCA    CGATCCTCGA    ACACCTTACA    GCATATGAGC    AAAAACAAG
AAGTTGTGTA    TATGAGGGGT    GCTAGGAGCT    TGTGGAATGT    CGTATACTCG    TTTTTTGTTC 7450                     7460                     7470                     7480                     7490                     7500
AAAGTATAGC    CACAATCACA    TTTGGGCGAA    TAACATGCTG    TCATCCACTA    GCGTCTATTA
TTTCATATCG    GTGTTAGTGT    AAACCCGCTT    ATTGTACGAC    AGTAGGTGAT    CGCAGATAAT 7510                     7520                     7530                     7540                     7550                     7560
ATCTAATGTT    TAACGGGAGC    TGTACTGTCA    CCGTTAAAAT    TCATCCATGGGA    ATCAACGGGT
TAGATTACAA    ATTGCCCTCG    ACATGACAGT    GGCAATTTTA    TAGGTACCCT    TAGTTGCCCA
```

FIG._1H-2

```
              7570            7580            7590            7600            7610            7620
         CAACCAACGT       CCATCAGCTT      GTGATTGTGC      TCCATCTGGG      TAACCGCTGT      CAGCCTTGGC
         GTTGGTTGCA       GGTAGTCGAA      CACTAACACG      AGGTAGACCC      ATTGGCGACA      GTCGGAACCG

UL143   7630           7640            7650            7660            7670            7680
         GACAGTGTA  ATCACAGCTG       TCACATAACT      CACGAAGCCT      CCAATCACAG      CAGCACACAT
         CTGTCCACAT TAGTGTCGAC       AGTGTATTGA      GTGCTTCGGA      GGTTAGTGTC      GTCGTGTGTA 7690            7700            7710            7720            7730            7740
         AGTCCTAACG       CCATTGGCGT      GTATAAAAGT      TCGGAAAACT      TGACGGTTGT      ACGGCACGAC
         TCAGGATTGC       GGTAACCGCA      CATATTTTCA      AGCCTTTTGA      ACTGCCAACA      TGCCGTGCTG 7750            7760            7770            7780            7790            7800
         AAATCGATGT       AGTGGTATGT      TTTTCCAGCA      GAGACCGTGT      GCGGTCTCTT      AGGTTCGCTA
         TTTAGCTACA       TCACCATACA      AAAAGGTCGT      CTCTGGCACA      CGCCAGAGAA      TCCAAGCGAT 7810            7820            7830            7840            7850            7860
         TACTGTGGCT       GGAAACTGGT      TACCTGTGAA      GATGGCTAAC      TATCCTGTTC      TGTCCTGAA
         ATGACACCGA       CCTTTGACCA      ATGGACACTT      CTACCGATTG      ATAGGACAAG      ACAGGACCTT 7870            7880            7890            7900            7910            7920
         AAACTTTTGG       CGTCGTAGGT      GGACTTTGCA      GTATGCGGGT      TAGTGAAGTT      ATGTCATTTA
         TTTGAAAACC       GCAGCATCCA      CCTGAAACGT      CATACGCCCA      ATCACTTCAA      TACAGTAAAT 7930            7940            7950            7960            7970            7980
         TTTACGTTTA       CGATCTCGTA      TTACAAACCG      CGGAGAGGAT      GATACCGTTC      GGCCCCATGA
         AAATGCAAAT       GCTAGAGCAT      AATGTTTGGC      GCCTCTCCTA      CTATGGCAAG      CCGGGGTACT 7990            8000        8010 UL144  8020            8030            8040
         GTTATTTTA        TTCTTCCGGT      AGGAGGCATG  AAGCCTCTGA      TAATGCTCAT      CTGCTTTGCT
         CAATAAAAAT       AAGAAGGCCA      TCCTCCGTAC  TTCGGAGACT      ATTACGAGTA      GACGAAACGA
```

FIG. _11-1

```
       8050                8060       8070       8080       8090       8100
GTGATATTAT TGCAGCTTGG AGTGACTAAA GTGTGTCAGC ATAATGAAGT GCAACTGGGC
CACTATAATA ACGTCGAACC TCACTGATTT CACACAGTCG TATTACTTCA CGTTGACCCG 8110       8120       8130       8140       8150       8160
AATGAGTGCT GCCCTCCGTG TGGTTCGGGA CAAAGAGTTA CTAAAGTATG CACGGATTAT
TTACTCACGA CGGGAGGCAC ACCAAGCCCT GTTTCTCAAT GATTTCATAC GTGCCTAATA 8170       8180       8190       8200       8210       8220
ACCAGTGTAA CGTGTACCCC TTGCCCCAAC GGCACGTATG TATCGGGACT TTACAACTGT
TGGTCACATT GCACATGGGG AACGGGGTTG CCGTGCATAC ATAGCCCTGA AATGTTGACA 8230       8240       8250       8260       8270       8280
ACCGATTGCA CTCAATGTAA CGTCACTCAG GTCATGATTC GTAACTGCAC TTCCACCAAT
TGGCTAACGT GAGTTACATT GCAGTGAGTC CAGTACTAAG CATTGACGTG AAGGTGGTTA 8290       8300       8310       8320       8330       8340
AATACCGTAT GCGCACCTAA GAACCATACG TACTTTTCCA CTCCAGGCGT CCAACATCAC
TTATGGCATA CGCGTGGATT CTTGGTATGC ATGAAAAGGT GAGGTCCGCA GGTTGTAGTG 8350       8360       8370       8380       8390       8400
AAACAACGAC AGCAAAATCA TACCGCACAT ATAACCGTCA AACAAGGAAA AAGCGGTCGT
TTTGTTGCTG TCGTTTTAGT ATGGCGTGTA TATTGGCAGT TTGTTCCTTT TTCGCCAGCA 8410       8420       8430       8440       8450       8460
CATACTCTAG CCTGGTGTC  TCTCTTTATC TTTCTGTGG  GTATCATACT TTTAATTCTC
GTATGAGATC GGACCAACAG AGAGAAATAG AAAGAACACC CATAGTATGA AAATTAAGAG 8470       8480       8490       8500       8510       8520
TATCTTATAG CCGCCTATCG GAGTGAGAGA TGCCAACAGT GTTGCTCAAT CGGCAAAATT
ATAGAATATC GGCGGATAGC CTCACTCTCT ACGGTTGTCA CAACGAGTTA GCCGTTTTAA
```

FIG._1I-2

```
         8530       UL144 8540       8550       8560       8570       8580
    TTCTACCGCA  CCCTGTAAGC TTCCTGTTGT TGTTTTTACA TCACGGTACG ATGAAGTCAC
    AAGATGGCGT  GGGACATTCG AAGGACAACA ACAAAAATGT AGTGCCATGC TACTTCAGTG 8590       8600       8610       8620       8630       8640
    ACAGATAATT ACAGATGAGC TGTTCATATT TTTTATTATT TTTTCCAATT CCTGCACTAA
    TGTCTATTAA TGTCTACTCG ACAAGTATAA AAAATAATAA AAAAGGTTAA GGACGTGATT 8650       8660       8670       8680       8690       8700
    AAAAAGAAGC ACTTTACGGA ACCGTGTCTG AGTATCTGTG GGGAATTTAG GTACTTTTTG
    TTTTCTTCG  TGAAATGCCT TGGCACAGAC TCATAGACAC CCCTTAAATC CATGAAAAAC 8710       8720       8730       8740       8750       8760
    CCGACGTCAG GAAAATAAAG TGTCGCCTAC ATAAGAGCCC GGTGCTATCG TGCTGTCACT
    GGCTGCAGTC CTTTTTATTC ACAGCGGATG TATTCTCGGG CCACGATAGC ACGACAGTGA 8770       8780       8790       8800       8810       8820
    CTTTCTTGTT GCCTTCGATG TACGGCGTCC TGGCTCATTA CTACTCCTTC ATCAGTAGCC
    GAAAGAACAA CGGAAGCTAC ATGCCGCAGG ACCGAGTAAT GATGAGGAAG TAGTCATCGG 8830       8840       8850       8860  UL145 8870       8880
    CCAGCGTTAT GGTTAATTTT AAGCATCATA ACGCCGTGCA GCTGTTATGT GCACGGACCC
    GGTCGCAATA CCAATTAAAA TTCGTAGTAT TGCGGCACGT CGACAATACA CGTGCCTGGG 8890       8900       8910       8920       8930       8940
    GAGACGCACT GCCGGATGGG AACGTTTAAC CCATCATGCG TCGTATCACG CGAACTACGG
    CTCTGCGTGA CGGCCTACCC TTGCAAATTG GGTAGTACGC AGCATAGTGC GCTTGATGCC 8950       8960       8970       8980       8990       9000
    GGCATACGCC GTGTTGATGG CTACATCGCA AAGAAAGTCC CTAGTGTTAC ATCGATACAG
    CCGTATGCGG CACAACTACC GATGTAGCGT TTCTTTCAGG GATCACAATG TAGCTATGTC
```

*FIG._1J-1*

| 9010 TGCCGTGACA ACGGCACTGT | 9020 GCCGTGGCCC CGGCACCGGG | 9030 TGCAGCTCAT ACGTCGAGTA | 9040 GCCTGTTGAG CGGACAACTC | 9050 ATCGTCCGCA TAGCAGGCGT | 9060 AGCTAGATCA TCGATCTAGT |
| --- | --- | --- | --- | --- | --- |
| 9070 GTCGGACTGG CAGCCTGACC | 9080 GTGCGGGGTG CACGCCCCAC | 9090 CCTGGATCGT GGACCTAGCA | 9100 GTCAGAGACT CAGTCTCTGA | 9110 TTTCCAACTA AAAGGTTGAT | 9120 GCGACCCCAA CGCTGGGGTT |
| 9130 AGGAGTTTGG TCCTCAAACC | 9140 AGCGACGATG TCGCTGCTAC | 9150 ACTCCCTCGAT TGAGGAGCTA | 9160 GGGTGGAAGT CCCACCTTCA | UL145 9170 GATGATTGAT CTACTAACTA | 9180 GATGAGAACC CTACTCTTGG |
| 9190 TGACAAGAAA ACTGTTCTTT | 9200 GACGAGAGAG CTGCTCTCTC | 9210 CTGTCATTGT GACAGTAACA | 9220 AGAATTAGTC TCTTAATCAG | 9230 TAGATTCCTG ATCTAAGGAC | |
| 9250 ATAATAAACA TATTATTTGT | 9260 GTATCGATTT CATAGCTAAA | 9270 TGAAACCTAA ACTTTGGATT | 9280 TTGACGTGTG AACTGCACAC | 9290 ATCGATTTTT TAGCTAAAAA | 9300 AAACCTCTGT TTTGGAGACA |
| 9310 GTTGTGTGAT CAACACACTA | 9320 TGATTGGTAT ACTAACCATA | 9330 GTGGGGGGAT CACCCCCCTA | 9340 CCGATTTCAA GGCTAAAGTT | 9350 AGGGGGGTAC TCCCCCCATG | 9360 TTATCGGGAA AATAGCCCTT |
| 9370 TTGATGTGTC ATGGACGCAG AACTACACAG TACCTGCGTC | | 9390 TTTTGAGCGA AAAACTCGCT | 9400 TTTTCCGGGA AAAAGGCCCT | 9410 ATACCGGATA TATGGCCTAT | 9420 TTACGAATTA AATGCTTAAT |

FIG._1J-2

```
      9430        9440        9450  UL146 9460        9470        9480
CTGGTAGTGA  CGTAGATAAT  AAAATTATAA  TGCGATTAAT  TTTTGGTGCG  TTGATTATTT
GACCATCACT  GCATCTATTA  TTTTAATATT  ACGCTAATTA  AAAACCACGC  AACTAATAAA 9490        9500        9510        9520        9530        9540
TTTTAGCATA  TGTGTATCAT  TATGAGGTGA  ATGGAACAGA  ATTACGCTGC  AGATGTCTTC
AAAATCGTAT  ACACATAGTA  ATACTCCACT  TACCTTGTCT  TAATGCGACG  TCTACAGAAG 9550        9560        9570        9580        9590        9600
ATAGAAAATG  GCCGCCTAAT  AAAATTATAT  TGGGTAATTA  TTGGCTTCAT  CGCGATCCCA
TATCTTTTAC  CGGCGGATTA  TTTTAATATA  ACCCATTAAT  AACCGAAGTA  GCGCTAGGGT 9610        9620        9630        9640        9650        9660
GAGGGCCCGG  ATGCGATAAA  AATGAACATT  TATTGTATCC  AGACGGAAGG  AAACCGCCTG
CTCCCGGGCC  TACGCTATTT  TTACTTGTAA  ATAACATAGG  TCTGCCTTCC  TTTGGCGGAC 9670        9680        9690        9700        9710        9720
GACCTGGAGT  ATGTTTATCG  CCCGATCACC  TCTTCTCAAA  ATGGTTAGAC  AAACACAACG
CTGGACCTCA  TACAAATAGC  GGGCTAGTGG  AGAAGAGTTT  TACCAATCTG  TTTGTGTTGC 9730        9740        9750        9760        9770        9780
ATAATAGGTG  GTATAATGTT  AACATAACGA  AATCACCAGG  ACCGAGACGA  ATAAATATAA
TATTATCCAC  CATATTACAA  TTGTATTGCT  TTAGTGGTCC  TGGCTCTGCT  TATTTATATT 9790        9800  UL146 9810        9820        9830        9840
CCTTGATAGG  TGTTAGAGGA  TAATATTTAA  TGTATGTTTT  CAAACAGACA  AGTTCGTTAA
GGAACTATCC  ACAATCTCCT  ATTATAAATT  ACATACAAAA  GTTTGTCTGT  TCAAGCAATT 9850        9860  9870 UL147 9880        9890        9900
AACAAAATAT  TACAGTATGT  GTTTAAATATG  GTGCTAACAT  GGTTGCACCA  TCCGGTTTCA
TTGTTTTATA  ATGTCATACA  CAAATTATAC  CACGATTGTA  CCAACGTGGT  AGGCCAAAGT
```

*FIG._1K-1*

```
9910       9920       9930       9940       9950       9960
AACTCGCATA TCAATCTGTT ATCGGTACGA CACCTGTCAT TAATCGCATA TATGTTACTT
TTGAGCGTAT AGTTAGACAA TAGCCATGCT GTGGACAGTA ATTAGCGTAT ATACAATGAA 9970       9980       9990       10000      10010      10020
ACCATATGTC CCCTAGCCGT CCATGTTTTA GAACTAGAAG ATTACGACAG GCGCTGCCGT
TGGTATACAG GGGATCGGCA GGTACAAAAT CTTGATCTTC TAATGCTGTC CGCGACGGCA 10030      10040      10050      10060      10070      10080
TGCAACAACC AAATTCTGTT GAATACCCTG CCGGTCGGAA CCGAATTGCT TAAGCCAATC
ACGTTGTTGG TTTAAGACAA CTTATGGGAC GGCCAGCCTT GGCTTAACGA ATTCGGTTAG 10090      10100      10110      10120      10130      10140
GCAGCGAGCG AAAGCTGCAA TCGTCAGGAA GTGCTGGCTA TTTTAAAGGA CAAGGAACC
CGTCGCTCGC TTTCGACGTT AGCAGTCCTT CACGACCGAT AAAATTCCT GTTCCCTTGG 10150      10160      10170      10180      10190      10200
AAGTGTCTCA ATCCTAACGC GCAAGCCGTG CGTCGTCACA CGTAACCGGCT ATTTTTTCGG
TTCACAGAGT TAGGATTGCG CGTTCGGCAC GCAGCAGTGT AGTTGGCCGA TAAAAAAGCC 10210      10220      10230      10240      10250      10260
TTAATCTTAG ACGAGGAACA ACGCATTTAC GACGTAGTGT CTACCAATAT TGAGTTCGGT
AATTAGAATC TGCTCCTTGT TGCGTAAATG CTGCATCACA GATGGTTATA ACTCAAGCCA 10270      10280      10290      10300      10310      10320
GCCTGGCCAG TCCCTACGGC CTACAAAGCC TTTCTTTGGA AATACGCCAA GAGACTGAAC
CGGACCGGTC AGGGATGCCG GATGTTTCGG AAAGAAACCT TTATGCGGTT CTCTGACTTG 10330      10340      UL147 10350 10360      10370      10380
TACCACCACT TCAGACTGCG CTGGTGATCA TGTCCCTATT TTACCGTGCG GTAGCTCTGG
ATGGTGGTGA AGTCTGACGC GACCACTAGT ACAGGGATAA AATGGCACGC CATCGAGACC
```

FIG._1K-2

```
10390      10400      10410      10420      10430      10440
GCACGCTAAG CGCTTTGGTG TGGTACAGCA CTAGCATCCT CGCAGAGATT AACGAAAATT
CGTGCGATTC GCGAAACCAC ACCATGTCGT GATCGTAGGA GCGTCTCTAA TTGCTTTTAA 10450      10460      10470      10480      10490      10500
CCTGCTCCTC ATCTTCTGCG GATCACGAAG ACTGCGAGGA ACCGGACGAG ATCGTTCGCG
GGACGAGGAG TAGAAGACGC CTAGTGCTTC TGACGCTCCT TGGCCTGCTC TAGCAAGCGC 10510      10520      10530      10540      10550      10560
AAGAGCAAGA CTATCGGGCT CTGCTGGCCT TTTCCCTAGT GATTTGCGGT ACGCTCCTCG
TTCTCGTTCT GATAGCCCGA GACGACCGGA AAAGGGATCA CTAAACGCCA TGCGAGGAGC 10570      10580      10590      10600      10610      10620
TCACTTGTGT GATCTGAGAC GTCATGCTGG TAGCGTTTAT GAGTCGGGCG GTGGCCGACA
AGTGAACACA CTAGACTCTG CAGTACGACC ATCGCAAATA CTCAGCCCGC CACCGGCTGT 10630      10640      10650 UL148 10660      10670      10680
CGCCGCATTT CCTAACCCGC GCAGCATGTT GCGCTTGCTG TTCACGCTCG TCCTGCTGGC
GCGGCGTAAA GGATTGGGCG CGTCGTACAA CGCGAACGAC AAGTGCGAGC AGGACGACCG 10690      10700      10710      10720      10730      10740
CCTCCACGGG CAGTCTGTCG GCGCTAGCCG CGACTATGTG CATGTTCGC TACTGAGCTA
GGAGGTGCCC GTCAGACAGC CGCGATCGGC GCTGATACAC GTACAAGCCG ATGACTCGAT 10750      10760      10770      10780      10790      10800
CCGAGGCGAC CCCCTGGTCT TCAAGCACAC TTTCTCGGGT GTGCGTCGAC CCTTCACCGA
GGCTCCGCTG GGGACCAGA AGTTCGTGTG AAAGAGCCCA CACGCAGCTG GGAAGTGGCT 10810      10820      10830      10840      10850      10860
GCTAGGCTGG GCTGCGTGTC GCGACTGGGA CAGTATGCAT TGCACACCCT TCTGTTCTAC
CGATCCGACC CGACGCACAG CGCTGACCCT GTCATACGTA ACGTGTGGGA AGACCAGATG
```

*FIG._1L-1*

```
        10870      10880      10890      10900      10910      10920
CGATCTGGAG CAGATGACCG ACTCGGTGCG GCGTTACAGC ACGGTGAGCC CCGGCAAGGA
GCTAGACCTC GTCTACTGGC TGAGCCACGC CGCAATGTCG TGCCACTCGG GGCCGTTCCT 10930      10940      10950      10960      10970      10980
AGTGACGCTT CAGCTTCACG GGAACCAAAC CGTACAGCCG TCGTTTCTAA GCTTTACGTG
TCACTGCGAA GTCGAAGTGC CCTTGGTTTG GCATGTCGGC AGCAAAGATT CGAAATGCAC 10990      11000      11010      11020      11030      11040
CCGCCTGCAG CTAGAACCCG TGGTGAAAA TGTTGGCCTC TACGTGGCCT ACGTGGTCAA
GGCGGACGTC GATCTTGGGC ACCACCTTTT ACAACCGGAG ATGCACCGGA TGCACCAGTT 11050      11060      11070      11080      11090      11100
CGACGGCGAA CGCCCACAAC AGTTTTTTAC ACCGCAGGTA GACGTGGTAC GCTTTGCTCT
GCTGCCGCTT GCGGGTGTTG TCAAAAAATG TGGCGTCCAT CTGCACCATG CGAAACGAGA 11110      11120      11130      11140      11150      11160
ATATCTAGAA ACACTCTCCC GGATCGTGGA ACCGTTAGAA TCAGGTCGCC TGGCAGTGGA
TATAGATCTT TGTGAGAGGG CCTAGCACCT TGGCAATCTT AGTCCAGCCG ACCGTCACCT 11170      11180      11190      11200      11210      11220
ATTTGATACG CCTGACCTAG CTCTGGCGCC CGATTAGTA AGCAGCCTCT TCGTGGCCGG
TAAACTATGC GGACTGGATC GAGACCGCGG GCTAAATCAT TCGTCGGAGA AGCACCGGCC 11230      11240      11250      11260      11270      11280
ACACGGCGAG ACCGACTTTT ACATGAACTG GACGCTGCGT CGCAGTCAGA CCCACTACCT
TGTGCCGCTC TGGCTGAAAA TGTACTTGAC CTGCGACGCA GCGTCAGTCT GGGTGATGGA 11290      11300      11310      11320      11330      11340
GGAGGAGATG GCCTTACAGG TGGAGATTCT AAAACCCCGC GGCGTACGTC ACCGGCTAT
CCTCCTCTAC CGGAATGTCC ACCTCTAAGA TTTTGGGGCG CCGCATGCAG TGGCGCGATA
```

```
       11350         11360         11370         11380         11390         11400
TATCCACCAT    CCGAAGCTAC    AGCCGGGCGT    TGGCCTGTGG    ATAGATTTCT    GCGTGTACCG
ATAGGTGGTA    GGCTTCGATG    TCGGCCCGCA    ACCGGACACC    TATCTAAAGA    CGCACATGGC 11410         11420         11430         11440         11450         11460
CTACAACGCG    CGCCTGACCC    GCGGCTACGT    ACGATACACC    CTGTCACCGA    AAGCGCGCTT
GATGTTGCGC    GCGGACTGGG    CGCCGATGCA    TGCTATGTGG    GACAGTGGCT    TTCGCGCGAA 11470         11480         11490         11500         11510         11520
GCCCGCAAAA    GCAGAGGGTT    GGCTGGTGTC    ACTAGACAGA    TTCATCGTGC    AGTACCTCAA
CGGGCGTTTT    CGTCTCCCAA    CCGACCACAG    TGATCTGTCT    AAGTAGCACG    TCATGGAGTT 11530         11540         11550         11560         11570         11580
CACATTGCTG    ATTACAATGA    TGGCGGCGAT    ATGGGCTCGC    GTTTTGATAA    CCTACCTGGT
GTGTAACGAC    TAATGTTACT    ACCGCCGCTA    TACCCGAGCG    CAAAACTATT    GGATGGACCA

UL148  11600         11610         11620         11630         11640
GTCGCGGCGT    CGGTAGAGGC    TTGCGGAAAC    CACGTCCCTG    TCACACGTCG    TTGCGGACA
CAGCGCCGCA    GCCATCTCCG    AACGCCTTTG    GTGCAGGAC    AGTGTGCAGC    AAGCGCCTGT 11650         11660         11670    UL132  11680         11690         11700
TAGCAAGAAA    TCCACGTCGC    CACATCTCGA    GAATGCCGGC    CTTGCGGGGT    CCCCTTCGCG
ATCGTTCTTT    AGGTGCAGCG    GTGTAGAGCT    CTTACGGCCG    GAACGCCCCA    GGGGAAGCGC 11710         11720         11730         11740         11750         11760
CAACATTCCT    GGCCCTGGTC    GCGTTCGGGT    TGCTGCTTCA    GATAGACCTC    AGCGACGCTA
GTTGTAAGGA    CCGGGACCAG    CGCAAGCCCA    ACGACGAAGT    CTATCTGGAG    TCGCTGCGAT 11770         11780         11790         11800         11810         11820
CGAATGTGAC    CAGCAGCACA    AAAGTCCCTA    CTAGCACCAG    CAACAGAAAT    AACGTCGACA
GCTTACACTG    GTCGTCGTGT    TTTCAGGGAT    GATCGTGGTC    GTTGTCTTTA    TTGCAGCTGT
```

FIG._1M-1

```
        11830              11840              11850              11860              11870              11880
ACGCCACGAG         TAGCGGACCCC        ACAACCGGGA         TCAACATGAC         CACCACCCAC         GAGTCTTCCG
TGCGGTGCTC         ATCGCCTGGG         TGTTGGCCCT         AGTTGTACTG         GTGGTGGGTG         CTCAGAAGGC 11890              11900              11910              11920              11930              11940
TTCACAACGT         GCGCAATAAC         GAGATCATGA         AAGTGCTGGC         TATCCTCTTC         TACATCGTGA
AAGTGTTGCA         CGCGTTATTG         CTCTAGTACT         TTCACGACCG         ATAGGAGAAG         ATGTAGCACT 11950              11960              11970              11980              11990              12000
CAGGCACCTC         CATTTTCAGC         TTCATAGCGG         TACTGATCGC         GGTAGTTTAC         TCCTCGTGTT
GTCCGTGGAG         GTAAAAGTCG         AAGTATCGCC         ATGACTAGCG         CCATCAAATG         AGGAGCACAA 12010              12020              12030              12040              12050              12060
GCAAGCACCC         GGGCCGCTTT         CGTTTCGCCG         ACGAAGAGGC         CGTCAACCTG         TTGGACGACA
CGTTCGTGGG         CCCGGCGAAA        GCAAAGCGGC         TGCTTCTCCG         GCAGTTGGAC         AACCTGCTGT 12070              12080              12090              12100              12110              12120
CGGACGACAG         TGGGCGGCAGC         AGCCCGTTTG         GCAGCGGGTTC        CCGACGAGGT         TCTCAGATCC
GCCTGCTGTC         ACCGCCGTCG         TCGGGCAAAC         CGTCGCCAAG         GGCTGCTCCA         AGAGTCTAGG 12130              12140              12150              12160              12170              12180
CCGCCGGATT         TTGTTCCTCG         AGCCCTTATC         AGCGGTTGGA         AACTCGGGAC         TGGGACGAGG
GGCGGCCTAA         AACAAGGAGC         TCGGGAATAG         TCGCCAACCT         TTGAGCCCTG         ACCCTGCTCC 12190              12200              12210              12220              12230              12240
AGGAGGAGGC         GTCCGCGGCC         CGCGAGCGCA         TGAAACATGA         TCCTGAGAAC         GTCATCTATT
TCCTCCTCCG         CAGGCGCCGG         GCGCTCGCGT         ACTTTGTACT         AGGACTCTTG         CAGTAGATAA 12250              12260              12270              12280              12290              12300
TCAGAAAGGA         TGGCAACTTG         GACACGTCGT         TCGTGAATCC         CAATTATGGG         AGAGGCTCGC
AGTCTTTCCT         ACCGTTGAAC         CTGTGCAGCA         AGCACTTAGG         GTTAATACCC         TCTCCGAGCG
```

FIG._1M-2

```
       12310      12320      12330      12340      12350      12360
CTTTGACCAT CGAATCTCAC CTCTCGGACA ATGAGGAGGA CCCCATCAGG TACTACGTTT
GAAACTGGTA GCTTAGAGTG GAGAGCCTGT TACTCCTCCT GGGGTAGTCC ATGATGCAAA 12370      12380      12390      12400      12410      12420
CGGTGTACGA TGAACTGACC GCCTCGGAAA TGGAAGAACC TTCGAACAGC ACCAGCTGGC
GCCACATGCT ACTTGACTGG CGGAGCCTTT ACCTTCTTGG AAGCTTGTCG TGGTCGACCG 12430      12440      12450      12460      12470      12480
AGATTCCCAA ACTAATGAAA GTTGCCATGC AACCCGTCTC GCTCAGAGAT CCCGAGTACG
TCTAAGGGTT TGATTACTTT CAACGGTACG TTGGGCAGAG CGAGTCTCTA GGGCTCATGC

UL132  12490      12500      12510      12520      12530      12540
ACTAG̲GCTTT TTTTTTTGTC TTTCGGTTCC AACTCTTTCC CCGCCCCATC ACCTCGCCTG
TGATC̲CGAAA AAAAAAACAG AAAGCCAAGG TTGAGAAAGG GGCGGGGTAG TGGAGCGGAC 12550      12560      12570      12580      12590      12600
TACTATGTGT ATGATGTCTC ATAATAAAGC TTTCTTTCTC AGTCTGCAAC ATGCAGCTGT
ATGATACACA TACTACAGAG TATTATTTCG AAAGAAAGAG TCAGACGTTG TACGTCGACA 12610      12620      12630      12640      12650      12660
GTCGGGTGTG GCTGTCTGTT TGTCTGTGCG CCGTGGTGCT GGGTCAGTGC CAGCGGGAAA
CAGCCCACAC CGACAGACAA ACAGACACGC GGCACCACGA CCCAGTCACG GTCGCCCTTT 12670      12680      12690      12700      12710      12720
CCGCGGAAAA AAACGATTAT TACCGAGTAC CGCATTACTG GGACGCGTGC TCTCGCGCGC
GGCGCCTTTT TTTGCTAATA ATGGCTCATG GCGTAATGAC CCTGCGCACG AGAGCGCGCG 12730      12740      12750      12760      12770      12780
TGCCCGACCA AACCCGTTAC AAGTATGTGG AACAGCTCGT GGACCTCACG TTGAACTACC
ACGGGCTGGT TTGGGCAATG TTCATACACC TTGTCGAGCA CCTGGAGTGC AACTTGATGG
```

FIG. _1N-1_

```
        12790            12800            12810            12820            12830            12840
ACTACGATGC GAGCCACGGC TTGGACAACT TTGACGTGCT CAAGAGGTGA GGGTACGCGC
TGATGCTACG CTCGGTGCCG AACCTGTTGA AACTGCACGA GTTCTCCACT CCCATGCGCG 12850            12860            12870            12880            12890            12900
TAAAGTGCA  TGACAACGGG AAGGTAAGGG CGAACGGGTA ACGGCTAAGT AACCGCATGG
ATTTCCACGT ACTGTTGCCC TTCCATTCCC GCTTGCCCAT TGCCGATTCA TTGGCGTACC 12910            12920            12930            12940            12950            12960
GGTATGAAAT GACGTTTGGA ACCTGTGCTT GCAGAATCAA CGTGACCGAG GTGTCGTTGC
CCATACTTTA CTGCAAACCT TGGACACGAA CGTCTTAGTT GCACTGGCTC CACAGCAACG 12970            12980            12990            13000            13010            13020
TCATCAGCGA CTTTAGACGT CAGAACCGTC GCGGCGGCAC CAACAAAAGG ACCACGTTCA
AGTAGTCGCT GAAATCTGCA GTCTTGGCAG CGCCGCCGTG GTTGTTTTCC TGGTGCAAGT 13030            13040            13050            13060            13070            13080
ACGCCGCCGG TTCGCTGGCG CCACACGCCC GGAGCCTTCGA GTTCAGCCGTG CGGCTCTTTG
TGCGGCGGCC AAGCGACCGC GGTGTGCGGG CCTCGGAGCT CAAGTCGCAC GCCGAGAAAC 13090            13100      UL130  13110            13120            13130            13140
CCAACTAGCC TGCGTCACGG GAAATAATAT GCTGCGGCTT CTGCTTCGTC ACCACTTTCA
GGTTGATCGG ACGCAGTGCC CTTTATTATA CGACGCCGAA GACGAAGCAG TGGTGAAAGT 13150            13160            13170            13180            13190            13200
CTGCCTGCTT CTGTGCGCGG TTTGGGCAAC GCCCTGTCTG GCGTCTCCGT GGTCGACGCT
GACGGACGAA GACACGCGCC AAACCCGTTG CGGGACAGAC CGCAGAGGCA CCAGCTGCGA
```

```
       13210      13220      13230      13240      13250      13260
  AACGGCAAAC CAGAATCCGT CCCCGCCATG GTCTAAACTG ACGTATTCCA AACCGCATGA
  TTGCCGTTTG GTCTTAGGCA GGGGCGGTAC CAGATTTGAC TGCATAAGGT TTGGCGTACT 13270      13280      13290      13300      13310      13320
  CGCGGCGACG TTTTACTGTC CTTTTCTCTA TCCCTCGCCC CCACGGTCCC CCTTGCAATT
  GCGCCGCTGC AAAATGACAG GAAAAGAGAT AGGGAGCGGG GGTGCCAGGG GGAACGTTAA 13330      13340      13350      13360      13370      13380
  CTCGGGGTTC CAGCAGGTAT CAACGGGTCC CGAGTGTCGC AACGAGACCC TGTATCTGCT
  GAGCCCCAAG GTCGTCCATA GTTGCCCAGG GCTCACAGCG TTGCTCTGGG ACATAGACGA 13390      13400      13410      13420      13430      13440
  GTACAACCGG GAAGGCCAGA CCTTGGTGGA GAGAAGCTCC ACCTGGGTGA AAAAGGTGAT
  CATGTTGGCC CTTCCGGTCT GGAACCACCT CTCTTCGAGG TGGACCCACT TTTTCCACTA 13450      13460      13470      13480      13490      13500
  CTGGTATCTG AGCGGTCGCA ACCAGACCAT CCTCCAACGG ATGCCCCAAA CGGCTTCGAA
  GACCATAGAC TCGCCAGCGT TGGTCTGGTA GGAGGTTGCC TACGGGGTTT GCCGAAGCTT 13510      13520      13530      13540      13550      13560
  ACCGAGCGAC GGAAACGTGC AGATCAGCGT GGAAGACGCC AAGATTTTTG GAGCGCACAT
  TGGCTCGCTG CCTTTGCACG TCTAGTCGCA CCTTCTGCGG TTCTAAAAAC CTCGCGTGTA 13570      13580      13590      13600      13610      13620
  GGTGCCCAAG CAGACCAAGC TGCTACGCTT CGTCGTCAAC GATGGCACGC GTTATCAGAT
  CCACGGGTTC GTCTGGTTCG ACGATGCGAA GCAGCAGTTG CTACCGTGCG CAATAGTCTA 13630      13640      13650      13660      13670      13680
  GTGTGTGATG AAGCTGGAGA GCTGGGCCCA CGTCTTCCGG GACTACAGCG TGTCTTTTCA
  CACACACTAC TTCGACCTCT CGACCCGGGT GCAGAAGGCC CTGATGTCGC ACAGAAAAGT
```

FIG._10-1

```
       13690               13700               13710               13720               13730               13740
GGTGCGATTG          ACGTTCACCG          AGGCCAATAA          CCAGACTTAC          ACCTTCTGTA          CCCATCCCAA
CCACGCTAAC          TGCAAGTGGC          TCCGGTTATT          GGTCTGAATG          TGGAAGACAT          GGGTAGGGTT

13750 UL130        13760               13770               13780               13790               13800
TCTCATCATT          TGAGCCCGTC          GCGCGCGCAG          GGAATTTGA           AAACCGCGCG          TCATGAGTCC
AGAGTAGTAA          ACTCGGGGCAG         CGCGCGCGTC          CCTTAAAAACT         TTTGGCGCGC          AGTACTCAGG 13810               13820               13830               13840               13850               13860
CAAAGACCTG          ACGCCGTTCT          TGACGACGTT          GTGGCTGCTA          TTGGGTCACA          GCCGCGTGCC
GTTTCTGGAC          TGCGGCAAGA          ACTGCTGCAA          CACCGACGAT          AACCCAGTGT          CGGCGCACGG 13870               13880               13890               13900               13910               13920
GCGGGTGCGC          GCAGAAGAAT          GTTGCGAATT          CATAAACGTC          AACCACCCGC          CGGAACGCTG
CGCCACGCG           CGTCTTCTTA          CAACGCTTAA          GTATTTGCAG          TTGGTGGGCG          GCCTTGCGAC 13930               13940               13950               13960               13970               13980
TTACGATTTC          AAAATGTGCA          ATCGCTTCAC          CGTCGCGTAC          GTATTTTCAT          GATTGTCTGC
AATGCTAAAG          TTTTACACGT          TAGCGAAGTG          GCAGCGCATG          CATAAAAGTA          CTAACAGACG 13990               14000               14010               14020               14030               14040
GTTCTGTGGT          GCGTCTGGAT          TTGTCTCTCG          ACGTTTCTGA          TAGCCATGTT          CCATCGACGA
CAAGACACCA          CGCAGACCTA          AACAGAGAGC          TGCAAAGACT          ATCGGTACAA          GGTAGCTGCT 14050               14060               14070               14080               14090               14100
TCCTCGGGAA          TGCCAGAGTA          GATTTTCATG          AATCCACAGG          CTGCCGTGTC          CGGACGGCGA
AGGAGCCCTT          ACGGTCTCAT          CTAAAAGTAC          TTAGGTGTCC          GACGCCACAG          GCCTGCCGCT 14110               14120               14130               14140               14150               14160
AGTCTGCTAC          AGTCCCGAGA          AAACGGCTGA          GATTCGCGGG          ATCGTCACCA          CCATGACCCA
TCAGACGATG          TCAGGGCTCT          TTTGCCGACT          CTAAGCGCCC          TAGCAGTGGT          GGTACTGGGT
```

*FIG._10-2*

```
        14170      14180      14190      14200      14210      14220
TTCATTGACA CGCCAGGTCG TACACAACAA ACTGACGAGC TGCAACTACA ATCCGTAAGT
AAGTAACTGT GCGGTCCAGC ATGTGTTGTT TGACTGCTCG ACGTTGATGT TAGGCATTCA 14230      14240      14250      14260      14270      14280
CTCTTCCTCG AGGGCCTTAC AGCCTATGGG AGAGTAAGAC AGAGAGGGAC AAAACATCAT
GAGAAGGAGC TCCCGGAATG TCGGATACCC TCTCATTCTG TCTCTCCCTG TTTTGTAGTA 14290      14300      14310      14320      14330      14340
TAAAAAAAAA AGTCTAATTT CACGTTTTGT ACCCCCCTTC CCCTCCGTGT TGTAGCCCAT
ATTTTTTTTT TCAGATTAAA GTGCAAAACA TGGGGGAAG GGGAGGCACA ACATCGGGTA 14350      14360      14370      14380      14390      14400
CGGCCGCGGC GATCTCCTAG TAACACTCGT CCGACACTTC CACCATCTCC AGCTCGGCCG
GCCGGCGCCG CTAGAGGATC ATTGTGAGCA GGCTGTGAAG GTGGTAGAGG TCGAGCCGGC 14410      14420      14430      14440      14450      14460
GCGGTTCGGC ATCCTCTACC AGCGGGGTCG TCTCATCTTT GCCGCAGCAG CGGACGCACA
CGCCAAGCCG TAGGAGATGG TCGCCGCAGC AGAGTAGAAA CGGCGTCGTC GCCTGCGTGT 14470      14480      14490      14500      14510      14520
CCTTCTCCAG GCAGAACGCC ACCAGCTGCC GCCGAACGTA CCACAGGTAC ACGTGCAGAC
GGAAGAGGTC CGTCTTGCGG TGGTCGACGG CGGCTTGCAT GGTGTCCATG TGCACGTCTG 14530      14540      14550      14560      14570      14580
CTGCGAACAG GACTACGGAG GTCATGACCA CCACGACGCA CACGGGAATC CAGGGATCGA
GACGCTTGTC CTGATGCCTC CAGTACTGGT GGTGCTGCGT GTGCCCTTAG GTCCCTAGCT 14590      14600      14610      14620      14630      14640
GATTGTTGCT GGAACTCATG GCTATCGCCA CCGACGTGCC CGGCGTCTGT TCACCGCCGC
CTAACAACGA CCTTGAGTAC CGATAGCGGT GGCTGCACGG GCCGCAGACAG AGTGGCGGCG
```

```
14650       14660       14670       14680       14690       14700
TCGCCCGATG  TCGCGCGGCT  TGTTATACGC  TAGCCCGTCG  CCGCCTCGGG  GCACGGTGCC
AGCGGGCTAC  AGCGCGCCGA  ACAATATGCG  ATCGGGCAGC  GGCGGAGCCC  CGTGCCACGG 14710       14720       14730       14740       14750       14760
CTCCTACCCA  CGTAACTTCC  TCCGTGACTT  AAAGTCGCGT  GTGGTAGATC  TCCTGCTCCG
GAGGATGGGT  GCATTGAAGG  AGGCACTGAA  TTTCAGCGCA  CACCATCTAG  AGGACGAGGC 14770       14780       14790       14800       14810       14820
TGGACGAACC  GTCCGGCAGG  ATAGCGGTTA  AGGATTCGGT  GCTAAGGCCG  TGTCGCCAAC
ACCTGCTTGG  CAGGCCGTCC  TATCGCCAAT  TCCTAAGCCA  CGATTCCGGC  ACAGCGGTTG 14830       14840       14850       14860       14870       14880
GTCGAATGCT  ACGTTGCAAC  AGCTTCGACG  GACGGCCATC  CCCTCTCTCA  TCGCAATAAT
CAGCTTACGA  TGCAACGTTG  TCGAAGCTGC  CTGCCGGTAG  GGGAGAGAGT  AGCGTTATTA 14890       14900       14910       14920       14930       14940
AAAACACCAG  CAGCGCGCAC  GACGCGATCA  CGGTGACACC  CATGATTAGA  CCCACGCAGA
TTTTGTGGTC  GTCGCGCGTG  CTGCGCTAGT  GCCACTGTGG  GTACTAATCT  GGGTGCGTCT 14950       14960       14970       14980       14990       15000
TAGCCAGCCC  CGCTAGCGTA  TCTAGCGCCA  TCCCGTTCGC  TCCCGTTGTC  TCCTGAGCGA
ATCGGTCGGG  GCGATCGCAT  AGATCGCGGT  AGGGCAAGCG  AGGGCAACAG  AGGACTCGCT 15010       15020       15030       15040       15050       15060
AGCAACTTCT  CGGTCCCCGT  TTTCAACAGT  TTTTGTTTCC  TTCTCCGCGA  CTAGATGTTA
TCGTTGAAGA  GCCAGGGGCA  AAAGTTGTCA  AAAACAAAGG  AAGAGGCGCT  GATCTACAAT 15070       15080       15090       15100       15110       15120
ACGCCCGCGG  TCTTTCCGGC  CGTGCTCTAC  CTCCTGGCGC  TTGTCGTCTG  GGTTGAGATG
TGCGGGCGCC  AGAAAGGCCG  GCACGAGATG  GAGGACCGCG  AACAGCAGAC  CCAACTCTAC
```

FIG._1P-2

```
         15130                 15140       15150           15160           15170           15180
TTCTGCCTCG   TCGCCGTAGC   CGTCGTCGAG   CGCGAGATCG   CCTGGGCGCT   GCTGCTGCGG
AAGACGGAGC   AGCGGCATCG   GCAGCAGCTC   GCGCTCTAGC   GGACCCGCGA   CGACGACGCC 15190                 15200       15210           15220           15230           15240
ATGCTGGTCG   TTGGCCTGAT   GGTGGAAGTC   GGCGCCGCCG   CCGCTTGGAC   CTTCGTGCGT
TACGACCAGC   AACCGGACTA   CCACCTTCAG   CCGCGGCGGC   GGCGAACCTG   GAAGCACGCA 15250                 15260       15270           15280           15290           15300
TGTCTTGCCT   ATCAGCGCTC   CTTCCCCGTG   CTTACGGCCT   TCCCCTGAAA   CCCACGTTAA
ACAGAACGGA   TAGTCGCGAG   GAAGGGGCAC   GAATGCCGGA   AGGGGACTTT   GGGTGCAATT 15310                 15320       15330           15340           15350           15360
CCGACCGTCC   CAAAAACGCC   GGTGTTAACA   CAGGAAAAAA   AGAAACCACG   CAGGAACCGC
GGCTGGCAGG   GTTTTTGCGG   CCACAATTGT   GTCCTTTTTT   TCTTTGGTGC   GTCCTTGGCG 15370                 15380       15390           15400           15410           15420
GCAGGAACCA   CGCGGAACAT   GGGACACTAT   CTGGAAATCC   TGTTCAACGT   CATCGTCTTC
CGTCCTTGGT   GCGCCTTGTA   CCCTGTGATA   GACCTTTAGG   ACAAGTTGCA   GTAGCAGAAG 15430                 15440       15450           15460           15470           15480
ACTCTGCTGC   TCGGCGTCAT   GGTCAGTATC   GTCGCTTGGT   ACTTCACGTG   AACCACCGTC
TGAGACGACG   AGCCGCAGTA   CCAGTCATAG   CAGGAACCA   TGAAGTGCAC   TTGGTGGCAG 15490                 15500       15510           15520           15530           15540
GTCCCGGTTT   AAAAACCATC   GTTATAAAGC   CACCCGGACA   CACCCGGACA   CGCCGCCGG
CAGGGCCAAA   TTTTTGGTAG   CAATATTTCG   GTGGGCCTGT   GTGGGCCTGT   GCGCGGCGCC 15550                 15560       15570           15580           15590           15600
CACTTGCCTA   CGGCGTCGCT   TCAGGGAAAC   TCCTCTTCCT   TCTGCTCTTC   CTCCTTCACC
GTGAACGGAT   GCCGCGACGA   AGTCCCTTTG   AGGAGAAGGA   AGACGAGAAG   GAGGAAGTGG
```

*FIG._1Q-1*

```
15610       15620       15630       15640       15650       15660
GCAGGGATCG  TTTCCCTCGA  CCAGGGACTC  GCCGAAGCAA  CCGCCGGAGC  AACCTGGAGG
CGTCCCTAGC  AAAGGGAGCT  GGTCCCTGAG  CGGCTTCGTT  GGCGGCCTCG  TTGGACCTCC 15670       15680       15690       15700       15710       15720
AGTCGCGGCA  TGACGGCGCC  CAAGTGTGTC  ACCACCAGTA  CTTATCTGGT  CAAGACCAAG
TCAGCGCCGT  ACTGCCGCGG  GTTCACACAG  TGGTGGTCAT  GAATAGACCA  GTTCTGGTTC 15730       15740       15750       15760 UL149 15770       15780
GAACAGCCCT  GGTGGCCCGA  CAACGCCATC  AGGAGATGGT  GGATCAGTGT  TGCTATCGTC
CTTGTCGGGA  CCACCGGGCT  GTTGCGGTAG  TCCTCTACCA  CCTAGTCACA  ACGATAGCAG 15790       15800       15810       15820       15830       15840
ATCTTCATCG  GAGTCTGTCT  GGTGGCCCTG  ATGTACTTTA  CGCAGCAGCA  GGCACGCAGC
TAGAAGTAGC  CTCAGACAGA  CCACCGGGAC  TACATGAAAT  GCGTCGTCGT  CCGTGCGTCG 15850       15860       15870  UL150 15880      15890       15900
GGGAGCAGCA  GCGGCTAGAC  AAGTCTCTGG  CGGCTACAGC  TCCAAGCGCC  GTAGCCGGGC
CCCTCGTCGT  CGCCGATCTG  TTCAGAGACC  GCCGATGTCG  AGGTTCGCGG  CATCGGCCCG 15910       15920       15930       15940       15950       15960
CGCCTGCCGA  TCGCGACGTC  GTGGACCATC  GAACAGAGAC  TCACGCGTAC  GAGACCCCGA
GCGGACGGCT  AGCGCTGCAG  CACCTGGTAG  CTTGTCTCTG  AGTGCGCATG  CTCTGGGGCT 15970       15980       15990       16000       16010       16020
GGTACGCCAC  GCGGTGCCTA  ACGCGGTATA  CCACACCCGT  ACGGTCTGCA  GTGCGGCGTA
CCATGCGGTG  CGCCACGGAT  TGCGCCATAT  GGTGTGGGCA  TGCCAGACGT  CACGCCGCAT 16030       16040       16050       16060       16070       16080
CAACGTGTGG  GCGTCGCAGA  GTCCGCCACG  TTCCTGTCTT  GTCGCTCCCC
GTTGCACACC  CGCAGCGTCT  CAGGCGGTGC  AAGGACAGAA  CAGCGAGGGG
AAAACGCGTT
TTTTGCGCAA
```

*FIG.__1Q-2*

```
         16090                 16100                 16110                          16120 UL149   16130                16140
AATCGTCTCC     CGCACACCCC     CCGCGACACC     CAGAGGGGCGG     GTGAGCCAAG     TATTCTTAAG
TTAGCAGAGG     GCGTGTGGGG     GGCGCTGTGG     GTCTCCCGCC     CACTCGGTTC     ATAAGAATTC 16150                 16160                 16170                 16180                 16190                 16200
GCCGTTCTTT     GTTCCATAGC     CCATAAATTG     TTGATTCCGG     AGCTCGTTGG     CGCGGAAATA
CGGCAAGAAA     CAAGGTATCG     GGTATTTAAC     AACTAAGGCC     TCGAGCAACC     GCGCCTTTAT 16210                 16220                 16230                 16240                 16250                 16260
GCCGGATAAG     GGGAGCAACA     ACCGTTGGCG     AAAGCCGTCC     CGCTCATTCA     GTCCGGGTTT
CGGCCTATTC     CCCTCGTTGT     TGGCAACCGC     TTTCGGCAGG     GCGAGTAAGT     CAGGCCCAAA 16270                 16280                 16290                 16300                 16310                 16320
CGCGTCCAGT     CGGACGTGTG     ACCGTTGGGC     AACGGAACGG     CGTTTCACTG     CCAAAATCGT
GCGCAGGTCA     GCCTGCACAC     TGGCAACCCG     TTGCCCTTGC     GCAAAGTGAC     GGTTTTAGCA 16330                 16340                 16350                 16360                 16370                 16380
ATCGGGTAGT     GTACGAGACG     TCGGCGGTGC     AGAATGCGAC     TCGCGGCGTA     GCTCGCCGTC
TAGCCCATCA     CATGCTCTGC     AGCCGCCACG     TCTTACGCTG     AGCGCCGCAT     CGAGCGGCAG 16390                 16400                 16410                 16420                 16430                 16440
GCTATGCGGC     TCGTCGCCGC     GTGGCGGCGC     CTGGCCGGCT     GTCTGCGTCC     AGATCTGTTG
CGATACGCCG     AGCAGCGGCA     CACCGCGCCG     GACCGGCCGA     CAGACGCAGG     TCTAGACAAC 16450                 16460                 16470                 16480                 16490                 16500
GCCTTTTGGT     TCCTCTCGGCT     GCTGCTGCCT     GTGTGCTTTG     GTAGACGCGG     TGGCAGTTTG
CGGAAAACCA     AGGAGACCGA     CGACGACGCA     CACACGAAAC     CATCTGCGCC     ACCGTCAAAC 16510                 16520                 16530                 16540                 16550                 16560
CGGTCTGCGG     TAAGTGAGGA     TGTCGCCGAG     CAAACGCACT     TGCGGCCGCGT     GGGCGGCACG
GCCAGACGCC     ATTCACTCCT     ACAGCGGCTC     GTTTGCGTGA     ACGCCGCGCA     CCCGCCGTGC
```

FIG._1R-1

```
       16570                16580                16590                16600                16610                16620
CGTGTCATTG   TAGGTTCGTT   GCCAGATGGC   AAGTGCTGTC   AACAGCAGGC   GTTGTGGGCG
GCACAGTAAC   ATCCAAGCAA   CGGTCTACCG   TTCACGACAG   TTGTCGTCCG   CAACACCCGC 16630                16640                16650                16660                16670                16680
GTCGGTGTAT   TTTTGTGGGT   TGCGGTGAGA   GTCGGCACTC   GGTGTTTTGT   GAGTCATCTC
CAGCCACATA   AAAACACCCA   ACGCCACTCT   CAGCCGTGAG   CCACAAAACA   CTCAGTAGAG 16690                16700                16710                16720                16730                16740
AACTATCTGT   GTTGCTTTGA   GCAGCGTCCA   GAACAGCGAC   GCGACTTTGG   GGATGGCCTC
TTGATAGACA   CAACGAAACT   CGTCGCAGGT   CTTGTCGCTG   CGCTGAAACC   CCTACCGGAG 16750                16760                16770                16780                16790                16800
GTGCTCACCT   CCGCGGAGAG   CGCCGCCGGA   CCTGCTCGTC   AGCAGCGAGC   TACGCAGACG
CACGAGTGGA   GGCGCCTCTC   GCGGCGGCCT   GGACGAGCAG   TCGTCGCTCG   ATGCGTCTGC 16810                16820                16830                16840                16850                16860
GAATATCTGG   AGGAGAGTTA   CGTGTGTCAC   AGGAGAGCGC   GGGTCTCCGG   CGGTAACGAC
CTTATAGACC   TCCTCTCAAT   GCACACAGTG   TCCTCTCGCG   CCCAGAGGCC   GCCATTGCTG 16870                16880                16890                16900                16910                16920
GGCGGTGTCG   TCGACACGTG   TGCGGCCTGT   TGTGCTCTGC   GGAAAAGTGC   CGGTCTCGGA
CCGCCACAGC   AGCTGTGCAC   ACGCCGGACA   ACACGAGACG   CCTTTTCACG   GCCAGAGCCT 16930                16940                16950                16960                16970                16980
GACCGTGGAC   GAAAAAGAGA   ACGCAGCAGC   TACCGCTGGC   GGCGGCGGCG   TTAATGCAGC
CTGGCACCTG   CTTTTTCTCT   TGCGTCGTCG   ATGGCGACCG   CCGCCGCCGC   AATTACGTCG
```

*FIG.\_1R-2*

```
                  16990       17000       17010       17020       17030       17040
CGTTGATGTT   CGACGTTGTG   AGCACTCGGA   AACAGCGGTG   AGGCAGAAGG   TCGATTCTCC
GCAACTACAA   GCTGCAACAC   TCGTGAGCCT   TTGTCGCCAC   TCCGTCTTCC   AGCTAAGAGG 17050       17060       17070       17080       17090       17100
AGGGAACGAC   AGTCGATGCG   TGGTAGCCGC   AGCAGGTGAG   GTTGGGGCGG   ACAACGTGTT
TCCCTTGCTG   TCAGCTACGC   ACCATCGGCG   TCGTCCACTC   CAACCCCGCC   TGTTGCACAA 17110       17120       17130       17140       17150       17160
GCGGATTGTG   GCGAGAACGT   CGTCCCTCCC   TTCTTCACCG   CCCCACCCAC   CCTCGGTTGG
CGCCTAACAC   CGCTCTTGCA   GCAGGAGGGG   AAGAAGTGGC   GGGGTGGGTG   GGAGCCAACC 17170       17180       17190       17200       17210       17220
TGTTTCTTTT   TTCTTGTGTC   CTGCAGATAG   TTCCACGGAC   AGCGACGGCA   AGTCCATAAT
ACAAAGAAAA   AAGAACACAG   GACGTCTATC   AAGGTGCCTG   TCGCTGCCGT   TCAGGTATTA 17230       17240       17250       17260       17270       17280
CAGCGGGTGTG  CAAGTGGTGG   AACACGACGA   AGATATCATC   GCGCCGCAGA   GTTGTGGTG
GTCGCCACAC   GTTCCACCAC   TTGTGCTGCT   TCTATAGTAG   CGCGGCGTCT   CAAACACCAC

17290 UL151  17300       17310       17320       17330       17340
CACGGCGTTC   AAGGAAGCCC   TCTGGGATGT   GGCTCTGTTG   GAAGTGCCGC   GTTGGGCGTG
GTGCCGCAAG   TTCCTTCGGG   AGACCCTACA   CCGAGACAAC   CTTCACGGCG   CAACCCGCAC 17350       17360       17370       17380       17390       17400
GCAGGGCTGG   AAGAGGTGGC   GCAAACAGCA   GGCCGGGCGT   CGATGGAGTG   CTGGGTCTGC
CGTCCCGACC   TTCTCCACCG   CGTTGTCGCT   CCGGCCCGCA   GCTACCTCAC   GACCCAGACG 17410       17420       17430       17440       17450       17460
GTCGGCTTCC   AGCTTGTCTG   ACTTGGCGGG   CGAGGCCGTT   GGAGAATTGG   TGGGATCGGT
CAGCCGAAGG   TCGAACAGAC   TGAACCGCCC   GCTCCGGCAA   CCTCTTAACC   ACCCTAGCCA
```

*FIG._1S-1*

|  |  |  |  |  |  |
|---|---|---|---|---|---|
| 17470 | 17480 | 17490 | 17500 | 17510 | 17520 |
| CGTCGCGTAC | GTGATCCTTG | AACGTCTGTG | GTTGGCAGCC | AGAGGTTGGG | TGTGCGAAAC |
| GCAGCGCATG | CACTAGGAAC | TTGCAGACAC | CAACCGTCGG | TCTCCAACCC | ACACGCTTTG |
| 17530 | 17540 | 17550 | 17560 | 17570 | 17580 |
| AGGTGTGGAA | GCCGAGGAGG | CCATGTCGCG | GCGGCGACAG | CGCATGCTGT | GGCGTATTGT |
| TCCACACCTT | CGGCTCCTCC | GGTACAGCGC | CGCCGCTGTC | GCGTACGACA | CCGCATAACA |
| 17590 | 17600 | 17610 | 17620 | 17630 | 17640 |
| TCTCTCGTGG | AGGCGACGGC | GAATGCAGCA | GACGGTGTTC | GATGGAGATG | GCGTGCGGGG |
| AGAGACACC | TCCGCTGCCG | CTTACGTCGT | CTGCCACAAG | CTACCTCTAC | CGCACGCCCC |
| 17650 | 17660 | 17670 | 17680 | 17690 | 17700 |
| AAGAAAGCGC | CGTGTTGTGA | GCAGACGACG | TAGGATGCGG | GACGTCGGAG | CACATGGGCC |
| TTCTTTCGCG | GCACAACACT | CGTCTGCTGC | ATCCTACGCC | CTGCAGCCTC | GTGTACCCGG |
| 17710 | 17720 | 17730 | 17740 | 17750 | 17760 |
| ATGTGTGGTG | GCAGATGGCG | GTGTCCGCTG | GTGTCTGCTG | CGGCAGTGCA | TAGACGAAGC |
| TACACCAC | CGTCTACCGC | CACAGGCGAC | CACAGACGAC | GCCGTCACGT | ATCTGCTTCG |
| 17770 | 17780 | 17790 | 17800 | UL150 17810 | 17820 |
| AACATGTCGC | TGTGAAGAGA | TAGAGTGTGA | GCATAGCTGC | ATGCAGCGTT | GCGTGTATAA |
| TTGTACAGCG | ACACTTCTCT | ATCTCACACT | CGTATCGACG | TACGTCGCAA | CGCACATATT |
| 17830 | 17840 | 17850 | 17860 | 17870 | 17880 |
| GCGGSGGGGA | TTAAGACGTT | AATAAAGAAT | AGCGGCGGTT | CTGATAGGGC | GACCGCTGAA |
| CGCCCCCCT | AATTCTGCAA | TTATTTCTTA | TCGCCGCCAA | GACTATCCCG | CTGGCGACTT |
| 17890 | 17900 | 17910 | 17920 | 17930 | 17940 |
| GTGAGCTGCG | TGTGCGTGTG | GTTTGTGGAG | TCCCCGCCCC | CCCGGTCCC | GTGTCCGCCG |
| CACTCGACGC | ACACGCACAC | CAAACACCTC | AGGGGCGGGG | GGGCCAGGG | CACAGGCGGC |

*FIG._1S-2*

```
       17950              17960              17970              17980              17990              18000
GCAAAGCCCC         CCGGNTCCGC         ACACTCCTGG         CCGCGCAACC         CTCGTCGCTG         CAAAAGCCCC
CGTTTCGGGG         GGCCNAGGCG         TGTGAGGACC         GGCGCGTTGG         GAGCAGCGAC         GTTTTCGGGG 18010              18020              18030              18040              18050              18060
CCGTCCCCGC         ACACCCCGC          GACCGCGGT          CCCGCGAGTC         CCCGTCCCCG         CCGCAAAAGG
GGCAGGGGCG         TGTGGGGGCG         CTGGCGGCCA         GGGCGCTCAG         GGGCAGGGGC         GGCGTTTTCC 18070              18080              18090              18100              18110              18120
CCCCGTCCT          CGCCGCAAAC         ACCCCCGTCA         CCCCCGTCCC         TCAGNCCCGGG        TCCGCGAGTC
GGGGCAGGA          GCGGCGTTTG         TGGGGGCAGT         GGGGGCAGGG         AGTCNGGCCC         AGGCGCTCAG 18130              18140              18150              18160              18170              18180
CCCGTTCCCA         GCGTAATCCC        CGTACCCGCA          ACGNCCCGGN         CCCACCGTCG         TCCCGCACAC
GGGCAAGGGT         CGCATTAGGG        GCATGGGCGT          TGCNGGGCCN         GGGTGGCAGC         AGGGCGTGTG 18190              18200              18210              18220              18230              18240
CCCCGTCCC          CCAGCCCGGT         GCCCAGCGTG         CGAAAAAAGC         TCCGTCCCTC         ACACCCGCAG
GGGGCAGGG          GGTCGGGCCA         CGGGTCGCAC         GCTTTTTTCG         AGGCAGGGAG         TGTGGGCGTC 18250              18260              18270              18280              18290              18300
AAAGATCCCT         CAGCGCGGTG         CCCAGCCCGTC        CCCAGCGCCG         TGCCGCTGAC         AAAGACCATG
TTTCTAGGGA         GTCGCGCCAC         GGGTCGGGCAG        GGGTCGCGGC         ACGGCGACTG         TTTCTGTAC
                                                                                               ▼UL151

18310              18320              18330              18340              18350              18360
GGACGACACG         CACAGGCA..         ..........         ..........         ..........         ..........
CCTGCTGTGC         GTGTCCGT..         ..........         ..........         ..........         ..........
```

```
         10         20         30         40         50         60
ATCGGGCGCC AGAGCTAGAT CAGGCGTATC AAATTCCACT GCCAGGCGAC CTGATTCTAA
TAGCCCGCGG TCTCGATCTA GTCCGCATAG TTTAAGGTGA CGGTCCGCTG GACTAAGATT 70         80         90        100        110        120
CGGTTCCACG ATCCGGGAGA GCGTTTCTAG ATATAGAGCA AAGCGTACCA CGTCTACCTG
GCCAAGGTGC TAGGCCCTCT CGCAAAGATC TATATCTCGT TTCGCATGGT GCAGATGGAC 130        140        150        160        170        180
CGGTGTAAAA AACTGTGTGT GGCGTTCACC GTCGTTGACC ACGTAAGCCA CGTAGAGGCC
GCCACATTTT TTGACACACA CCGCAAGTGG CAGCAACTGG TGCATTCGGT GCATCTCCGG 190        200        210        220        230        240
AACATTTTCC ACCACGGGTT CTAGCTGCAG GCGGCACGTA AAGCTTAGAA ACGACGGCTG
TTGTAAAAGG TGGTGCCCAA GATCGACGTC CGCCGTGCAT TTCGAATCTT TGCTGCCGAC 250        260        270        280        290        300
TACGGTTTGG TTCCCGTGAA GCTGAAGCGT CACTTCCTTG CCGGGGCTCA CCGTGCTGTA
ATGCCAAACC AAGGGCACTT CGACTTCGCA GTGAAGGAAC GGCCCCGAGT GGCACGACAT 310        320        330        340        350        360
ACGCCGCACC GAGTCGGTCA TCTGCTCCAG ATCGGTAGAC CAGAAGGGCG TGCAATGCAT
TGCGGCGTGG CTCAGCCAGT AGACGAGGTC TAGCCATCTG GTCTTCCCGC ACGTTACGTA 370        380        390        400        410        420
ACTGTCCCAG TCGCGACACG CAGCCCAGCC TAGCTCGGTG AAGGGTCGAC GCACACCCGA
TGACAGGGTC AGCGCTGTGC GTCGGGTCGG ATCGAGCCAC TTCCCAGCTG CGTGTGGGCT 430        440        450        460        470        480
AAAAGTGTGC TTGAAGACCA GGGGGTCGCC TCGGTAGCTC AGTAGCCGAA CATGCACATA
TTTTCACACG AACTTCTGGT CCCCCAGCGG AGCCATCGAG TCATCGGCTT GTACGTGTAT
```

```
        490        500        510        520        530        540
GTCGCGGCTA CGTTGACAGA CGGCCCGTAG ACAGGCAGGA CAAGCGTGAA CAGCAAGCGC
CAGCGCCGAT GCAACTGTCT GCCGGGCATC TGTCCGTCCT GTTCGCACTT GTCGTTCGCG 550        560        570        580        590        600
AACATGCTGC GGGTTAGAAA ATGCGGCGTG CCGGCCACCG CCCGACTCAT AAACGCTACC
TTGTACGACG CCCAATCTTT TACGCCGCAC GGCCGGTGGC GGGCTGAGTA TTTGCGATGG 610        620        630        640        650        660
AGCATGACGT CTCAGATCAC ACAAGTGACG AGGAGCGTAC CGCAAATCAC TAGGGAAAAG
TCGTACTGCA GAGTCTAGTG TGTTCACTGC TCCTCGCATG GCGTTTAGTG ATCCCTTTTC 670        680        690        700        710        720
GCCAGCAGAG CCCGATAGTC TTGCTCTTCG CGAACGATCT CGTCCGGTTC CTCGCAGTCT
CGGTCGTCTC GGGCTATCAG AACGAGAAGC GCTTGCTAGA GCAGGCCAAG GAGCGTCAGA 730        740        750        760        770        780
TCGTGGTCCA CAGAAGATGA GGAGCAGGAT TCTTCGTTAA TTTCTGCCAG GATACTAGTG
AGCACCAGGT GTCTTCTACT CCTCGTCCTA AGAAGCAATT AAAGACGGTC CTATGATCAC 790        800        810        820        830        840
CTGTACCACA CCAGAGCGCT CAGCGGTGCCC AGGGCTACCG CACGGTAAAA TAGGGACATG
GACATGGTGT GGTCTCGCGA GTCGCACGGG TCCCGATGGC GTGCCATTTT ATCCCTGTAC

UL147 850        860        870        880        890        900
ATCACCAGCG CAATCTGAAG TGGTGGTAGT TCAGTTTCTT GGCGTATTTC CAGAGAAAGG
TAGTGGTCGC GTTAGACTTC ACCACCATCA AGTCAAAGAA CCGCATAAAG GTCTCTTTCC 910        920        930        940        950        960
CTTTGTAGGC CGTAGGGACT GGCCAGGCAC CGAACTCAAT ATTGGTAGAC ACTACGTCGT
GAAACATCCG GCATCCCTGA CCGGTCCGTG GCTTGAGTTA TAACCATCTG TGATGCAGCA
```

*FIG._2A-2*

```
                                970         980         990        1000        1010        1020
                         AAATGCGTTG  TTCCTCGTCT  AAGATTAACC  GAAAAAATAG  CCGGTTGATG  TGACGACGCA
                         TTTACGCAAC  AAGGAGCAGA  TTCTAATTGG  CTTTTTTATC  GGCCAACTAC  ACTGCTGCGT 1030        1040        1050        1060        1070        1080
                         CGGCTTGCGC  GTTAGGATTG  AGACACTTGG  TGCCCTTGTC  CTTTAAAATA  GCCAGCACTT
                         GCCGAACGCG  CAATCCTAAC  TCTGTGAACC  ACGGGAACAG  GAAATTTTAT  CGGTCGTGAA 1090        1100        1110        1120        1130        1140
                         CCTGACGATT  GCAGCTTTCG  CTCGCCGCGA  TTGGCTTAAG  CAATTCAGTT  CCGATTGGCA
                         GGACTGCTAA  CGTCGAAAGC  GAGCGGCGCT  AACCGAATTC  GTTAAGTCAA  GGCTAACCGT 1150        1160        1170        1180        1190        1200
                         GAGTATTCAA  CAGAATTTGG  TTGTTACAAC  GACAGCGTTT  GTCGTAATCT  TCCAATTCTA
                         CTCATAAGTT  GTCTTAAACC  AACAATGTTG  CTGTCGCAAA  CAGCATTAGA  AGGTTAAGAT 1210        1220        1230        1240        1250        1260
                         AAAGATGGAC  GGCTAGGGGA  CATACGACAA  ATAACATGTA  TGCAGTCAAT  TGCATATATC
                         TTTCTACCTG  CCGATCCCCT  GTATGCTGTT  TATTGTACAT  ACGTCAGTTA  ACGTATATAG 1270        1280        1290        1300        1310        1320
                         GTACCGATAA  AATGTTAGTG  TGCGGATTCA  GAATCGGATG  ATGCAACCGT  CTTAGCATCA
                         CATGGCTATT  TTACAATCAC  ACGCCTAAGT  CTTAGCCTAC  TACGTTGGCA  GAATCGTAGT 1330        1340        1350        1360        1370        1380
                    ┌──  TATCGAAAAA  GTATACATAT  TACCGATTCA  TTATAATTAG  GGAA TTATT  CCAACGCGGA
                    │    ATAGCTTTTT  CATATGTATA  ATGGCTAAGT  AATATTAATC  CCTT AATAAA GGTTGCGCCT
              UL147 │                                                          UL152 ◄────
                    ▼          1390        1400        1410        1420   1430        1440
                         CGTTGTTAG  TGACAGCGTT  TTCTTCTACA  TGCGGTCCAT  TACTATCCTT  TACTTTTACC
                         GCAAACAATC  ACTGTCGCAA  AAGAAGATGT  ACGCCAGGTA  ATGATAGGAA  ATGAAAATGG
```

FIG._2B-1

```
     1450               1460               1470               1480               1490               1500
AATACTCTGT         GCCATGAGTT         GTCTTTTTTA         CCATCCAGCC         ATTTGGACAA         ATGATGATCG
TTATGAGACA         CGGTACTCAA         CAGAAAAAAT         GGTAGGTCGG         TAAACCTGTT         TACTACTAGC 1510               1520               1530               1540               1550               1560
GGAGCTAAAC         ATACAGGTTT         ACCTCGAGGA         GGCAATAGAT         AATGTTGAGG         TTTGTCACAC
CCTCGATTTG         TATGTCCAAA         TGGAGCTCCT         CCGTTATCTA         TTACAACTCC         AAACAGTGTG 1570               1580               1590               1600               1610               1620
TCAGGAGGAT         TGGGAGGGTC         ACGACCAACC         CAAAATAAGC         CACCTATAGG         ATGATGTAAA
AGTCCTCCTA         ACCCTCCCAG         TGCTGGTTGG         GTTTTATTCG         GTGGATATCC         TACTACATTT 1630               1640               1650               1660               1670               1680
GCTTTGTGGG         TACACGGACA         ACGCAATTCT         CTACTGTGAA         CCCCATGGTA         ATACATAAAT
CGAAACACCC         ATGTGCCTGT         TGCGTTAAGA         GATGACACTT         GGGGTACCAT         TATGTATTTA 1690               1700          UL152  1720               1730               1740
GCCATCAAAA         GACTAAATCAG         ATTAATCGCA         TTCTAATTTT         ATTAACTACG
CGGTAGTTTT         CTGATTAGTC         TAATTAGCGT         AAGATTAAAA         TAATTGATGC 1750               1760               1770               1780               1790               1800
TCACTATCAG         TAATTCGTAA         TATCCGGTAT         TCCCGGAAAA         TCACTCAAAA         CTGCGTCCAT
AGTGATAGTC         ATTAAGCATT         ATAGGCCATA         AGGGCCTTTT         AGTGAGTTTT         GACGCAGGTA 1810               1820               1830               1840               1850               1860
GACACATCAA         TTCCCGATAA         GTACCCCCCT         TTGAAATCGG         ATCCCCCCAC         ATACCAATCA
CTGTGTAGTT         AAGGGCTATT         CATGGGGGGA         AACTTTAGCC         TAGGGGGGTG         TATGGTTAGT
```

*FIG._2B-2*

```
         1870       1880       1890       1900       1910       1920
   ATCACACAAC ACACAGGTTT AAAAATCGAT CACACGTCAA TTAGGTTTCA AAATCGATAC
   TAGTGTGTTG TGTGTCCAAA TTTTTAGCTA GTGTGCAGTT AATCCAAAGT TTTAGCTATG 1930       1940       1950       1960       1970       1980
   TGTTTATTAT CAGGAATCTA GACTAATTCT ACAATGACAG CTCTGAATTT CTCTCTCGTC
   ACAAATAATA GTCCTTAGAT CTGATTAAGA TGTTACTGTC GAGACTTAAA GAGAGAGCAG 1990       2000       2010       2020       2030       2040
   TTTCTTGTCA GGTTCTCATC ATCAATCTTC ACTTCCACCC ATCGAGGAGT CATCGTCGCT
   AAAGAACAGT CCAAGAGTAG TAGTTAGAAG TGAAGGTGGG TAGCTCCTCA GTAGCAGCGA 2050       2060       2070       2080       2090       2100
   CCAAAACCCT TTGGGGTCGC TGGTTGGAAA AGTCTCTGAC ACGATCCAGG CACCCCGTAC
   GGTTTTGGGA AACCCCAGCG ACCAACCTTT TCAGAGACTG TGCTAGGTCC GTGGGGCATG 2110       2120       2130       2140       2150       2160
   CCAGTCCGAC TGATCTAGCT TACGGAGCAT CTCAACAGGC ATGAGCTGCA GGGCCACGGC
   GGTCAGGCTG ACTAGATCGA ATGCCTCGTA GAGTTGTCCG TACTCGACGT CCCGGTGCCG 2170       2180       2190       2200       2210       2220
   TGTCACGGCA GGGATTATTA CTACCGTTCA GGTAAACTGT ATCTCCCTGA GTTACCGTGA
   ACAGTGCCGT CCCTAATAAT GATGGCAAGT CCATTTGACA TAGAGGGACT CAATGGCACT 2230       2240       2250       2260       2270       2280
   TGGGTCTTTC TACATGTTGA CTTTGCGTAA AAAATCGCCG GTAAAATGTT TTTTCTTGTT
   ACCCAGAAAG ATGTACAACT GAAACGCATT TTTTAGCGGC CATTTTACAA AAAAGAACAA 2290       2300       2310       2320       2330       2340
   CATGTAAAAG TACCGGAACT AAAATGCTAG TTAGAATGGT TGCAGTTGCT ATTAGCGCGG
   GTACATTTTC ATGGCCTTGA TTTTACGATC AATCTTACCA ACGTCAACGA TAATCGCGCC
```

FIG._2C-1

```
     2350           2360           2370           2380           2390           2400
CTAGTAACAG     TAGTTTAGTG     TTACATTGTA     TACCCATGTT     TTTAATAACT     ATGAATATTC
GATCATTGTC     ATCAAATCAC     AATGTAACAT     ATGGGTACAA     AAATTATTGA     TACTTATAAG 2410           2420           2430           2440           2450           2460
TGCTTCACAC     CATAAGTGCT     TAACCCACAA     AAACCACACG     GAGACATTAT     TGGCTAARAA
ACGAAGTGTG     GTATTCACGA     ATTGGGTGTT     TTTGGTGTGC     CTCTGTAATA     ACCGATTTTT 2470           2480           2490           2500     UL153 2510           2520
TAAAAACAAA     AGTTTATTGA     TGTGCATGTT     AGGTTTTAGT     CTAAAATTCA     TCTGGGTCGT
ATTTTGTTT      TCAAAATACT     ACACGTACAA     TCCAAAATCA     GATTTTAAGT     AGACCCAGCA
                                                                  ▼

2530           2540           2550           2560           2570           2580
ATTTGGGAAG     TTTTGTATAA     CGCGGTCTTC     TGGGGACGCG     ACGGCTACCC     ATGTATAAGG
TAAACCCTTC     AAAACATATT     GCGCCAGAAG     ACCCCTGCGC     TGCCGATGGG     TACATATTCC 2590           2600           2610           2620           2630           2640
CTATAAGTGC     CACAGATACC     ACTATACCCG     CCCATACAGC     ATGAATTCCC     AGGGGAATGT
GATATTCACG     GTGTCTATGG     TGATATGGGC     GGGTATGTCG     TACTTAAGGG     TCCCCTTACA 2650           2660           2670           2680           2690           2700
ATTTTGTTTT     ATTACATTGT     CCCACGTTCT     GCTATTATGC     TGGTCTGATT
TAGTGTTTTT     TAATGTAACA     GGGTGCAAGA     CGATAATACG     ACCAGACTAA
ATCACAAAAA     ATGTCAAAAT 2710           2720           2730           2740           2750           2760
CCTCTTTTGT     TTTACATTTA     TCAGGTATAG     GAGACGATGT     TGCAGTTCCT     GATAACACGG
GGAGAAAACA     AAATGTAAAT     AGTCCATATC     CTCTGCTACA     ACGTCAAGGA     CTATTGTGCC 2770           2780           2790           2800           2810           2820
TTAAATAGTA     GTTTTCCTTT     TTACCGTCAC     TGTAACGTTG     CAAAACGTAT     TTTCCAGCGT
AATTTATCAT     CAAAAGGAAA     AATGGCAGTG     ACATTGCAAC     GTTTGCATA     AAAGGTCGCA
```

FIG._2C-2

```
2830       2840       2850       2860       2870       2880
GTTCGGTAGT TACGTTGTAT ATAGTGAGAG AGGTCTTATT GCAGTCTAAA CACATGCCGT
CAAGCCATCA ATGCAACATA TATCACTCTC TCCAGAATAA CGTCAGATTT GTGTACGGCA 2890       2900       2910       2920       2930       2940
TCAGTGGGGA AGTTGAATAA TAATGTCCAA TGCTGCACAG TTGGTGTGCG CGAGGTCCAT
AGTCACCCCT TCAACTTATT ATTACAGGTT ACGACGTGTC AACCACACGC GCTCCAGGTA 2950       2960       2970       2980       2990       3000
ATTTTATCCA TTCTATATCG TGCCATACAT CCGTTCTACT GCAGTTTTTC AAAGTGACGT
TAAAATAGGT AAGATATAGC ACGGTATGTA GGCAAGATGA CGTCAAAAAG TTTCACTGCA 3010       3020       3030       3040       3050       3060
ATCCACCGAC ATATCCTGTT ACATTAATTA CTTCGTAATT TAAATTAGAG TGTTTATAAA
TAGGTGGCTG TATAGGACAA TGTAATTAAT GAAGCATTAA ATTTAATCTC ACAAATATTT 3070       3080       3090       3100       3110       3120
CGGTGTACAA ACTGCCATTG CAAGTTATGT TGCTGGTATT CAACCAGGGA GTAGTACTAT
GCCACATGTT TGACGGTAAC GTTCAATACA ACGACCATAA GTTGGTCCCT CATCATGATA 3130       3140       3150       3160       3170       3180
GAATGGTAGA AAACGTTAAT GTTGGCGTAG CGCTTGACGA TGATTTTGAA AGCCGTTGAAG
CTTACCATCT TTTGCAATTA CAACCGCATC GCGAACTGCT ACTAAAACTT TCGCAACTTC 3190       3200       3210       3220       3230       3240
TGGTTGCTGA TGCGACTGAA GAAGCGGTAG AGGGTTTGTG CGTGGTTCCA TTTGCGATAG
ACCAACGACT ACGCTGACTT CTTCGCCATC TCCCAAACAC GCACCAAGGT AAACGCTATC 3250       3260       3270       3280       3290       3300
CTGAAGTGCT GTTAGCCATCG GTGACAGAGT TAGAAGAATT TGTGATAGTG GAGGCGGTGG
GACTTCACGA CAATCGTAGC CACTGTCTCA ATCTTCTTAA ACACTATCAC CTCCGCCACC
```

*FIG. 2D-1*

```
3310 AATTGCACGG ACAGGAGCAC UL153 3340                          3360
AGGTAAAGGC                GTGTCATTGC AACCTTCAGA TATCGTAATC
TCCATTTCCG TTAACGTGCC TGTCCTCGTG CACAGTAACG TTGGAAGTCT ATAGCATTAG
                                              ↓

3370                3380       3390       3400       3410       3420
ATCAGTAACG TCCACTTAAC CGTAAATCTC CAGTCCATAA CGTTATTAAA TTTCGGTTAA
TAGTCATTGC AGGTGAATTG GCATTTAGAG GTCAGGTATT GCAATAATTT AAAGCCAATT 3430       3440       3450       3460       3470       3480
CGGGCATTGA TGTTTCTTCG GACGTTGTTG ATCTTTCTTG CCCGTTTATT TTCTGATATG
GCCCGTAACT ACAAAGAAGC CTGCAACAAC TAGAAAGAAC GGGCAAATAA AAGACTATAC 3490       3500       3510  UL154 3520      3530       3540
GTCTCATAAG ACATTTATCC GGAAACGTTG CTTAGTCCTC GTGCTCAGGA TTGTATCGAA
CAGAGTATTC TGTAAATAGG CCTTTGCAAC GAATCAGGAG CACGAGTCCT AACATAGCTT
                                 ↓

3550       3560       3570       3580       3590       3600
CTATGAATTC TGATTCACTT ATATCGTCAC TTAATGGATG ATATTTTTTA TTTAGAGCTC
GATACTTAAG ACTAAGTGAA TATAGCAGTG AATTACCTAC TATAAAAAAT AAATCTCGAG 3610       3620       3630       3640       3650       3660
GTCGGACGAA AAATAGGAGA ATGCAGGCTA CACAAATTAA TGCTAACGTC CACGTAGTGC
CAGCCTGCTT TTTATCCTCT TACGTCCGAT GTGTTTAATT ACGATTGCAG GTGCATCACG 3670       3680       3690       3700       3710       3720
GTCTGCCGTG TGATGTGTTA GAATGATTGT TATAGCGGTA TAAATGATCT ATAGATGATG
CAGACGGCAC ACTACACAAT CTTACTAACA ATATCGCCAT ATTTACTAGA TATCTACTAC 3730       3740       3750       3760       3770       3780
TGGCTGTATT GTCTTCATAA TTGGTCGGTT TATGAGAAGT GTCCCATTCG TGCTTTGGTT
ACCGACATAA CAGAAGTATT AACCAGCCAA ATACTCTTCA CAGGGTAAGC ACGAAACCAA
```

FIG._2D-2

```
3790        3800        3810        3820        3830        3840
CTTCACATAC  CCAGGGATTC  ACGTGTGTCC  CGTTTGTGTT  GTTTCTAGGA  TGTATTTGCA
GAAGTGTATG  GGTCCCTAAG  TGCACACAGG  GCAAACACAA  CAAAGATCCT  ACATAAACGT 3850        3860        3870        3880        3890        3900
GATTARAGTT  TTGATTTGT   TCGGAGGGAT  GCCCAGTTTT  ATAACATCGA  AAGCTATATT
CTAATTTCAA  AACTAAAACA  AGCCTCCCTA  CGGGTCAAAA  TATTGTAGCT  TTCGATATAA 3910        3920        3930        3940        3950        3960
TACCAGAAATG AGTAAAATTA  AGACCGTACA  GAGATAAAGA  TAAATTACGA  TCGCATGTAA
ATGGTCTTAC  TCATTTTAAT  TCTGGCATGT  CTCTATTTCT  ATTTAATGCT  AGCGTACATT 3970        3980        3990        4000        4010        4020
AACATAAATC  ATAGTGATGT  TTTAGATAAT  TTGTGTGCCA  CTCACATAGT  ATACGCGAAT
TTGTATTTAG  TATCACTACA  AAATCTATTA  AACACACGGT  GAGTGTATCA  TATGCGCTTA 4030        4040        4050        4060        4070        4080
GGAGGATTTT  CAATGAATGG  TTATGATATT  TTCCATTTCT  TATGTTGGGA  TGGGTGTATT
CCTCCTAAAA  GTTACTTACC  AATACTATAA  AAGGTAAAGA  ATACAACCCT  ACCCACATAA 4090        4100        4110        4120        4130        4140
TTCCGTGTGT  GGATATATTA  AAATGTCTAA  GCCAGGCTGT  TTTGTAGCAC  GATGTGATGG
AAGGCACACA  CCTATATAAT  TTTACAGATT  CGGTCCGACA  AAACATCGTG  CTACACTACC 4150        4160        4170        4180        4190        4200
TTAGGTTGTG  TGTTATAGTA  ATATTGTCTC  CTTGTGCCGC  CTCCAATAAT  GTTTCAGATT
AATCCAACAC  ACAATATCAT  TATAACAGAG  GAACACGGCG  GAGGTTATTA  CAAAGTCTAA 4210        4220        4230        4240        4250        4260
CTTTTGATAT  CGTATTATTT  GTACTGTTAG  GCGATGAGCA  AGTTGGAAGC  GGTGTAGTGA
GAAAACTATA  GCATAATAAA  CATGACAATC  CGCTACTCGT  TCAACCTTCG  CCACATCACT
```

*FIG. 2E-1*

```
      4270       4280       4290       4300       4310       4320
CGTTTTCATT TGCATTTATC ATAGTAGTAG TGTTGGTTGA TAATGATATA GTTTGCAAAG
GCAAAAGTAA ACGTAAATAG TATCATCATC ACAACCAACT ATTACTATAT CAAACGTTTC 4330       4340       4350       4360       4370       4380
TCACAGTACT ATCGGTTACA TGCTGTGTCG ATGAATTCGT GTCGCCGTTT GGTGAAGTTG
AGTGTCATGA TAGCCAATGT ACGACACAGC TACTTAAGCA CAGCGGCAAA CCACTTCAAC 4390       4400       4410       4420       4430       4440
TTATTACAGT TACGTTAGTT GTAGATGTTT GGGTAGATAT GGTGGAAATA GTTGAGGTCA
AATAATGTCA ATGCAATCAA CATCTACAAA CCCATCTATA CCACCTTTAT CAACTCCAGT 4450       4460       4470       4480       4490       4500
CGTCTGTGCC TTTTACAGAG CTTGCAGTGA ATCCCTGTGA TGTGTTGACG TTGCCATTGG
GCAGACACGG AAAATGTCTC GAACGTCACT TAGGACACCT ACACAACTGC AACGGTAACC 4510       4520       4530       4540       4550       4560
AGGATGTGAA CATAGTGGTA GACATTTCGG TGGTTTGTAA CGTAGATGTC AGTTGTGTAG
TCCTACACTT GTATCACCAT CTGTAAAGCC ACCAAACATT GCATCTACAG TCAACACATC 4570       4580       4590       4600       4610       4620
TAGATATTAA GCTTGTGGGT GTAATCGACG TGGAAGTATT GGCGATAGTG GTGTTGTTAC
ATCTATAATT CGAACACCCA CATTAGCTGC ACCTTCATAA CCGCTATCAC CACAACAATG 4630       4640       4650       4660       4670       4680
ACTTGCTTTT CTGCAGAATC CAAAAAATAA TAAACATGCA TATTATTTGC GTATATGATG
TGAACGAAAA GACGTCTTAG GTTTTTTATT ATTTGTACGT ATAATAAACG CATATACTAC 4690       4700       4710       4720       4730       4740
ACTTGTTCCA CCGTCGATGT TGTGTGCGCA ┌T........ .......... .......... ..
TGAACAAGGT GGCAGCTACA ACACACGCGT └A........
                                    ↓UL154
```

FIG._2E-2

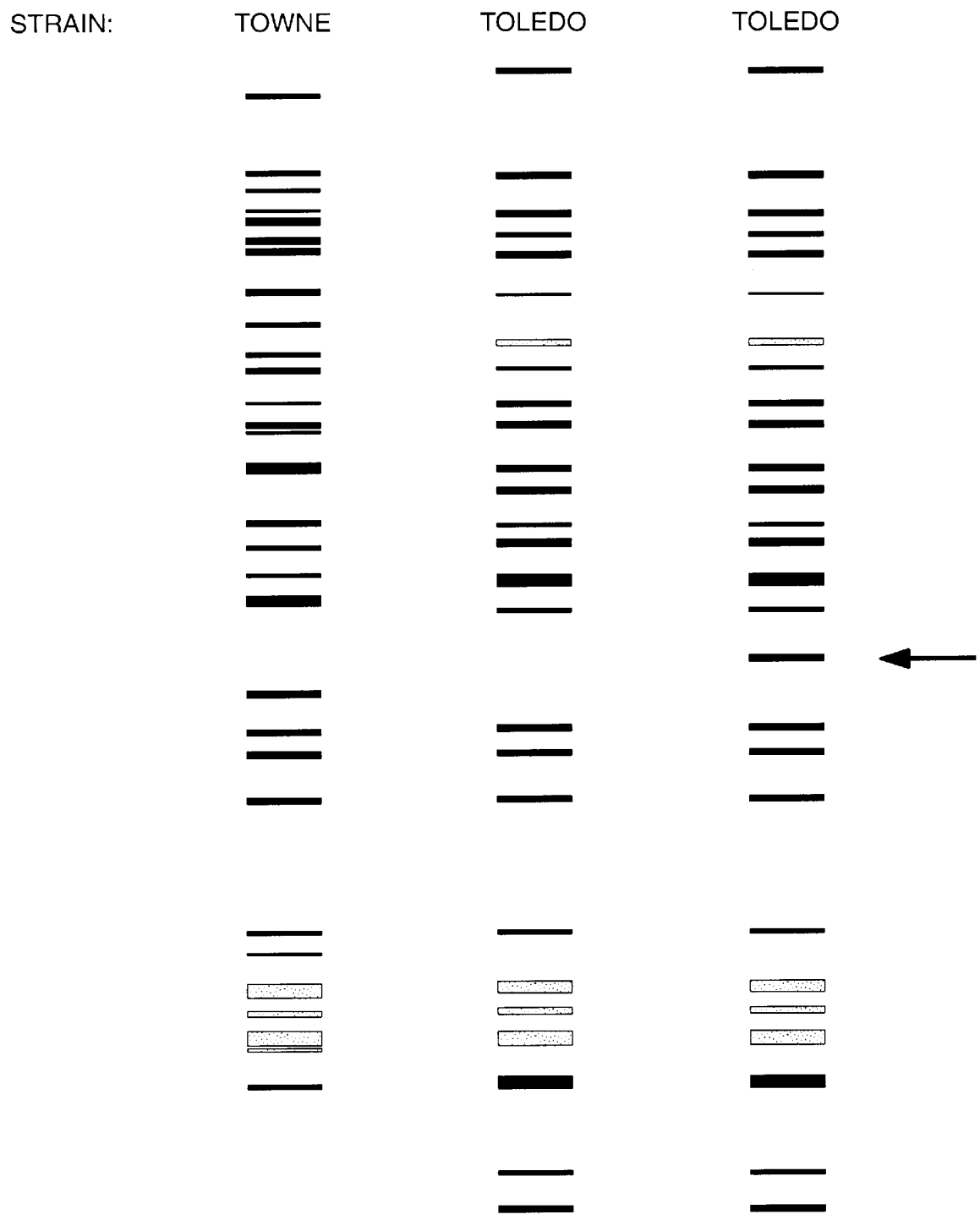
FIG._3

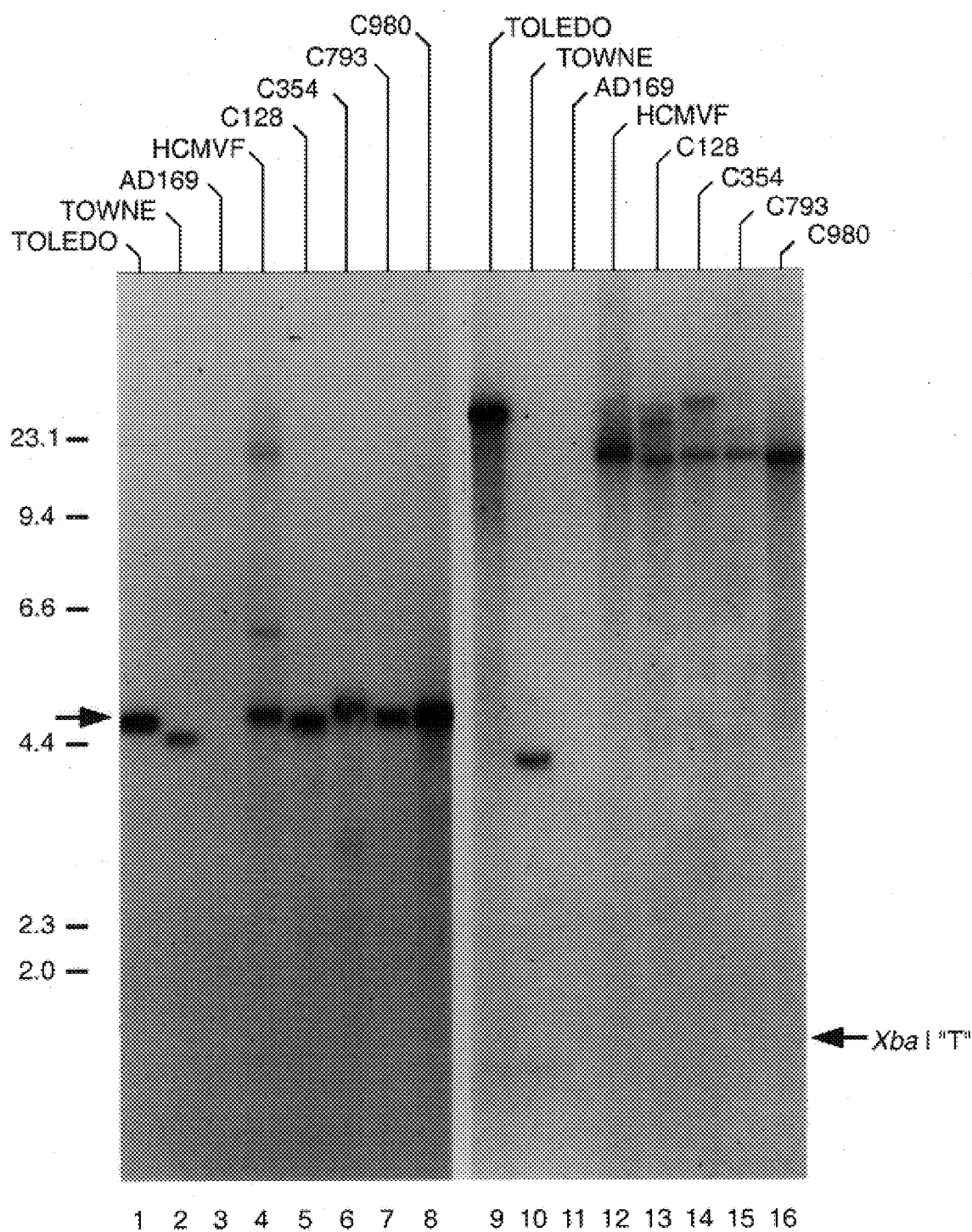
FIG._4

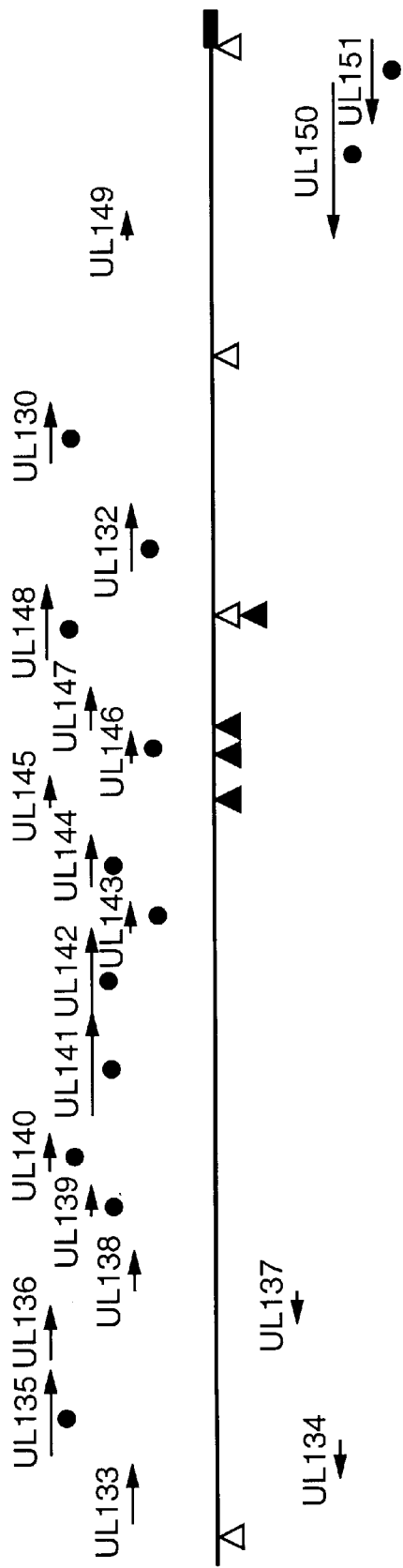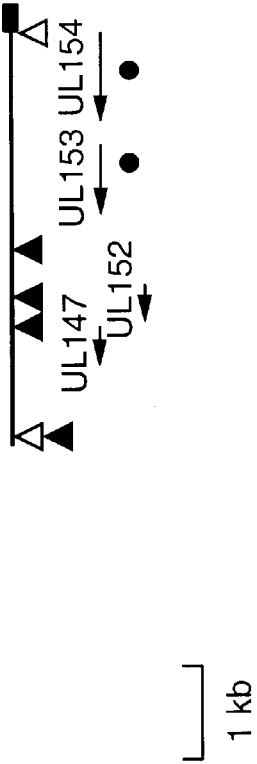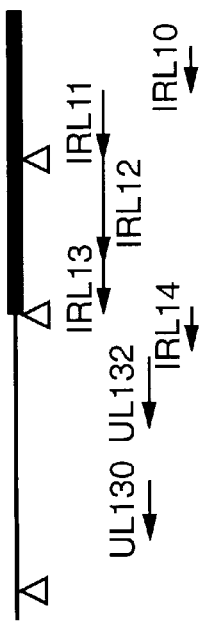
FIG._5

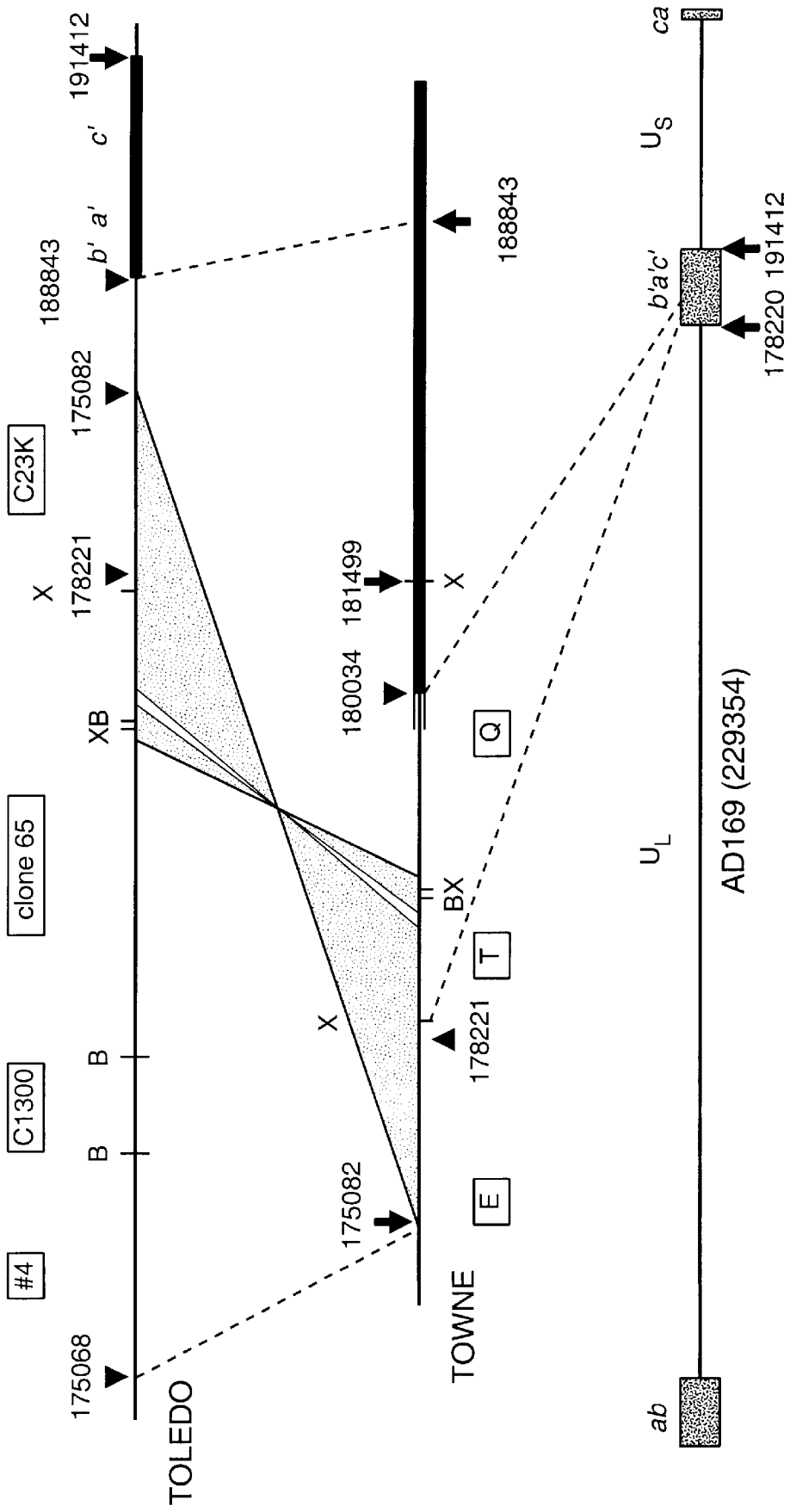
FIG._6

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 4711 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO

-continued (iv) ANTI-SENSE: NO (vi) ORIGINAL SOURCE:
    (A) ORGANISM: Human CMV
    (B) STRAIN: Towne (ix) FEATURE:
    (A) NAME/KEY: CDS
    (B) LOCATION: complement (845..1321)
    (D) OTHER INFORMATION: /product= "UL147"

(ix) FEATURE:
    (A) NAME/KEY: CDS
    (B) LOCATION: complement (1368..1721)
    (D) OTHER INFORMATION: /product= "UL152"

(ix) FEATURE:
    (A) NAME/KEY: CDS
    (B) LOCATION: complement (2504..3337)
    (D) OTHER INFORMATION: /product= "UL153"

(ix) FEATURE:
    (A) NAME/KEY: CDS
    (B) LOCATION: complement (3515..4711)
    (D) OTHER INFORMATION: /product= "UL154"

(xi) SEQUENCE DESCRIPTION: SEQ ID NO:1:

```
ATCGGGCGCC AGAGCTAGAT CAGGCGTATC AAATTCCACT GCCAGGCGAC CTGATTCTAA      60
CGGTTCCACG ATCGGGAGA GCGTTTCTAG ATATAGAGCA AAGCGTACCA CGTCTACCTG     120
CGGTGTAAAA AACTGTTGTG GGCGTTCACC GTCGTTGACC ACGTAAGCCA CGTAGAGGCC    180
AACATTTTCC ACCACGGGTT CTAGCTGCAG GCGGCACGTA AAGCTTAGAA ACGACGGCTG    240
TACGGTTTGG TTCCCGTGAA GCTGAAGCGT CACTTCCTTG CCGGGGCTCA CCGTGCTGTA    300
ACGCCGCACC GAGTCGGTCA TCTGCTCCAG ATCGGTAGAC CAGAAGGGCG TGCAATGCAT    360
ACTGTCCCAG TCGCGACACG CAGCCCAGCC TAGCTCGGTG AAGGGTCGAC GCACACCCGA    420
AAAAGTGTGC TTGAAGACCA GGGGGTCGCC TCGGTAGCTC AGTAGCCGAA CATGCACATA    480
GTCGCGGCTA CGTTGACAGA CGGCCCGTAG ACAGGCAGGA CAAGCGTGAA CAGCAAGCGC    540
AACATGCTGC GGGTTAGAAA ATGCGGCGTG CCGGCCACCG CCCGACTCAT AAACGCTACC    600
AGCATGACGT CTCAGATCAC ACAAGTGACG AGGAGCGTAC CGCAAATCAC TAGGGAAAAG    660
GCCAGCAGAG CCCGATAGTC TTGCTCTTCG CGAACGATCT CGTCCGGTTC CTCGCAGTCT    720
TCGTGGTCCA CAGAAGATGA GGAGCAGGAT TCTTCGTTAA TTTCTGCCAG GATACTAGTG    780
CTGTACCACA CCAGAGCGCT CAGCGTGCCC AGGGCTACCG CACGGTAAAA TAGGGACATG    840
ATCACCAGCG CAATCTGAAG TGGTGGTAGT TCAGTTTCTT GGCGTATTTC CAGAGAAAGG    900
CTTTGTAGGC CGTAGGGACT GGCCAGGCAC CGAACTCAAT ATTGGTAGAC ACTACGTCGT    960
AAATGCGTTG TTCCTCGTCT AAGATTAACC GAAAAAATAG CCGGTTGATG TGACGACGCA   1020
CGGCTTGCGC GTTAGGATTG AGACACTTGG TGCCCTTGTC CTTTAAAATA GCCAGCACTT   1080
CCTGACGATT GCAGCTTTCG CTCGCCGCGA TTGGCTTAAG CAATTCAGTT CCGATTGGCA   1140
GAGTATTCAA CAGAATTTGG TTGTTACAAC GACAGCGTTT GTCGTAATCT TCCAATTCTA   1200
AAAGATGGAC GGCTAGGGA CATACGACAA ATAACATGTA TGCAGTCAAT TGCATATATC    1260
GTACCGATAA AATGTTAGTG TGCGGATTCA GAATCGGATG ATGCAACCGT CTTAGCATCA   1320
TATCGAAAAA GTATACATAT TACCGATTCA TTATAATTAG GGAATTATTT CCAACGCGGA   1380
CGTTTGTTAG TGACAGCGTT TTCTTCTACA TGCGGTCCAT TACTATCCTT TACTTTTACC   1440
AATACTCTGT GCCATGAGTT GTCTTTTTTA CCATCCAGCC ATTTGGACAA ATGATGATCG   1500
GGAGCTAAAC ATACAGGTTT ACCTCGAGGA GGCAATAGAT AATGTTGAGG TTTGTCACAC   1560
```

```
TCAGGAGGAT TGGGAGGGTC ACGACCAACC CAAAATAAGC CACCTATAGG ATGATGTAAA      1620

GCTTTGTGGG TACACGGACA ACGCAATTCT CTACTGTGAA CCCCATGGTA ATACATAAAT      1680

GCCATCAAAA GACTAATCAG CGAACCAAAA ATTAATCGCA TTCTAATTTT ATTAACTACG      1740

TCACTATCAG TAATTCGTAA TATCCGGTAT TCCCGGAAAA TCACTCAAAA CTGCGTCCAT      1800

GACACATCAA TTCCCGATAA GTACCCCCCT TTGAAATCGG ATCCCCCCAC ATACCAATCA      1860

ATCACACAAC ACACAGGTTT AAAAATCGAT CACACGTCAA TTAGGTTTCA AAATCGATAC      1920

TGTTTATTAT CAGGAATCTA GACTAATTCT ACAATGACAG CTCTGAATTT CTCTCTCGTC      1980

TTTCTTGTCA GGTTCTCATC ATCAATCTTC ACTTCCACCC ATCGAGGAGT CATCGTCGCT      2040

CCAAAACCCT TTGGGGTCGC TGGTTGGAAA AGTCTCTGAC ACGATCCAGG CACCCCGTAC      2100

CCAGTCCGAC TGATCTAGCT TACGGAGCAT CTCAACAGGC ATGAGCTGCA GGGCCACGGC      2160

TGTCACGGCA GGGATTATTA CTACCGTTCA GGTAAACTGT ATCTCCCTGA GTTACCGTGA      2220

TGGGTCTTTC TACATGTTGA CTTTGCGTAA AAAATCGCCG GTAAAATGTT TTTTCTTGTT      2280

CATGTAAAAG TACCGGAACT AAAATGCTAG TTAGAATGGT TGCAGTTGCT ATTAGCGCGG      2340

CTAGTAACAG TAGTTTAGTG TTACATTGTA TACCCATGTT TTTAATAACT ATGAATATTC      2400

TGCTTCACAC CATAAGTGCT TAACCCACAA AAACCACACG GAGACATTAT TGGCTAAAAA      2460

TAAAAACAAA AGTTTATTGA TGTGCATGTT AGGTTTTAGT CTAAAATTCA TCTGGGTCGT      2520

ATTTGGGAAG TTTTGTATAA CGCGGTCTTC TGGGGACGCG ACGGCTACCC ATGTATAAGG      2580

CTATAAGTGC CACAGATACC ACTATACCCG CCCATACAGC ATGAATTCCC AGGGGAATGT      2640

TAGTGTTTTT TACAGTTTTT ATTACATTGT CCCACGTTCT GCTATTATGC TGGTCTGATT      2700

CCTCTTTTGT TTTACATTTA TCAGGTATAG GAGACGATGT TGCAGTTCCT GATAACACGG      2760

TTAAATAGTA GTTTTCCTTT TTACCGTCAC TGTAACGTTG CAAAACGTAT TTTCCAGCGT      2820

GTTCGGTAGT TACGTTGTAT ATAGTGAGAG AGGTCTTATT GCAGTCTAAA CACATGCCGT      2880

TCAGTGGGGA AGTTGAATAA TAATGTCCAA TGCTGCACAG TTGGTGTGCG CGAGGTCCAT      2940

ATTTTATCCA TTCTATATCG TGCCATACAT CCGTTCTACT GCAGTTTTTC AAAGTGACGT      3000

ATCCACCGAC ATATCCTGTT ACATTAATTA CTTCGTAATT TAAATTAGAG TGTTTATAAA      3060

CGGTGTACAA ACTGCCATTG CAAGTTATGT TGCTGGTATT CAACCAGGGA GTAGTACTAT      3120

GAATGGTAGA AAACGTTAAT GTTGGCGTAG CGCTTGACGA TGATTTTGAA AGCGTTGAAG      3180

TGGTTGCTGA TGCGACTGAA GAAGCGGTAG AGGGTTTGTG CGTGGTTCCA TTTGCGATAG      3240

CTGAAGTGCT GTTAGCATCG GTGACAGAGT TAGAAGAATT TGTGATAGTG GAGGCGGTGG      3300

AGGTAAAGGC AATTGCACGG ACAGGAGCAC GTGTCATTGC AACCTTCAGA TATCGTAATC      3360

ATCAGTAACG TCCACTTAAC CGTAAATCTC CAGTCCATAA CGTTATTAAA TTTCGGTTAA      3420

CGGGCATTGA TGTTTCTTCG GACGTTGTTG ATCTTTCTTG CCCGTTTATT TTCTGATATG      3480

GTCTCATAAG ACATTTATCC GGAAACGTTG CTTAGTCCTC GTGCTCAGGA TTGTATCGAA      3540

CTATGAATTC TGATTCACTT ATATCGTCAC TTAATGGATG ATATTTTTTA TTTAGAGCTC      3600

GTCGGACGAA AAATAGGAGA ATGCAGGCTA CACAAATTAA TGCTAACGTC CACGTAGTGC      3660

GTCTGCCGTG TGATGTGTTA GAATGATTGT TATAGCGGTA TAAATGATCT ATAGATGATG      3720

TGGCTGTATT GTCTTCATAA TTGGTCGGTT TATGAGAAGT GTCCCATTCG TGCTTTGGTT      3780

CTTCACATAC CCAGGGATTC ACGTGTGTCC CGTTTGTGTT GTTCTAGGA TGTATTTGCA       3840

GATTAAAGTT TTGATTTTGT TCGGAGGGAT GCCCAGTTTT ATAACATCGA AAGCTATATT      3900

TACCAGAATG AGTAAAATTA AGACCGTACA GAGATAAAGA TAAATTACGA TCGCATGTAA      3960
```

```
AACATAAATC ATAGTGATGT TTTAGATAAT TTGTGTGCCA CTCACATAGT ATACGCGAAT    4020

GGAGGATTTT CAATGAATGG TTATGATATT TTCCATTTCT TATGTTGGGA TGGGTGTATT    4080

TTCCGTGTGT GGATATATTA AAATGTCTAA GCCAGGCTGT TTTGTAGCAC GATGTGATGG    4140

TTAGGTTGTG TGTTATAGTA ATATTGTCTC CTTGTGCCGC CTCCAATAAT GTTTCAGATT    4200

CTTTTGATAT CGTATTATTT GTACTGTTAG GCGATGAGCA AGTTGGAAGC GGTGTAGTGA    4260

CGTTTTCATT TGCATTTATC ATAGTAGTAG TGTTGGTTGA TAATGATATA GTTTGCAAAG    4320

TCACAGTACT ATCGGTTACA TGCTGTGTCG ATGAATTCGT GTCGCCGTTT GGTGAAGTTG    4380

TTATTACAGT TACGTTAGTT GTAGATGTTT GGGTAGATAT GGTGGAAATA GTTGAGGTCA    4440

CGTCTGTGCC TTTTACAGAG CTTGCAGTGA ATCCTGTGGA TGTGTTGACG TTGCCATTGG    4500

AGGATGTGAA CATAGTGGTA GACATTTCGG TGGTTTGTAA CGTAGATGTC AGTTGTGTAG    4560

TAGATATTAA GCTTGTGGGT GTAATCGACG TGGAAGTATT GGCGATAGTG GTGTTGTTAC    4620

ACTTGCTTTT CTGCAGAATC CAAAAAATAA TAAACATGCA TATTATTTGC GTATATGATG    4680

ACTTGTTCCA CCGTCGATGT TGTGTGCGCA T                                   4711
```

(2) INFORMATION FOR SEQ ID NO:2:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO:2:

```
Met Met Leu Arg Arg Leu His His Pro Ile Leu Asn Pro His Thr Asn
 1               5                  10                  15

Ile Leu Ser Val Arg Tyr Met Gln Leu Thr Ala Tyr Met Leu Phe Val
             20                  25                  30

Val Cys Pro Leu Ala Val His Leu Leu Glu Leu Glu Asp Tyr Asp Lys
         35                  40                  45

Arg Cys Arg Cys Asn Asn Gln Ile Leu Leu Asn Thr Leu Pro Ile Gly
     50                  55                  60

Thr Glu Leu Leu Lys Pro Ile Ala Ala Ser Glu Ser Cys Asn Arg Gln
65                  70                  75                  80

Glu Val Leu Ala Ile Leu Lys Asp Lys Gly Thr Lys Cys Leu Asn Pro
                 85                  90                  95

Asn Ala Gln Ala Val Arg Arg His Ile Asn Arg Leu Phe Phe Arg Leu
            100                 105                 110

Ile Leu Asp Glu Glu Gln Arg Ile Tyr Asp Val Val Ser Thr Asn Ile
        115                 120                 125

Glu Phe Gly Ala Trp Pro Val Pro Thr Ala Tyr Lys Ala Phe Leu Trp
    130                 135                 140

Lys Tyr Ala Lys Lys Leu Asn Tyr His His Phe Arg Leu Arg Trp
145                 150                 155
```

(2) INFORMATION FOR SEQ ID NO:3:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:3:

```
Met Arg Leu Ile Phe Gly Ser Leu Ile Ser Leu Met Ala Phe Met
 1               5                  10                  15

Tyr Tyr His Gly Val His Ser Arg Glu Leu Arg Cys Pro Cys Thr His
            20                  25                  30

Lys Ala Leu His His Pro Ile Gly Gly Leu Phe Trp Val Gly Arg Asp
                35                  40                  45

Pro Pro Asn Pro Pro Glu Cys Asp Lys Pro Gln His Tyr Leu Leu Pro
 50                  55                  60

Pro Arg Gly Lys Pro Val Cys Leu Ala Pro Asp His His Leu Ser Lys
 65                  70                  75                  80

Trp Leu Asp Gly Lys Lys Asp Asn Ser Trp His Arg Val Leu Val Lys
                85                  90                  95

Val Lys Asp Ser Asn Gly Pro His Val Glu Glu Asn Ala Val Thr Asn
                100                 105                 110

Lys Arg Pro Arg Trp Lys
                115
```

(2) INFORMATION FOR SEQ ID NO:4:

(i) SEQUENCE CHARACTERISTICS:
      (A) LENGTH: 278 amino acids
      (B) TYPE: amino acid
      (D) TOPOLOGY: linear (ii) MOLECULE TYPE: protein (xi) SEQUENCE DESCRIPTION: SEQ ID NO:4:

```
Met Thr Arg Ala Pro Val Arg Ala Ile Ala Phe Thr Ser Thr Ala Ser
 1               5                  10                  15

Thr Ile Thr Asn Ser Ser Asn Ser Val Thr Asp Ala Asn Ser Thr Ser
                20                  25                  30

Ala Ile Ala Asn Gly Thr Thr His Lys Pro Ser Thr Ala Ser Ser Val
                35                  40                  45

Ala Ser Ala Thr Thr Ser Thr Leu Ser Lys Ser Ser Ser Ala Thr
 50                  55                  60

Pro Thr Leu Thr Phe Ser Thr Ile His Ser Thr Thr Pro Trp Leu Asn
 65                  70                  75                  80

Thr Ser Asn Ile Thr Cys Asn Gly Ser Leu Tyr Thr Val Tyr Lys His
                85                  90                  95

Ser Asn Leu Asn Tyr Glu Val Ile Asn Val Thr Gly Tyr Val Gly Gly
                100                 105                 110

Tyr Val Thr Leu Lys Asn Cys Ser Arg Thr Asp Val Trp His Asp Ile
                115                 120                 125

Glu Trp Ile Lys Tyr Gly Pro Arg Ala His Gln Leu Cys Ser Ile Gly
                130                 135                 140

His Tyr Tyr Ser Thr Ser Pro Leu Asn Gly Met Cys Leu Asp Cys Asn
145                 150                 155                 160

Lys Thr Ser Leu Thr Ile Tyr Asn Val Thr Glu His Ala Gly Lys
                165                 170                 175

Tyr Val Leu Gln Arg Tyr Ser Asp Gly Lys Lys Glu Asn Tyr Tyr Leu
                180                 185                 190

Thr Val Leu Ser Gly Thr Ala Thr Ser Ser Pro Ile Pro Asp Lys Cys
                195                 200                 205

Lys Thr Lys Glu Glu Ser Asp Gln His Asn Ser Arg Thr Trp Asp Asn
                210                 215                 220
```

```
Val Ile Lys Thr Val Lys Asn Thr Asn Ile Pro Leu Gly Ile His Ala
225                 230                 235                 240

Val Trp Ala Gly Ile Val Val Ser Val Ala Leu Ile Ala Leu Tyr Met
            245                 250                 255

Gly Ser Arg Arg Val Pro Arg Arg Pro Arg Tyr Thr Lys Leu Pro Lys
            260                 265                 270

Tyr Asp Pro Asp Glu Phe
            275
```

(2) INFORMATION FOR SEQ ID NO:5:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:5:

```
Met Arg Thr Gln His Arg Arg Trp Asn Lys Ser Ser Tyr Thr Gln Ile
1               5                   10                  15

Ile Cys Met Phe Ile Ile Phe Trp Ile Leu Gln Lys Ser Lys Cys Asn
            20                  25                  30

Asn Thr Thr Ile Ala Asn Thr Ser Thr Ser Ile Thr Pro Thr Ser Leu
            35                  40                  45

Ile Ser Thr Thr Gln Leu Thr Ser Thr Leu Gln Thr Thr Glu Met Ser
50                  55                  60

Thr Thr Met Phe Thr Ser Ser Asn Gly Asn Val Asn Thr Ser Thr Gly
65                  70                  75                  80

Phe Thr Ala Ser Ser Val Lys Gly Thr Asp Val Thr Ser Thr Ile Ser
            85                  90                  95

Thr Ile Ser Thr Gln Thr Ser Thr Thr Asn Val Thr Val Ile Thr Thr
            100                 105                 110

Ser Pro Asn Gly Asp Thr Asn Ser Ser Thr Gln His Val Thr Asp Ser
            115                 120                 125

Thr Val Thr Leu Gln Thr Ile Ser Leu Ser Thr Asn Thr Thr Thr Met
130                 135                 140

Ile Asn Ala Asn Glu Asn Val Thr Thr Pro Leu Pro Thr Cys Ser Ser
145                 150                 155                 160

Pro Asn Ser Thr Asn Asn Thr Ile Ser Lys Glu Ser Glu Thr Leu Leu
            165                 170                 175

Glu Ala Ala Gln Gly Asp Asn Ile Thr Ile Thr His Asn Leu Thr Ile
            180                 185                 190

Thr Ser Cys Tyr Lys Thr Ala Trp Leu Arg His Phe Asn Ile Ser Thr
            195                 200                 205

His Gly Lys Tyr Thr His Pro Asn Ile Arg Asn Gly Lys Tyr His Asn
210                 215                 220

His Ser Leu Lys Ile Leu His Ser Arg Ile Leu Cys Glu Trp His Thr
225                 230                 235                 240

Asn Tyr Leu Lys His His Tyr Asp Leu Cys Phe Thr Cys Asp Arg Asn
            245                 250                 255

Leu Ser Leu Ser Leu Tyr Gly Leu Asn Phe Thr His Ser Gly Lys Tyr
            260                 265                 270

Ser Phe Arg Cys Tyr Lys Thr Gly His Pro Ser Glu Gln Asn Gln Asn
            275                 280                 285

Phe Asn Leu Gln Ile His Pro Arg Asn Asn Thr Asn Gly Thr His Val
290                 295                 300
```

```
        Asn Pro Trp Val Cys Glu Glu Pro Lys His Glu Trp Asp Thr Ser His
        305                 310                 315                 320

Lys Pro Thr Asn Tyr Glu Asp Asn Thr Ala Thr Ser Ser Ile Asp His
                        325                 330                 335

Leu Tyr Arg Tyr Asn Asn His Ser Asn Thr Ser His Gly Arg Arg Thr
                    340                 345                 350

Thr Trp Thr Leu Ala Leu Ile Cys Val Ala Cys Ile Leu Leu Phe Phe
                355                 360                 365

Val Arg Arg Ala Leu Asn Lys Lys Tyr His Pro Leu Ser Asp Asp Ile
            370                 375                 380

Ser Glu Ser Glu Phe Ile Val Arg Tyr Asn Pro Glu His Glu Asp
        385                 390                 395
```

(2) INFORMATION FOR SEQ ID NO:6:

(i) SEQUENCE CHARACTERISTICS:
        (A) LENGTH: 18318 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human CMV
        (B) STRAIN: Toledo (ix) FEATURE:
        (A) NAME/KEY: CDS
        (B) LOCATION: 511..1281
        (D) OTHER INFORMATION: /product = "UL133"

(ix) FEATURE:
        (A) NAME/KEY: CDS
        (B) LOCATION: 1401..2384
        (D) OTHER INFORMATION: /product = "UL135"

(ix) FEATURE:
        (A) NAME/KEY: CDS
        (B) LOCATION: 2478..3197
        (D) OTHER INFORMATION: /product = "UL136"

(ix) FEATURE:
        (A) NAME/KEY: CDS
        (B) LOCATION: 3283..3789
        (D) OTHER INFORMATION: /product = "UL138"

(ix) FEATURE:
        (A) NAME/KEY: CDS
        (B) LOCATION: 4355..4759
        (D) OTHER INFORMATION: /product = "UL139"

(ix) FEATURE:
        (A) NAME/KEY: CDS
        (B) LOCATION: 4944..5285
        (D) OTHER INFORMATION: /product = "UL140"

(ix) FEATURE:
        (A) NAME/KEY: CDS
        (B) LOCATION: 5558..6832
        (D) OTHER INFORMATION: /product = "UL141"

(ix) FEATURE:
        (A) NAME/KEY: CDS
        (B) LOCATION: 6908..7825
        (D) OTHER INFORMATION: /product = "UL142"

(ix) FEATURE:
        (A) NAME/KEY: CDS (B) LOCATION: 7813..8088
        (D) OTHER INFORMATION: /product = "UL143"

(ix) FEATURE:
        (A) NAME/KEY: CDS
        (B) LOCATION: 8468..8995
        (D) OTHER INFORMATION: /product = "UL144"

(ix) FEATURE:
        (A) NAME/KEY: CDS
        (B) LOCATION: 9327..9626
        (D) OTHER INFORMATION: /product = "UL145"

(ix) FEATURE:
        (A) NAME/KEY: CDS
        (B) LOCATION: 9910..10260
        (D) OTHER INFORMATION: /product = "UL146"

(ix) FEATURE:
        (A) NAME/KEY: CDS
        (B) LOCATION: 10328..10804
        (D) OTHER INFORMATION: /product = "UL147"

(ix) FEATURE:
        (A) NAME/KEY: CDS
        (B) LOCATION: 11106..12053
        (D) OTHER INFORMATION: /product = "UL148"

(ix) FEATURE:
        (A) NAME/KEY: CDS
        (B) LOCATION: 12133..12942
        (D) OTHER INFORMATION: /product = "UL132"

(ix) FEATURE:
        (A) NAME/KEY: CDS
        (B) LOCATION: 13569..14210
        (D) OTHER INFORMATION: /product = "UL130"

(ix) FEATURE:
        (A) NAME/KEY: CDS
        (B) LOCATION: 16216..16581
        (D) OTHER INFORMATION: /product = "UL149"

(ix) FEATURE:
        (A) NAME/KEY: CDS
        (B) LOCATION: 1004..1528
        (D) OTHER INFORMATION: /product = "UL134"

(ix) FEATURE:
        (A) NAME/KEY: CDS
        (B) LOCATION: 3063..3350
        (D) OTHER INFORMATION: /product = "UL137"

(ix) FEATURE:
        (A) NAME/KEY: CDS
        (B) LOCATION: 16337..18262
        (D) OTHER INFORMATION: /product = "UL150"

(ix) FEATURE:
        (A) NAME/KEY: CDS
        (B) LOCATION: 17752..18759
        (D) OTHER INFORMATION: /product = "UL151"

(xi) SEQUENCE DESCRIPTION: SEQ ID NO:6:

```
CGCTGTAGGG ATAAATAGTG CGATGGCGTT TGTGGGAGAA CGCAGTAGCG ATGGGTTGCG      60

ACGTGCACGA TCCTTCGTGG CAATGCCAAT GGGGCGTTCC CACGATTATC GTGGCCTGGA     120

TAACATGCGC GGCTTTAGGA ATTTGGTGTT TGGCGGGATC GTCGGCGGAT GTCTCTTCGG     180

GACCCGGCAT CGCAGCCGTA GTCGGCTGTT CTGTTTTCAT GATTTTCCTC TGCGCGTATC     240

TCATCCGTTA CCGGGAATTC TTCAAAGACT CCGTAATCGA CCTCCTTACC TGCCGATGGG     300

TTCGCTACTG CAGCTGCAGC TGTAAGTGCA GCTGCAAATG CATCTCGGGC CCCTGTAGCC     360

GCTGCTGTTC AGCGTGTTAC AAGGAGACGA TGATTTACGA CATGGTCCAA TACGGTCATC     420

GACGGCGTCC CGGACACGGC GACGATCCCG ACAGGGTGAT CTGCGAGATA GTCGAGAGTC     480
```

-continued

```
CCCCGGTTTC GGCGCCGACG GTGTCCGTCC CCCCGCCGTC GGAGGAGTCC CACCAGCCCG       540

TCATCCCACC GCAGCCGCCA GCACCGACAT CGGAACCCAA ACCGAAGAAA GGTAGGGCGA       600

AAGATAAACC GAAGGGTAGA CCGAAAGACA AACCTCCGTG CGAACCGACG GTGAGTTCAC       660

AACCACCGTC GCAGCCGACG GCAATGCCCG GCGGTCCGCC CGACGCGCCT CCCCCCGCCA       720

TGCCGCAGAT GCCACCCGGC GTGGCCGAGG CGGTACAAGC TGCCGTGCAG GCGGCCGTGG       780

CCGCGGCTCT ACAACAACAG CAGCAGCATC AGACCGGAAC GTAACCCGCC CCCGGTGCGA       840

TAAGGAATTT TCCGACTTGG CGCACATCTC CTTCCTCAAT GTTTGGACAA TAAACACATT       900

CCTTGCCAAA AAATGACGTT TCCAGAAATC CAAGGCATAA ATGTCCGTAC ACCGGCCCTT       960

CCCAACACGG AGTTTGAGAT TCCAAGCAGG AGAGAAGATC ATGGTGTGGA TATGGCTCGG      1020

CATCGGGCTC CTCGGCGGTA CCGGACTGGC TTCCCTGGTC CTGGCCATTT CCTTATTTAC      1080

CCAGCGCCGA GGCCGCAAGC GATCCGACGA GACTTCGTCG CGAGGCCGGC TCCCGGGTGC      1140

TGCTTCTGAT AAGCGTGGTG CCTGCGCGTG CTGCTATCGA AATCCGAAAG AAGACGTCGT      1200

CGAGCCGCTG GATCTGGAAC TGGGGCTCAT GCGGGTGGAC ACCCACCCGC CGACGCCGCA      1260

GGTGCCGCGG TGTACGTCGC TCTACATAGG AGAGGATGGT CTGCCGATAG ATAAACCCGA      1320

GTTTCCTCCG GCGCGGTTCG AGATCCCCGA CGTATCCACG CCGGGAACGC CGACCAGCAT      1380

CGGCCGATCT CCGTCGCATT GCTCCTCGTC GAGCTCTTTG TCGTCCTCGA CCAGCGTCGA      1440

CACGGTGCTG TATCAGCCGC CGCCATCCTG GAAGCCACCT CCGCCGCCCG GGCGCAAGAA      1500

GCGGCCGCCT ACGCCGCCGG TCCGGGCCCC CACCACGCGG CTGTCGTCGC ACAGACCCCC      1560

GACGCCGATA CCCGCGCCGC GTAAGAACCT GAGCACGCCG CCCACCAAGA AAACGCCGCC      1620

GCCCACGAAA CCCAAGCCGG TCGGCTGGAC ACCGCCGGTG ACACCCAGGC CCTTCCCGAA      1680

AACGCCGACG CCACAAAAGC CGCCGCGGAA TCCGAGACTA CCGCGCACCG TCGGTCTGGA      1740

GAATCTCTCG AAGGTGGGAC TCTCGTGTCC CTGTCCCCGA CCCCGCACGC CGACGGAGCC      1800

GACCACGCTG CCTATCGTGT CGGTTTCCGA GCTAGCCCCG CCTCCTCGAT GGTCGGACAT      1860

CGAGGAACTC TTGGAACAGG CGGTGCAGAG CGTCATGAAG GACGCCGAGT CGATGCAGAT      1920

GACCTGAGAC CGAAAGAGCG AGCGCGTCCG TTGTACAGTT GTATAGCAGC ACACGCCTTC      1980

CCTCTTTTTC ACCGCAGCTA AGAGAGAGAA AGAGAGTATG TCAGTCAAGG GCGTGGAGAT      2040

GCCAGAAATG ACGTGGGACT TGGACGTTAG AAATAAATGG CGGCGTCGAA AGGCCCTGAG      2100

TCGCATTCAC CGGTTCTGGG AATGTCGGCT ACGGGTGTGG TGGCTGAGTG ACGCCGGCGT      2160

AAGAGAAACC GACCCACCGC GTCCCCGACG CCGCCCGACT TGGATGACCG CGGTGTTTCA      2220

CGTTATCTGT GCCGTTTTGC TTACGCTTAT GATTATGGCC ATCGGCGCGC TCATCGCGTA      2280

CTTAAGATAT TACCACCAGG ACAGTTGGCG AGACATGCTC CACGATCTAT TTTGCGGCTG      2340

TCATTATCCC GAGAAGTGCC GTCGGCACCA CGAGCGGCAG AGAAGGAGAC GGCAAGCCAT      2400

GGATGTGCCC GACCCGGAAC TCGGCGACCC GGCCCGCCGG CCGTTGAACG GAGCTATGTA      2460

CTACGGCAGC GGCTGTCGCT TCGACACGGT GGAAATGGTG GACGAGACGA GACCCGCGCC      2520

GCCGGCGCTG TCATCGCCCG AAACCGGCGA CGATAGCAAC GACGACGCGG TTGCCGGCGG      2580

AGGTGCTGGC GGGGTAACAT CACCCGCGAC TCGTACGACG TCGCCGAACG CACTGCTGCC      2640

AGAATGGATG GATGCGGTGC ATGTGGCGGT CCAAGCCGCC GTTCAAGCGA CCGTGCAAGT      2700

AAGTGGCCCG CGGGAGAACG CCGTATCTCC CGCTACGTAA GAGGGTTGAG GGGGCCGTTC      2760

CCGCGCGAGT GCTGTACAAA AGAGAGAGAC TGGGACGTAG ATCCGGACAG AGGACGGTCA      2820

CCATGGACGA TCTGCCGCTG AATGTCGGGT TACCCATCAT CGGCGTGATG CTCGTGCTGA      2880
```

```
TCGTGGCCAT CCTCTGCTAT CTGGCTTACC ACTGGCACGA CACCTTCAAA CTGGTGCGCA   2940

TGTTTCTGAG CTACCGCTGG CTGATCCGCT GTTGCGAGCT GTACGGGAG TACGAGCGCC    3000

GGTTCGCGGA CCTGTCGTCT CTGGGCCTCG GCGCCGTACG GCGGGAGTCG ACAGACGAT    3060

ACCGTTCTC CGAACGGCCC GACGAGATCT TGGTCCGTTG GGAGGAAGTG TCTTCCCAGT    3120

GCAGCTACGC GTCGTCGCGG ATAACAGACC GCCGTGTGGG TTCATCGTCT TCGTCGTCGG   3180

TCCACGTCGC TAGCCAGAGA AACAGCGTGC CTCCGCCGGA CATGGCGGTG ACGGCGCCGC   3240

TGACCGACGT CGATCTGTTG AAACCCGTGA CGGGATCCGC GACGCAGTTC ACCACCGTAG   3300

CCATGGTACA TTATCATCAA GAGTACACGT GAATGAGAAA AGAAAAAAG AGGGGAGCGG    3360

ATCGCGATAA TGTCGCTTTG ACATTCTCTG CTCGATCTAC TCAGCGTCTG CACGAAACGG   3420

CATCCGCACG GAGGCGAGCC CAAGCGTATC TGCAGCAAGC GGTTCTTTCC CTCGGTGATG   3480

GTGGCAGCAT CGGTGGCGGG AGCTTGTTCG GACGATGGAC GGTGAGGAGT CCCTGGCGAT   3540

CAGGCGGCTC CCGGGTGTGG AGTTCAACGG GTGGTAATGG TGGCGGTGAT CGGTGTTAGA   3600

AAACGGTGGC CCTGGCAAAC ATATATCTAC TGTAAACCCT CTGCTCTGTT AATAAAAAGC   3660

ACACTTTTCA CATGAGTTCG TAATTTTATT GTGTAGTGGA AATTTTTACG TCATTGGGAA   3720

ACCCCAGAAT GAAAGAGTAT AATGTGCATA TCACCGGGGG TTCCCTGTCA GTACGAATGT   3780

ACACAACGCG GGTTACATTA CGATAAACTT TCCGGTAAAA CGATGCCGAT ACAGCGTGTA   3840

TAACGCTGAT TGTTACGACA AACGAGTTGG TATATCCATT ATATAGTAAC GAACATGCTG   3900

TGGATATTAG TTTTATTTGC ACTCGCCGCA TCGGCGAGTG AAACCACTAC AGGTACCAGC   3960

TCTAATTCCA GTCAATCTAC TAGTGCTACC GCCAACACGA CCGTATCGAC ATGTATTAAT   4020

GCCTCTAACG GCAGTAGCTG GACAGTACCA CAGCTCGCGC TGCTTGCCGC TAGCGGCTGG   4080

ACATTATCTG GACTCCTTCT CTTATTTACC TGCTGCTTTT GCTGCTTTTG GCTAGTACGT   4140

AAAATCTGCA GCTGCTGCGG CAACTCCTCC GAGTCAGAGA GCAAAACAAC CCACGCGTAC   4200

ACCAATGCCG CATTCACTTC TTCCGACGCA ACGTTACCCA TGGGCACTAC AGGGTCGTAC   4260

ACTCCCCCAC AGGACGGCTC ATTTCCACCT CCGCCTCGGT GACGTAGGCT AAACCGAAAC   4320

CCACGTTGAA CCTAACGCGG TTTCGGAAGG CCTGAGACGT CACTTTCACA ATGACGTCCG   4380

TATACACGTT CATCATAAAA CACCGTAGAG GCTAAGGCTT CGGTAGGGAG AGACCTCAAC   4440

TGTTCCTGAT GAGCACCCGT GCTCTCATCT CTTCAGACTT GTCATGACCC CCGCTCAGAC   4500

TAACGCGACT ACCACCGTGC ACCCGCACGA CGCAAAAAAC GGCAGCGGCG GTAGTGCCCT   4560

GCCGACCCTC GTCGTTTTCG GCTTTATCGT TACGCTACTT TTCTTTCTCT TTATGCTCTA   4620

CTTTTGGAAC AACGACGTGT TCCGTAAGCT GCTCCGTGCG CTTGGATCCA GCGCTGTTGC   4680

GACCGCTTCG ACGCGTGGCA AGACGAGGTC ATCTACCGTC GTCCATCACG TCGTTCCCAG   4740

AGCGACGACG AGAGTCGTAC TAACAGCGTG TCATCGTACG TTCTTTTATC ACCCGCGTCC   4800

GATGGCGGTT TTGACAACCC GGCACTGACA GAGGCCGTCG ACAGCGTGGA CGACTGGGCG   4860

ACCACCTCGG TTTTCTACGC CACGTCCGAC GAAACGGCGG ACGCCGAGCG CCGAGACTCG   4920

CAGCAACTGC TCATCGAGCT TCCGCCGGAG CCGCTCCCGC CCGACGTGGT GGCGGCCATG   4980

CAGAAAGCAG TGAAACGCGC TGTACAGAAC GCACTACGAC ACAGCCACGA CTCTTGGCAG   5040

CTTCATCAGA CCCTGTGACG CCAGATGAAC GTTCCTTCTT AAACATCCGA GGTAGCAATG   5100

AGACAGGTCG CGTACCGCCG GCGACGCGAG AGTTCCTGCG CGGTGCTGGT CCACCACGTC   5160

GGCCGCGACG GCGACGGCGA GGGGGAGGCA GCAAAAAAGA CCTGCAAAAA AACCGGACGC   5220

TCAGTTGCGG GCATCCCGGG CGAGAAGCTG CGTCGCACGG TGGTCACCAC CACGCCGGCC   5280
```

-continued

```
CGACGTTTGA GCGGCCGACA CACGGAGCAG GAGCAGGCGG GCATGCGTCT CTGTGAAAAA    5340

GGGAAGAAAA GAATCATCAT GTGCCGCCGG GAGTCGCTCC GAACTCTGCC GTGGCTGTTC    5400

TGGGTGCTGT TGAGCTGCCC GCGACTCCTC GAATATTCTT CCTCTTCGTT CCCCTTCGCC    5460

ACCGCTGACA TTGCCGAAAA GATGTGGGCC GAGAATTATG AGACCACGTC GCCGGCGCCG    5520

GTGTTGGTCG CCGAGGGAGA GCAAGTTACC ATCCCCTGCA CGGTCATGAC ACACTCCTGG    5580

CCCATGGTCT CCATTCGCGC ACGTTTCTGT CGTTCCCACG ACGGCAGCGA CGAGCTCATC    5640

CTGGACGCCG TCAAAGGCCA TCGGCTGATG AACGGACTCC AGTACCGCCT GCCGTACGCC    5700

ACTTGGAATT TCTCGCAATT GCATCTCGGC CAAATATTCT CGCTTACTTT TAACGTATCG    5760

ATGGACACAG CCGGCATGTA CGAATGCGTG CTACGCAACT ACAGCCACGG CCTCATCATG    5820

CAACGCTTCG TAATTCTCAC GCAGCTGGAG ACGCTCAGCC GGCCCGACGA ACCTTGCTGC    5880

ACACCGGCGT TAGGTCGCTA CTCGCTGGGA GACCAGATCT GGTCGCCGAC GCCCTGGCGT    5940

CTACGGAATC ACGACTGCGG AACGTACCGC GGCTTTCAAC GCAACTACTT CTATATCGGC    6000

CGCGCCGACG CCGAGGATTG CTGGAAACCC GCATGTCCGG ACGAGGAACC CGACCGCTGT    6060

TGGACAGTGA TACAGCGTTA CCGGCTCCCC GGCGACTGCT ACCGTTCGCA GCCACACCCG    6120

CCGAAATTTT TACCGGTGAC GCCAGCACCG CCGGCCGACA TAGACACCGG GATGTCTCCC    6180

TGGGCCACTC GGGGAATCGC GGCGTTTTTG GGGTTTTGGA GTATTTTTAC CGTATGTTTC    6240

CTATGCTACC TGTGTTATCT GCAGTGTTGT GGACGCTGGT GTCCCACGCC GGGAAGGGGA    6300

CGACGAGGCG GTGAGGGCTA TCGACGCCTA CCGACTTACG ATAGTTACCC CGGTGTTAGA    6360

AAGATGAAGA GGTGAGAACA CGTATAAAAT AAAAAAATAA TATGTTAAAA AATGCAGTGT    6420

GTGAAGTGTG AATAGTGTGA TTAAAATATG CGGATTGAAT GGGTGTGGTG GTTATTCGGA    6480

TACTTTGTGT CATCCGTTGG GAGCGAACGG TCATTATCCT ATCGTTACCA CTTGGAATCT    6540

AATTCATCTA CCAACGTGGT TTGCAACGGA AACATTTCCG TGTTTGTAAA CGGCACCCTA    6600

GGTGTGCGGT ATAACATTAC GGTAGGAATC AGTTCGTCTT TATTAATAGG ACACCTTACT    6660

ATACAAGTAT TGGAATCATG GTTCACACCC TGGGTCCAAA ATAAAAGTTA CAACAAACAA    6720

CCCCTAGGTG ACACTGAAAC GCTTTATAAT ATAGATAGCG AAAACATTCA TCGCGTATCT    6780

CAATATTTTC ACACAAGATG GATAAAATCT CTGCAAGAGA ATCACACTTG CGACCTCACA    6840

AACAGTACAC CTACCTATAC ATATCAAGTA AACGTGAACA ACACGAATTA CCTAACACTA    6900

ACATCCTCGG GATGGCAAGA CCGTCTAAAT TACACCGTCA TAAATAGTAC ACACTTTAAC    6960

CTCACAGAAT CGAACATAAC CAGCATTCAA AAATATCTCA ACACTACCTG CATAGAAAGA    7020

CTCCGTAACT ACACCTTGGA GTCCGTATAC ACCACAACTG TGCCTCAAAA CATAACAACA    7080

TCTCAACACG CAACAACCAC TATGCACACA ATACCTCCAA ATACAATAAC AATTCAAAAT    7140

ACAACTCAAA GCCATACTGT ACAGACGCCG TCTTTTAACG ACACACATAA CGTGACGAAA    7200

CACACGTTAA ACATAAGCTA CGTTTTATCA CAAAAAACGA ATAACACAAC ATCACCGTGG    7260

ATATATGCCA TACCTATGGG CGCTACAGCC ACAATAGGCG CCGGTTTATA TATCGGGAAA    7320

CACTTTACGC CGGTTAAGTT CGTATACGAG GTATGGCGCG GTCAGTAAAG ACGATTCGGA    7380

TTCAACACAT ATACTCCCCA CGATCCTCGA ACACCTTACA GCATATGAGC AAAAAACAAG    7440

AAAGTATAGC CACAATCACA TTTGGGCGAA TAACATGCTG TCATCCACTA GCGTCTATTA    7500

ATCTAATGTT TAACGGGAGC TGTACTGTCA CCGTTAAAAT ATCCATGGGA ATCAACGGGT    7560

CAACCAACGT CCATCAGCTT GTGATTGTGC TCCATCTGGG TAACCGCTGT CAGCCTTGGC    7620

GACAGGTGTA ATCACAGCTG TCACATAACT CACGAAGCCT CCAATCACAG CAGCACACAT    7680
```

```
-continued

AGTCCTAACG CCATTGGCGT GTATAAAAGT TCGGAAAACT TGACGGTTGT ACGGCACGAC      7740

AAATCGATGT AGTGGTATGT TTTTCCAGCA GAGACCGTGT GCGGTCTCTT AGGTTCGCTA      7800

TACTGTGGCT GGAAACTGGT TACCTGTGAA GATGGCTAAC TATCCTGTTC TGTCCTGGAA      7860

AAACTTTTGG CGTCGTAGGT GGACTTTGCA GTATGCGGGT TAGTGAAGTT ATGTCATTTA      7920

TTTACGTTTA CGATCTCGTA TTACAAACCG CGGAGAGGA GATACCGTTC GGCCCCATGA       7980

GTTATTTTTA TTCTTCCGGT AGGAGGCATG AAGCCTCTGA TAATGCTCAT CTGCTTTGCT     8040

GTGATATTAT TGCAGCTTGG AGTGACTAAA GTGTGTCAGC ATAATGAAGT GCAACTGGGC     8100

AATGAGTGCT GCCCTCCGTG TGGTTCGGGA CAAAGAGTTA CTAAAGTATG CACGGATTAT     8160

ACCAGTGTAA CGTGTACCCC TTGCCCCAAC GGCACGTATG TATCGGGACT TTACAACTGT    8220

ACCGATTGCA CTCAATGTAA CGTCACTCAG GTCATGATTC GTAACTGCAC TTCCACCAAT    8280

AATACCGTAT GCGCACCTAA GAACCATACG TACTTTTCCA CTCCAGGCGT CCAACATCAC    8340

AAACAACGAC AGCAAAATCA TACCGCACAT ATAACCGTCA AACAAGGAAA AAGCGGTCGT    8400

CATACTCTAG CCTGGTTGTC TCTCTTTATC TTTCTTGTGG GTATCATACT TTTAATTCTC    8460

TATCTTATAG CCGCCTATCG GAGTGAGAGA TGCCAACAGT GTTGCTCAAT CGGCAAAATT    8520

TTCTACCGCA CCCTGTAAGC TTCCTGTTGT TGTTTTTACA TCACGGTACG ATGAAGTCAC    8580

ACAGATAATT ACAGATGAGC TGTTCATATT TTTTATTATT TTTTCCAATT CCTGCACTAA    8640

AAAAAGAAGC ACTTTACGGA ACCGTGTCTG AGTATCTGTG GGGAATTTAG GTACTTTTTG    8700

CCGACGTCAG GAAAAATAAG TGTCGCCTAC ATAAGAGCCC GGTGCTATCG TGCTGTCACT    8760

CTTTCTTGTT GCCTTCGATG TACGGCGTCC TGGCTCATTA CTACTCCTTC ATCAGTAGCC    8820

CCAGCGTTAT GGTTAATTTT AAGCATCATA ACGCCGTGCA GCTGTTATGT GCACGGACCC    8880

GAGACGCACT GCCGGATGGG AACGTTTAAC CCATCATGCG TCGTATCACG CGAACTACGG    8940

GGCATACGCC GTGTTGATGG CTACATCGCA AAGAAAGTCC CTAGTGTTAC ATCGATACAG    9000

TGCCGTGACA GCCGTGGCCC TGCAGCTCAT GCCTGTTGAG ATCGTCCGCA AGCTAGATCA    9060

GTCGGACTGG GTGCGGGGTG CCTGGATCGT GTCAGAGACT TTTCCAACTA GCGACCCCAA    9120

AGGAGTTTGG AGCGACGATG ACTCCTCGAT GGGTGGAAGT GATGATTGAT GATGAGAACC    9180

TGACAAGAAA GACGAGAGAG AAATTTAGAG CTGTCATTGT AGAATTAGTC TAGATTCCTG    9240

ATAATAAACA GTATCGATTT TGAAACCTAA TTGACGTGTG ATCGATTTTT AAACCTCTGT    9300

GTTGTGTGAT TGATTGGTAT GTGGGGGGAT CCGATTTCAA AGGGGGGTAC TTATCGGGAA    9360

TTGATGTGTC ATGGACGCAG TTTTGAGCGA TTTTCCGGGA ATACCGGATA TTACGAATTA    9420

CTGGTAGTGA CGTAGATAAT AAAATTATAA TGCGATTAAT TTTTGGTGCG TTGATTATTT    9480

TTTTAGCATA TGTGTATCAT TATGAGGTGA ATGGAACAGA ATTACGCTGC AGATGTCTTC    9540

ATAGAAAATG GCCGCCTAAT AAAATTATAT TGGGTAATTA TTGGCTTCAT CGCGATCCCA    9600

GAGGGCCCGG ATGCGATAAA AATGAACATT TATTGTATCC AGACGGAAGG AAACCGCCTG    9660

GACCTGGAGT ATGTTTATCG CCCGATCACC TCTTCTCAAA ATGGTTAGAC AAACACAACG    9720

ATAATAGGTG GTATAATGTT AACATAACGA AATCACCAGG ACCGAGACGA ATAAATATAA    9780

CCTTGATAGG TGTTAGAGGA TAATATTTAA TGTATGTTTT CAAACAGACA AGTTCGTTAA    9840

AACAAAATAT TACAGTATGT GTTAATATTG GTGCTAACAT GGTTGCACCA TCCGGTTTCA    9900

AACTCGCATA TCAATCTGTT ATCGGTACGA CACCTGTCAT TAATCGCATA TATGTTACTT    9960

ACCATATGTC CCCTAGCCGT CCATGTTTTA GAACTAGAAG ATTACGACAG GCGCTGCCGT    10020

TGCAACAACC AAATTCTGTT GAATACCCTG CCGGTCGGAA CCGAATTGCT TAAGCCAATC    10080
```

| | | | | |
|---|---|---|---|---|
| GCAGCGAGCG | AAAGCTGCAA | TCGTCAGGAA | GTGCTGGCTA | TTTTAAAGGA | CAAGGGAACC | 10140 |
| AAGTGTCTCA | ATCCTAACGC | GCAAGCCGTG | CGTCGTCACA | TCAACCGGCT | ATTTTTTCGG | 10200 |
| TTAATCTTAG | ACGAGGAACA | ACGCATTTAC | GACGTAGTGT | CTACCAATAT | TGAGTTCGGT | 10260 |
| GCCTGGCCAG | TCCCTACGGC | CTACAAAGCC | TTTCTTTGGA | AATACGCCAA | GAGACTGAAC | 10320 |
| TACCACCACT | TCAGACTGCG | CTGGTGATCA | TGTCCCTATT | TTACCGTGCG | GTAGCTCTGG | 10380 |
| GCACGCTAAG | CGCTTTGGTG | TGGTACAGCA | CTAGCATCCT | CGCAGAGATT | AACGAAAATT | 10440 |
| CCTGCTCCTC | ATCTTCTGCG | GATCACGAAG | ACTGCGAGGA | ACCGGACGAG | ATCGTTCGCG | 10500 |
| AAGAGCAAGA | CTATCGGGCT | CTGCTGGCCT | TTTCCCTAGT | GATTTGCGGT | ACGCTCCTCG | 10560 |
| TCACTTGTGT | GATCTGAGAC | GTCATGCTGG | TAGCGTTTAT | GAGTCGGGCG | GTGGCCGACA | 10620 |
| CGCCGCATTT | CCTAACCCGC | GCAGCATGTT | GCGCTTGCTG | TTCACGCTCG | TCCTGCTGGC | 10680 |
| CCTCCACGGG | CAGTCTGTCG | GCGCTAGCCG | CGACTATGTG | CATGTTCGGC | TACTGAGCTA | 10740 |
| CCGAGGCGAC | CCCCTGGTCT | TCAAGCACAC | TTTCTCGGGT | GTGCGTCGAC | CCTTCACCGA | 10800 |
| GCTAGGCTGG | GCTGCGTGTC | GCGACTGGGA | CAGTATGCAT | TGCACACCCT | TCTGGTCTAC | 10860 |
| CGATCTGGAG | CAGATGACCG | ACTCGGTGCG | GCGTTACAGC | ACGGTGAGCC | CCGGCAAGGA | 10920 |
| AGTGACGCTT | CAGCTTCACG | GGAACCAAAC | CGTACAGCCG | TCGTTTCTAA | GCTTTACGTG | 10980 |
| CCGCCTGCAG | CTAGAACCCG | TGGTGGAAAA | TGTTGGCCTC | TACGTGGCCT | ACGTGGTCAA | 11040 |
| CGACGGCGAA | CGCCCACAAC | AGTTTTTTAC | ACCGCAGGTA | GACGTGGTAC | GCTTTGCTCT | 11100 |
| ATATCTAGAA | ACACTCTCCC | GGATCGTGGA | ACCGTTAGAA | TCAGGTCGCC | TGGCAGTGGA | 11160 |
| ATTTGATACG | CCTGACCTAG | CTCTGGCGCC | CGATTTAGTA | AGCAGCCTCT | TCGTGGCCGG | 11220 |
| ACACGGCGAG | ACCGACTTTT | ACATGAACTG | GACGCTGCGT | CGCAGTCAGA | CCCACTACCT | 11280 |
| GGAGGAGATG | GCCTTACAGG | TGGAGATTCT | AAAACCCCGC | GGCGTACGTC | ACCGCGCTAT | 11340 |
| TATCCACCAT | CCGAAGCTAC | AGCCGGGCGT | TGGCCTGTGG | ATAGATTTCT | GCGTGTACCG | 11400 |
| CTACAACGCG | CGCCTGACCC | GCGGCTACGT | ACGATACACC | CTGTCACCGA | AAGCGCGCTT | 11460 |
| GCCCGCAAAA | GCAGAGGGTT | GGCTGGTGTC | ACTAGACAGA | TTCATCGTGC | AGTACCTCAA | 11520 |
| CACATTGCTG | ATTACAATGA | TGGCGGCGAT | ATGGGCTCGC | GTTTTGATAA | CCTACCTGGT | 11580 |
| GTCGCGGCGT | CGGTAGAGGC | TTGCGGAAAC | CACGTCCTCG | TCACACGTCG | TTCGCGGACA | 11640 |
| TAGCAAGAAA | TCCACGTCGC | CACATCTCGA | GAATGCCGGC | CTTGCGGGGT | CCCCTTCGCG | 11700 |
| CAACATTCCT | GGCCCTGGTC | GCGTTCGGGT | TGCTGCTTCA | GATAGACCTC | AGCGACGCTA | 11760 |
| CGAATGTGAC | CAGCAGCACA | AAAGTCCCTA | CTAGCACCAG | CAACAGAAAT | AACGTCGACA | 11820 |
| ACGCCACGAG | TAGCGGACCC | ACAACCGGGA | TCAACATGAC | CACCACCCAC | GAGTCTTCCG | 11880 |
| TTCACAACGT | GCGCAATAAC | GAGATCATGA | AAGTGCTGGC | TATCCTCTTC | TACATCGTGA | 11940 |
| CAGGCACCTC | CATTTTCAGC | TTCATAGCGG | TACTGATCGC | GGTAGTTTAC | TCCTCGTGTT | 12000 |
| GCAAGCACCC | GGGCCGCTTT | CGTTTCGCCG | ACGAAGAGGC | CGTCAACCTG | TTGGACGACA | 12060 |
| CGGACGACAG | TGGCGGCAGC | AGCCCGTTTG | GCAGCGGTTC | CCGACGAGGT | TCTCAGATCC | 12120 |
| CCGCCGGATT | TTGTTCCTCG | AGCCCTTATC | AGCGGTTGGA | AACTCGGGAC | TGGGACGAGG | 12180 |
| AGGAGGAGGC | GTCCGCGGCC | CGCGAGCGCA | TGAAACATGA | TCCTGAGAAC | GTCATCTATT | 12240 |
| TCAGAAAGGA | TGGCAACTTG | GACACGTCGT | TCGTGAATCC | CAATTATGGG | AGAGGCTCGC | 12300 |
| CTTTGACCAT | CGAATCTCAC | CTCTCGGACA | ATGAGGAGGA | CCCCATCAGG | TACTACGTTT | 12360 |
| CGGTGTACGA | TGAACTGACC | GCCTCGGAAA | TGGAAGAACC | TTCGAACAGC | ACCAGCTGGC | 12420 |
| AGATTCCCAA | ACTAATGAAA | GTTGCCATGC | AACCCGTCTC | GCTCAGAGAT | CCCGAGTACG | 12480 |

```
ACTAGGCTTT TTTTTTTGTC TTTCGGTTCC AACTCTTTCC CCGCCCCATC ACCTCGCCTG   12540

TACTATGTGT ATGATGTCTC ATAATAAAGC TTTCTTTCTC AGTCTGCAAC ATGCAGCTGT   12600

GTCGGGTGTG GCTGTCTGTT TGTCTGTGCG CCGTGGTGCT GGGTCAGTGC CAGCGGGAAA   12660

CCGCGGAAAA AAACGATTAT TACCGAGTAC CGCATTACTG GGACGCGTGC TCTCGCGCGC   12720

TGCCCGACCA AACCCGTTAC AAGTATGTGG AACAGCTCGT GGACCTCACG TTGAACTACC   12780

ACTACGATGC GAGCCACGGC TTGGACAACT TTGACGTGCT CAAGAGGTGA GGGTACGCGC   12840

TAAAGGTGCA TGACAACGGG AAGGTAAGGG CGAACGGGTA ACGGCTAAGT AACCGCATGG   12900

GGTATGAAAT GACGTTTGGA ACCTGTGCTT GCAGAATCAA CGTGACCGAG GTGTCGTTGC   12960

TCATCAGCGA CTTTAGACGT CAGAACCGTC GCGGCGGCAC CAACAAAAGG ACCACGTTCA   13020

ACGCCGCCGG TTCGCTGGCG CCACACGCCC GGAGCCTCGA GTTCAGCGTG CGGCTCTTTG   13080

CCAACTAGCC TGCGTCACGG GAAATAATAT GCTGCGGCTT CTGCTTCGTC ACCACTTTCA   13140

CTGCCTGCTT CTGTGCGCGG TTTGGGCAAC GCCCTGTCTG GCGTCTCCGT GGTCGACGCT   13200

AACGGCAAAC CAGAATCCGT CCCCGCCATG GTCTAAACTG ACGTATTCCA AACCGCATGA   13260

CGCGGCGACG TTTTACTGTC CTTTTCTCTA TCCCTCGCCC CCACGGTCCC CCTTGCAATT   13320

CTCGGGTTC CAGCAGGTAT CAACGGGTCC CGAGTGTCGC AACGAGACCC TGTATCTGCT   13380

GTACAACCGG GAAGGCCAGA CCTTGGTGGA GAGAAGCTCC ACCTGGGTGA AAAAGGTGAT   13440

CTGGTATCTG AGCGGTCGCA ACCAGACCAT CCTCCAACGG ATGCCCCAAA CGGCTTCGAA   13500

ACCGAGCGAC GGAAACGTGC AGATCAGCGT GGAAGACGCC AAGATTTTTG GAGCGCACAT   13560

GGTGCCCAAG CAGACCAAGC TGCTACGCTT CGTCGTCAAC GATGGCACGC GTTATCAGAT   13620

GTGTGTGATG AAGCTGGAGA GCTGGGCCCA CGTCTTCCGG GACTACAGCG TGTCTTTTCA   13680

GGTGCGATTG ACGTTCACCG AGGCCAATAA CCAGACTTAC ACCTTCTGTA CCCATCCCAA   13740

TCTCATCATT TGAGCCCGTC GCGCGCGCAG GGAATTTTGA AAACCGCGCG TCATGAGTCC   13800

CAAAGACCTG ACGCCGTTCT TGACGACGTT GTGGCTGCTA TTGGGTCACA GCCGCGTGCC   13860

GCGGGTGCGC GCAGAAGAAT GTTGCGAATT CATAAACGTC AACCACCCGC CGGAACGCTG   13920

TTACGATTTC AAAATGTGCA ATCGCTTCAC CGTCGCGTAC GTATTTTCAT GATTGTCTGC   13980

GTTCTGTGGT GCGTCTGGAT TTGTCTCTCG ACGTTTCTGA TAGCCATGTT CCATCGACGA   14040

TCCTCGGGAA TGCCAGAGTA GATTTTCATG AATCCACAGG CTGCGGTGTC CGGACGGCGA   14100

AGTCTGCTAC AGTCCCGAGA AAACGGCTGA GATTCGCGGG ATCGTCACCA CCATGACCCA   14160

TTCATTGACA CGCCAGGTCG TACACAACAA ACTGACGAGC TGCAACTACA ATCCGTAAGT   14220

CTCTTCCTCG AGGGCCTTAC AGCCTATGGG AGAGTAAGAC AGAGAGGGAC AAAACATCAT   14280

TAAAAAAAAA AGTCTAATTT CACGTTTTGT ACCCCCCTTC CCCTCCGTGT TGTAGCCCAT   14340

CGGCCGCGGC GATCTCCTAG TAACACTCGT CCGACACTTC CACCATCTCC AGCTCGGCCG   14400

GCGGTTCGGC ATCCTCTACC AGCGGCGTCG TCTCATCTTT GCCGCAGCAG CGGACGCACA   14460

CCTTCTCCAG GCAGAACGCC ACCAGCTGCC GCCGAACGTA CCACAGGTAC ACGTGCAGAC   14520

CTGCGAACAG GACTACGGAG GTCATGACCA CCACGACGCA CACGGGAATC CAGGGATCGA   14580

GATTGTTGCT GGAACTCATG GCTATCGCCA CCGACGTGCC CGCGTCTGTC TCACCGCCGC   14640

TCGCCCGATG TCGCGCGGCT TGTTATACGC TAGCCCGTCG CCGCCTCGGG GCACGGTGCC   14700

CTCCTACCCA CGTAACTTCC TCCGTGACTT AAAGTCGCGT GTGGTAGATC TCCTGCTCCG   14760

TGGACGAACC GTCCGGCAGG ATAGCGGTTA AGGATTCGGT GCTAAGGCCG TGTCGCCAAC   14820

GTCGAATGCT ACGTTGCAAC AGCTTCGACG GACGGCCATC CCCTCTCTCA TCGCAATAAT   14880
```

-continued

```
AAAACACCAG CAGCGCGCAC GACGCGATCA CGGTGACACC CATGATTAGA CCCACGCAGA  14940
TAGCCAGCCC CGCTAGCGTA TCTAGCGCCA TCCCGTTCGC TCCCGTTGTC TCCTGAGCGA  15000
AGCAACTTCT CGGTCCCCGT TTTCAACAGT TTTTGTTTCC TTCTCCGCGA CTAGATGTTA  15060
ACGCCCGCGG TCTTTCCGGC CGTGCTCTAC CTCCTGGCGC TTGTCGTCTG GGTTGAGATG  15120
TTCTGCCTCG TCGCCGTAGC CGTCGTCGAG CGCGAGATCG CCTGGGCGCT GCTGCTGCGG  15180
ATGCTGGTCG TTGGCCTGAT GGTGGAAGTC GGCGCCGCCG CCGCTTGGAC CTTCGTGCGT  15240
TGTCTTGCCT ATCAGCGCTC CTTCCCCGTG CTTACGGCCT TCCCCTGAAA CCCACGTTAA  15300
CCGACCGTCC CAAAAACGCC GGTGTTAACA CAGGAAAAAA AGAAACCACG CAGGAACCGC  15360
GCAGGAACCA CGCGGAACAT GGGACACTAT CTGGAAATCC TGTTCAACGT CATCGTCTTC  15420
ACTCTGCTGC TCGGCGTCAT GGTCAGTATC GTCGCTTGGT ACTTCACGTG AACCACCGTC  15480
GTCCCGGTTT AAAAACCATC ATCGACGGCC GTTATAAAGC CACCCGGACA CGCGCCGCGG  15540
CACTTGCCTA CGGCGCTGCT TCAGGGAAAC TCCTCTTCCT TCTGCTCTTC CTCCTTCACC  15600
GCAGGGATCG TTTCCCTCGA CCAGGGACTC GCCGAAGCAA CCGCCGGAGC AACCTGGAGG  15660
AGTCGCGGCA TGACGGCGCC CAAGTGTGTC ACCACCAGTA CTTATCTGGT CAAGACCAAG  15720
GAACAGCCCT GGTGGCCCGA CAACGCCATC AGGAGATGGT GGATCAGTGT TGCTATCGTC  15780
ATCTTCATCG GAGTCTGTCT GGTGGCCCTG ATGTACTTTA CGCAGCAGCA GGCACGCAGC  15840
GGGAGCAGCA GCGGCTAGAC AAGTCTCTGG CGGCTACAGC TCCAAGCGCC GTAGCCGGGC  15900
CGCCTGCCGA TCGCGACGTC GTGGACCATC GAACAGAGAC TCACGCGTAC GAGACCCCGA  15960
GGTACGCCAC GCGGTGCCTA ACGCGGTATA CCACACCCGT ACGGTCTGCA GTGCGGCGTA  16020
CAACGTGTGG AAAACGCGTT GCGTCGCAGA GTCCGCCACG TTCCTGTCTT GTCGCTCCCC  16080
AATCGTCTCC CGCACACCCC CCGCGACACC CAGAGGGCGG GTGAGCCAAG TATTCTTAAG  16140
GCCGTTCTTT GTTCCATAGC CCATAAATTG TTGATTCCGG AGCTCGTTGG CGCGGAAATA  16200
GCCGGATAAG GGGAGCAACA ACCGTTGGCG AAAGCCGTCC CGCTCATTCA GTCCGGGTTT  16260
CGCGTCCAGT CGGACGTGTG ACCGTTGGGC AACGGAACGG CGTTTCACTG CCAAAATCGT  16320
ATCGGGTAGT GTACGAGACG TCGGCGGTGC AGAATGCGAC TCGCGGCGTA GCTCGCCGTC  16380
GCTATGCGGC TCGTCGCCGT GTGGCGCGGC CTGGCCGGCT GTCTGCGTCC AGATCTGTTG  16440
GCCTTTTGGT TCCTCTGGCT GCTGCTGCGT GTGTGCTTTG GTAGACGCGG TGGCAGTTTG  16500
CGGTCTGCGG TAAGTGAGGA TGTCGCCGAG CAAACGCACT TGCGGCGCGT GGGCGGCACG  16560
CGTGTCATTG TAGGTTCGTT GCCAGATGGC AAGTGCTGTC AACAGCAGGC GTTGTGGGCG  16620
GTCGGTGTAT TTTTGTGGGT TGCGGTGAGA GTCGGCACTC GGTGTTTTGT GAGTCATCTC  16680
AACTATCTGT GTTGCTTTGA GCAGCGTCCA GAACAGCGAC GCGACTTTGG GGATGGCCTC  16740
GTGCTCACCT CCGCGGAGAG CGCCGCCGGA CCTGCTCGTC AGCAGCGAGC TACGCAGACG  16800
GAATATCTGG AGGAGAGTTA CGTGTGTCAC AGGAGAGCGC GGGTCTCCGG CGGTAACGAC  16860
GGCGGTGTCG TCGACACGTG TGCGGCCTGT TGTGCTCTGC GGAAAAGTGC CGGTCTCGGA  16920
GACCGTGGAC GAAAAAGAGA ACGCAGCAGC TACCGCTGGC GGCGGCGGCG TTAATGCAGC  16980
CGTTGATGTT CGACGTTGTG AGCACTCGGA AACAGCGGTG AGGCAGAAGG TCGATTCTCC  17040
AGGGAACGAC AGTCGATGCG TGGTAGCCGC AGCAGGTGAG GTTGGGCGG  ACAACGTGTT  17100
GCGGATTGTG GCGAGAACGT CGTCCTCCCC TTCTTCACCG CCCCACCCAC CCTCGGTTGG  17160
TGTTTCTTTT TTCTTGTGTC CTGCAGATAG TTCCACGGAC AGCGACGGCA AGTCCATAAT  17220
CAGCGGTGTG CAAGTGGTGG AACACGACGA AGATATCATC GCGCCGCAGA GTTTGTGGTG  17280
```

-continued

```
CACGGCGTTC AAGGAAGCCC TCTGGGATGT GGCTCTGTTG AAGTGCCGC GTTGGGCGTG       17340

GCAGGGCTGG AAGAGGTGGC GCAACAGCGA GGCCGGGCGT CGATGGAGTG CTGGGTCTGC       17400

GTCGGCTTCC AGCTTGTCTG ACTTGGCGGG CGAGGCCGTT GGAGAATTGG TGGGATCGGT       17460

CGTCGCGTAC GTGATCCTTG AACGTCTGTG GTTGGCAGCC AGAGGTTGGG TGTGCGAAAC       17520

AGGTGTGGAA GCCGAGGAGG CCATGTCGCG GCGGCGACAG CGCATGCTGT GGCGTATTGT       17580

TCTCTCGTGG AGGCGACGGC GAATGCAGCA GACGGTGTTC GATGGAGATG GCGTGCGGGG       17640

AAGAAAGCGC CGTGTTGTGA GCAGACGACG TAGGATGCGG GACGTCGGAG CACATGGGCC       17700

ATGTGTGGTG GCAGATGGCG GTGTCCGCTG GTGTCTGCTG CGGCAGTGCA TAGACGAAGC       17760

AACATGTCGC TGTGAAGAGA TAGAGTGTGA GCATAGCTGC ATGCAGCGTT GCGTGTATAA       17820

GCGGGGGGGA TTAAGACGTT AATAAAGAAT AGCGGCGGTT CTGATAGGGC GACCGCTGAA       17880

GTGAGCTGCG TGTGCGTGTG GTTTGTGGAG TCCCCGCCGC CCCCGGTCCC GTGTCCGCCG       17940

GCAAAGCCCC CCGGNTCCGC ACACTCCTGG CCGCGCAACC CTCGTCGCTG CAAAAGCCCC       18000

CCGTCCCCGC ACACCCCCGC GACCGCCGGT CCCGCGAGTC CCCGTCCCCG CCGCAAAAGG       18060

CCCCCGTCCT CGCCGCAAAC ACCCCCGTCA CCCCCGTCCC TCAGNCCGGG TCCGCGAGTC       18120

CCCGTTCCCA GCGTAATCCC CGTACCCGCA ACGNCCCGGN CCCACCGTCG TCCCGCACAC       18180

CCCCCGTCCC CCAGCCCGGT GCCCAGCGTG CGAAAAAAGC TCCGTCCCTC ACACCCGCAG       18240

AAAGATCCCT CAGCGCGGTG AAACCCCGTC CCCAGCGCCG TGCCGCTGAC AAAGACCATG       18300

GGACGACACG CACAGGCA                                                    18318
```

(2) INFORMATION FOR SEQ ID NO:7:

(i) SEQUENCE CHARACTERISTICS:
        (A) LENGTH: 257 amino acids
        (B) TYPE: amino acid
        (D) TOPOLOGY: linear (ii) MOLECULE TYPE: protein (vii) IMMEDIATE SOURCE:
        (B) CLONE: tol.01

(ix) FEATURE:
        (A) NAME/KEY: Protein
        (B) LOCATION: 1..257
        (D) OTHER INFORMATION: /label= UL133

(xi) SEQUENCE DESCRIPTION: SEQ ID NO:7:

```
Met Gly Cys Asp Val His Asp Pro Ser Trp Gln Cys Gln Trp Gly Val
1               5                   10                  15

Pro Thr Ile Ile Val Ala Trp Ile Thr Cys Ala Ala Leu Gly Ile Trp
            20                  25                  30

Cys Leu Ala Gly Ser Ser Ala Asp Val Ser Ser Gly Pro Gly Ile Ala
        35                  40                  45

Ala Val Val Gly Cys Ser Val Phe Met Ile Phe Leu Cys Ala Tyr Leu
    50                  55                  60

Ile Arg Tyr Arg Glu Phe Phe Lys Asp Ser Val Ile Asp Leu Leu Thr
65                  70                  75                  80

Cys Arg Trp Val Arg Tyr Cys Ser Cys Ser Cys Lys Cys Ser Cys Lys
                85                  90                  95

Cys Ile Ser Gly Pro Cys Ser Arg Cys Cys Ser Ala Cys Tyr Lys Glu
            100                 105                 110

Thr Met Ile Tyr Asp Met Val Gln Tyr Gly His Arg Arg Pro Gly
        115                 120                 125
```

```
His Gly Asp Asp Pro Asp Arg Val Ile Cys Glu Ile Val Glu Ser Pro
        130                 135                 140

Pro Val Ser Ala Pro Thr Val Ser Val Pro Pro Ser Glu Glu Ser
145                 150                 155                 160

His Gln Pro Val Ile Pro Pro Gln Pro Pro Ala Pro Thr Ser Glu Pro
                165                 170                 175

Lys Pro Lys Lys Gly Arg Ala Lys Asp Lys Pro Lys Gly Arg Pro Lys
            180                 185                 190

Asp Lys Pro Pro Cys Glu Pro Thr Val Ser Ser Gln Pro Pro Ser Gln
            195                 200                 205

Pro Thr Ala Met Pro Gly Gly Pro Asp Ala Pro Pro Ala Met
        210                 215                 220

Pro Gln Met Pro Pro Gly Val Ala Glu Ala Val Gln Ala Ala Val Gln
225                 230                 235                 240

Ala Ala Val Ala Ala Leu Gln Gln Gln Gln Gln His Gln Thr Gly
                245                 250                 255

Thr
```

(2) INFORMATION FOR SEQ ID NO:8:

(i) SEQUENCE CHARACTERISTICS:
      (A) LENGTH: 175 amino acids
      (B) TYPE: amino acid
      (D) TOPOLOGY: linear (ii) MOLECULE TYPE: protein (vii) IMMEDIATE SOURCE:
      (B) CLONE: tol.02

(ix) FEATURE:
      (A) NAME/KEY: Protein
      (B) LOCATION: 1..175
      (D) OTHER INFORMATION: /label= UL134

(xi) SEQUENCE DESCRIPTION: SEQ ID NO:8:

```
Met Ala Arg Thr Arg Glu Ala Ser Pro Val Pro Pro Arg Ser Pro Met
1               5                   10                  15

Pro Ser His Ile His Thr Met Ile Phe Ser Pro Ala Trp Asn Leu Lys
                20                  25                  30

Leu Arg Val Gly Lys Gly Arg Cys Thr Asp Ile Tyr Ala Leu Asp Phe
            35                  40                  45

Trp Lys Arg His Phe Leu Ala Arg Asn Val Phe Ile Val Gln Thr Leu
50                  55                  60

Arg Lys Glu Met Cys Ala Lys Ser Glu Asn Ser Leu Ser His Arg Gly
65                  70                  75                  80

Arg Val Thr Phe Arg Ser Asp Ala Ala Ala Val Val Glu Pro Arg
                85                  90                  95

Pro Arg Pro Pro Ala Arg Gln Leu Val Pro Pro Arg Pro Arg Arg Val
            100                 105                 110

Ala Ser Ala Ala Trp Arg Gly Glu Ala Arg Arg Ala Asp Arg Arg Ala
            115                 120                 125

Leu Pro Ser Ala Ala Thr Val Val Asn Ser Pro Ser Val Arg Thr
        130                 135                 140

Glu Val Cys Leu Ser Val Tyr Pro Ser Val Tyr Leu Ser Pro Tyr Leu
145                 150                 155                 160

Ser Ser Val Trp Val Pro Met Ser Val Leu Ala Ala Val Gly
                165                 170                 175
```

(2) INFORMATION FOR SEQ ID NO:9:

(i) SEQUENCE CHARACTERISTICS:
        (A) LENGTH: 328 amino acids
        (B) TYPE: amino acid
        (D) TOPOLOGY: linear (ii) MOLECULE TYPE: protein (vii) IMMEDIATE SOURCE:
        (B) CLONE: tol.03

(ix) FEATURE:
        (A) NAME/KEY: Protein
        (B) LOCATION: 1..328
        (D) OTHER INFORMATION: /label= UL135

(xi) SEQUENCE DESCRIPTION: SEQ ID NO:9:

```
Met Ser Val His Arg Pro Phe Pro Thr Arg Ser Leu Arg Phe Gln Ala
 1               5                  10                  15

Gly Glu Lys Ile Met Val Trp Ile Trp Leu Gly Ile Gly Leu Leu Gly
                20                  25                  30

Gly Thr Gly Leu Ala Ser Leu Val Leu Ala Ile Ser Leu Phe Thr Gln
                35                  40                  45

Arg Arg Gly Arg Lys Arg Ser Asp Glu Thr Ser Ser Arg Gly Arg Leu
 50                  55                  60

Pro Gly Ala Ala Ser Asp Lys Arg Gly Ala Cys Ala Cys Cys Tyr Arg
65                   70                  75                  80

Asn Pro Lys Glu Asp Val Val Glu Pro Leu Asp Leu Glu Leu Gly Leu
                85                  90                  95

Met Arg Val Asp Thr His Pro Pro Thr Pro Gln Val Pro Arg Cys Thr
                100                 105                 110

Ser Leu Tyr Ile Gly Glu Asp Gly Leu Pro Ile Asp Lys Pro Glu Phe
                115                 120                 125

Pro Pro Ala Arg Phe Glu Ile Pro Asp Val Ser Thr Pro Gly Thr Pro
130                 135                 140

Thr Ser Ile Gly Arg Ser Pro Ser His Cys Ser Ser Ser Ser Ser Leu
145                 150                 155                 160

Ser Ser Ser Thr Ser Val Asp Thr Val Leu Tyr Gln Pro Pro Pro Ser
                165                 170                 175

Trp Lys Pro Pro Pro Pro Gly Arg Lys Arg Pro Pro Thr Pro
                180                 185                 190

Pro Val Arg Ala Pro Thr Thr Arg Leu Ser Ser His Arg Pro Pro Thr
                195                 200                 205

Pro Ile Pro Ala Pro Arg Lys Asn Leu Ser Thr Pro Thr Lys Lys
                210                 215                 220

Thr Pro Pro Pro Thr Lys Pro Lys Pro Val Gly Trp Thr Pro Val
225                 230                 235                 240

Thr Pro Arg Pro Phe Pro Lys Thr Pro Thr Pro Gln Lys Pro Arg
                245                 250                 255

Asn Pro Arg Leu Pro Arg Thr Val Gly Leu Glu Asn Leu Ser Lys Val
                260                 265                 270

Gly Leu Ser Cys Pro Cys Pro Arg Pro Arg Thr Pro Thr Glu Pro Thr
                275                 280                 285

Thr Leu Pro Ile Val Ser Val Ser Glu Leu Ala Pro Pro Arg Trp
                290                 295                 300

Ser Asp Ile Glu Glu Leu Leu Glu Gln Ala Val Gln Ser Val Met Lys
305                 310                 315                 320
```

```
        Asp Ala Glu Ser Met Gln Met Thr
                        325

(2) INFORMATION FOR SEQ ID NO:10:

(i) SEQUENCE CHARACTERISTICS:
         (A) LENGTH: 240 amino acids
         (B) TYPE: amino acid
         (D) TOPOLOGY: linear (ii) MOLECULE TYPE: protein (vii) IMMEDIATE SOURCE:
         (B) CLONE: tol.04

(ix) FEATURE:
         (A) NAME/KEY: Protein
         (B) LOCATION: 1..240
         (D) OTHER INFORMATION: /label= UL136

(xi) SEQUENCE DESCRIPTION: SEQ ID NO:10:

Met Ser Val Lys Gly Val Glu Met Pro Glu Met Thr Trp Asp Leu Asp
    1               5                   10                  15

Val Arg Asn Lys Trp Arg Arg Lys Ala Leu Ser Arg Ile His Arg
                20                  25                  30

Phe Trp Glu Cys Arg Leu Arg Val Trp Trp Leu Ser Asp Ala Gly Val
                    35                  40                  45

Arg Glu Thr Asp Pro Pro Arg Pro Arg Arg Pro Thr Trp Met Thr
        50                  55                  60

Ala Val Phe His Val Ile Cys Ala Val Leu Leu Thr Leu Met Ile Met
    65                  70                  75                  80

Ala Ile Gly Ala Leu Ile Ala Tyr Leu Arg Tyr Tyr His Gln Asp Ser
                    85                  90                  95

Trp Arg Asp Met Leu His Asp Leu Phe Cys Gly Cys His Tyr Pro Glu
                    100                 105                 110

Lys Cys Arg Arg His His Glu Arg Gln Arg Arg Arg Gln Ala Met
                115                 120                 125

Asp Val Pro Asp Pro Glu Leu Gly Asp Pro Ala Arg Arg Pro Leu Asn
    130                 135                 140

Gly Ala Met Tyr Tyr Gly Ser Gly Cys Arg Phe Asp Thr Val Glu Met
    145                 150                 155                 160

Val Asp Glu Thr Arg Pro Ala Pro Ala Leu Ser Ser Pro Glu Thr
                    165                 170                 175

Gly Asp Asp Ser Asn Asp Asp Ala Val Ala Gly Gly Ala Gly Gly
                180                 185                 190

Val Thr Ser Pro Ala Thr Arg Thr Thr Ser Pro Asn Ala Leu Leu Pro
                    195                 200                 205

Glu Trp Met Asp Ala Val His Val Ala Val Gln Ala Ala Val Gln Ala
    210                 215                 220

Thr Val Gln Val Ser Gly Pro Arg Glu Asn Ala Val Ser Pro Ala Thr
    225                 230                 235                 240

(2) INFORMATION FOR SEQ ID NO:11:

(i) SEQUENCE CHARACTERISTICS:
         (A) LENGTH: 96 amino acids
         (B) TYPE: amino acid
         (D) TOPOLOGY: linear (ii) MOLECULE TYPE: protein (vii) IMMEDIATE SOURCE:
         (B) CLONE: tol.05
```

```
    (ix) FEATURE:
         (A) NAME/KEY: Protein
         (B) LOCATION: 1..96
         (D) OTHER INFORMATION: /label= UL137

(xi) SEQUENCE DESCRIPTION: SEQ ID NO:11:

Met Ala Thr Ile Ser Thr Ser Ile Thr Pro Met Met Gly Asn Pro Thr
    1               5                   10                  15

Phe Ser Gly Arg Ser Ser Met Val Thr Val Leu Cys Pro Asp Leu Arg
                    20                  25                  30

Pro Ser Leu Ser Leu Leu Tyr Ser Thr Arg Ala Gly Thr Ala Pro Ser
                35                  40                  45

Thr Leu Leu Arg Ser Gly Arg Tyr Gly Val Leu Pro Arg Ala Thr Tyr
                50                  55                  60

Leu His Gly Arg Leu Asn Gly Gly Leu Asp Arg His Met His Arg Ile
    65                  70                  75                  80

His Pro Phe Trp Gln Gln Cys Val Arg Arg Arg Thr Ser Arg Gly
                    85                  90                  95

(2) INFORMATION FOR SEQ ID NO:12:

(i) SEQUENCE CHARACTERISTICS:
         (A) LENGTH: 169 amino acids
         (B) TYPE: amino acid
         (D) TOPOLOGY: linear (ii) MOLECULE TYPE: protein (vii) IMMEDIATE SOURCE:
         (B) CLONE: tol.06

(ix) FEATURE:
         (A) NAME/KEY: Protein
         (B) LOCATION: 1..169
         (D) OTHER INFORMATION: /label= UL138

(xi) SEQUENCE DESCRIPTION: SEQ ID NO:12:

Met Asp Asp Leu Pro Leu Asn Val Gly Leu Pro Ile Ile Gly Val Met
    1               5                   10                  15

Leu Val Leu Ile Val Ala Ile Leu Cys Tyr Leu Ala Tyr His Trp His
                    20                  25                  30

Asp Thr Phe Lys Leu Val Arg Met Phe Leu Ser Tyr Arg Trp Leu Ile
                35                  40                  45

Arg Cys Cys Glu Leu Tyr Gly Glu Tyr Glu Arg Phe Ala Asp Leu
        50                  55                  60

Ser Ser Leu Gly Leu Gly Ala Val Arg Arg Glu Ser Asp Arg Arg Tyr
    65                  70                  75                  80

Arg Phe Ser Glu Arg Pro Asp Glu Ile Leu Val Arg Trp Glu Glu Val
                    85                  90                  95

Ser Ser Gln Cys Ser Tyr Ala Ser Ser Arg Ile Thr Asp Arg Arg Val
                    100                 105                 110

Gly Ser Ser Ser Ser Ser Val His Val Ala Ser Gln Arg Asn Ser
                    115                 120                 125

Val Pro Pro Pro Asp Met Ala Val Thr Ala Pro Leu Thr Asp Val Asp
                    130                 135                 140

Leu Leu Lys Pro Val Thr Gly Ser Ala Thr Gln Phe Thr Thr Val Ala
    145                 150                 155                 160

Met Val His Tyr His Gln Glu Tyr Thr
                    165
```

(2) INFORMATION FOR SEQ ID NO:13:

(i) SEQUENCE CHARACTERISTICS:
        (A) LENGTH: 135 amino acids
        (B) TYPE: amino acid
        (D) TOPOLOGY: linear (ii) MOLECULE TYPE: protein (vii) IMMEDIATE SOURCE:
        (B) CLONE: tol.07

(ix) FEATURE:
        (A) NAME/KEY: Protein
        (B) LOCATION: 1..135
        (D) OTHER INFORMATION: /label= UL139

(xi) SEQUENCE DESCRIPTION: SEQ ID NO:13:

```
Met Leu Trp Ile Leu Val Leu Phe Ala Leu Ala Ala Ser Ala Ser Glu
1               5                   10                  15

Thr Thr Thr Gly Thr Ser Ser Asn Ser Ser Gln Ser Thr Ser Ala Thr
            20                  25                  30

Ala Asn Thr Thr Val Ser Thr Cys Ile Asn Ala Ser Asn Gly Ser Ser
            35                  40                  45

Trp Thr Val Pro Gln Leu Ala Leu Ala Ala Ser Gly Trp Thr Leu
    50                  55                  60

Ser Gly Leu Leu Leu Leu Phe Thr Cys Cys Phe Cys Cys Phe Trp Leu
65                  70                  75                  80

Val Arg Lys Ile Cys Ser Cys Cys Gly Asn Ser Ser Glu Ser Glu Ser
                85                  90                  95

Lys Thr Thr His Ala Tyr Thr Asn Ala Ala Phe Thr Ser Ser Asp Ala
                100                 105                 110

Thr Leu Pro Met Gly Thr Thr Gly Ser Tyr Thr Pro Pro Gln Asp Gly
            115                 120                 125

Ser Phe Pro Pro Pro Arg
            130             135
```

(2) INFORMATION FOR SEQ ID NO:14:

(i) SEQUENCE CHARACTERISTICS:
        (A) LENGTH: 114 amino acids
        (B) TYPE: amino acid
        (D) TOPOLOGY: linear (ii) MOLECULE TYPE: protein (vii) IMMEDIATE SOURCE:
        (B) CLONE: tol.08

(ix) FEATURE:
        (A) NAME/KEY: Protein
        (B) LOCATION: 1..114
        (D) OTHER INFORMATION: /label= UL140

(xi) SEQUENCE DESCRIPTION: SEQ ID NO:14:

```
Met Thr Pro Ala Gln Thr Asn Ala Thr Thr Thr Val His Pro His Asp
1               5                   10                  15

Ala Lys Asn Gly Ser Gly Gly Ser Ala Leu Pro Thr Leu Val Val Phe
                20                  25                  30

Gly Phe Ile Val Thr Leu Leu Phe Phe Leu Phe Met Leu Tyr Phe Trp
            35                  40                  45

Asn Asn Asp Val Phe Arg Lys Leu Leu Arg Ala Leu Gly Ser Ser Ala
            50                  55                  60

Val Ala Thr Ala Ser Thr Arg Gly Lys Thr Arg Ser Ser Thr Val Val
65                  70                  75                  80
```

```
    His His Val Val Pro Arg Ala Thr Thr Arg Val Val Leu Thr Ala Cys
                    85                  90                  95

His Arg Thr Phe Phe Tyr His Pro Arg Pro Met Ala Val Leu Thr Thr
                    100                 105                 110

Arg His
```

(2) INFORMATION FOR SEQ ID NO:15:

(i) SEQUENCE CHARACTERISTICS:
        (A) LENGTH: 425 amino acids
        (B) TYPE: amino acid
        (D) TOPOLOGY: linear (ii) MOLECULE TYPE: protein (vii) IMMEDIATE SOURCE:
        (B) CLONE: tol.09

(ix) FEATURE:
        (A) NAME/KEY: Protein
        (B) LOCATION: 1..425
        (D) OTHER INFORMATION: /label= UL141

(xi) SEQUENCE DESCRIPTION: SEQ ID NO:15:

```
    Met Arg Gln Val Ala Tyr Arg Arg Arg Glu Ser Ser Cys Ala Val
    1               5                   10                  15

Leu Val His His Val Gly Arg Asp Gly Asp Gly Glu Gly Glu Ala Ala
                    20                  25                  30

Lys Lys Thr Cys Lys Lys Thr Gly Arg Ser Val Ala Gly Ile Pro Gly
                    35                  40                  45

Glu Lys Leu Arg Arg Thr Val Val Thr Thr Thr Pro Ala Arg Arg Leu
                    50                  55                  60

Ser Gly Arg His Thr Glu Gln Glu Gln Ala Gly Met Arg Leu Cys Glu
    65                  70                  75                  80

Lys Gly Lys Lys Arg Ile Ile Met Cys Arg Arg Glu Ser Leu Arg Thr
                    85                  90                  95

Leu Pro Trp Leu Phe Trp Val Leu Leu Ser Cys Pro Arg Leu Leu Glu
                    100                 105                 110

Tyr Ser Ser Ser Ser Phe Pro Phe Ala Thr Ala Asp Ile Ala Glu Lys
                    115                 120                 125

Met Trp Ala Glu Asn Tyr Glu Thr Thr Ser Pro Ala Pro Val Leu Val
                    130                 135                 140

Ala Glu Gly Glu Gln Val Thr Ile Pro Cys Thr Val Met Thr His Ser
    145                 150                 155                 160

Trp Pro Met Val Ser Ile Arg Ala Arg Phe Cys Arg Ser His Asp Gly
                    165                 170                 175

Ser Asp Glu Leu Ile Leu Asp Ala Val Lys Gly His Arg Leu Met Asn
                    180                 185                 190

Gly Leu Gln Tyr Arg Leu Pro Tyr Ala Thr Trp Asn Phe Ser Gln Leu
                    195                 200                 205

His Leu Gly Gln Ile Phe Ser Leu Thr Phe Asn Val Ser Met Asp Thr
                    210                 215                 220

Ala Gly Met Tyr Glu Cys Val Leu Arg Asn Tyr Ser His Gly Leu Ile
    225                 230                 235                 240

Met Gln Arg Phe Val Ile Leu Thr Gln Leu Glu Thr Leu Ser Arg Pro
                    245                 250                 255

Asp Glu Pro Cys Cys Thr Pro Ala Leu Gly Arg Tyr Ser Leu Gly Asp
                    260                 265                 270
```

```
          Gln Ile Trp Ser Pro Thr Pro Trp Arg Leu Arg Asn His Asp Cys Gly
                  275                 280                 285

Thr Tyr Arg Gly Phe Gln Arg Asn Tyr Phe Tyr Ile Gly Arg Ala Asp
                  290                 295                 300

Ala Glu Asp Cys Trp Lys Pro Ala Cys Pro Asp Glu Pro Asp Arg
          305                 310                 315                 320

Cys Trp Thr Val Ile Gln Arg Tyr Arg Leu Pro Gly Asp Cys Tyr Arg
                          325                 330                 335

Ser Gln Pro His Pro Pro Lys Phe Leu Pro Val Thr Pro Ala Pro Pro
                          340                 345                 350

Ala Asp Ile Asp Thr Gly Met Ser Pro Trp Ala Thr Arg Gly Ile Ala
                          355                 360                 365

Ala Phe Leu Gly Phe Trp Ser Ile Phe Thr Val Cys Phe Leu Cys Tyr
                          370                 375                 380

Leu Cys Tyr Leu Gln Cys Cys Gly Arg Trp Cys Pro Thr Pro Gly Arg
          385                 390                 395                 400

Gly Arg Arg Gly Gly Glu Gly Tyr Arg Leu Pro Thr Tyr Asp Ser
                          405                 410                 415

Tyr Pro Gly Val Arg Lys Met Lys Arg
                          420                 425
```

(2) INFORMATION FOR SEQ ID NO:16:

(i) SEQUENCE CHARACTERISTICS:
       (A) LENGTH: 306 amino acids
       (B) TYPE: amino acid
       (D) TOPOLOGY: linear (ii) MOLECULE TYPE: protein (vii) IMMEDIATE SOURCE:
        (B) CLONE: tol.10

(ix) FEATURE:
        (A) NAME/KEY: Protein
        (B) LOCATION: 1..306
        (D) OTHER INFORMATION: /label= UL142

(xi) SEQUENCE DESCRIPTION: SEQ ID NO:16:

```
          Met Arg Ile Glu Trp Val Trp Trp Leu Phe Gly Tyr Phe Val Ser Ser
          1               5                  10                  15

Val Gly Ser Glu Arg Ser Leu Ser Tyr Arg Tyr His Leu Glu Ser Asn
                          20                  25                  30

Ser Ser Thr Asn Val Val Cys Asn Gly Asn Ile Ser Val Phe Val Asn
                          35                  40                  45

Gly Thr Leu Gly Val Arg Tyr Asn Ile Thr Val Gly Ile Ser Ser Ser
                  50                  55                  60

Leu Leu Ile Gly His Leu Thr Ile Gln Val Leu Glu Ser Trp Phe Thr
          65                  70                  75                  80

Pro Trp Val Gln Asn Lys Ser Tyr Asn Lys Gln Pro Leu Gly Asp Thr
                          85                  90                  95

Glu Thr Leu Tyr Asn Ile Asp Ser Glu Asn Ile His Arg Val Ser Gln
                          100                 105                 110

Tyr Phe His Thr Arg Trp Ile Lys Ser Leu Gln Glu Asn His Thr Cys
                          115                 120                 125

Asp Leu Thr Asn Ser Thr Pro Thr Tyr Thr Tyr Gln Val Asn Val Asn
                  130                 135                 140

Asn Thr Asn Tyr Leu Thr Leu Thr Ser Ser Gly Trp Gln Asp Arg Leu
          145                 150                 155                 160
```

```
    Asn Tyr Thr Val Ile Asn Ser Thr His Phe Asn Leu Thr Glu Ser Asn
                    165                 170                 175

Ile Thr Ser Ile Gln Lys Tyr Leu Asn Thr Thr Cys Ile Glu Arg Leu
                180                 185                 190

Arg Asn Tyr Thr Leu Glu Ser Val Tyr Thr Thr Thr Val Pro Gln Asn
            195                 200                 205

Ile Thr Thr Ser Gln His Ala Thr Thr Thr Met His Thr Ile Pro Pro
        210                 215                 220

Asn Thr Ile Thr Ile Gln Asn Thr Thr Gln Ser His Thr Val Gln Thr
    225                 230                 235                 240

Pro Ser Phe Asn Asp Thr His Asn Val Thr Lys His Thr Leu Asn Ile
                    245                 250                 255

Ser Tyr Val Leu Ser Gln Lys Thr Asn Asn Thr Thr Ser Pro Trp Ile
                260                 265                 270

Tyr Ala Ile Pro Met Gly Ala Thr Ala Thr Ile Gly Ala Gly Leu Tyr
                275                 280                 285

Ile Gly Lys His Phe Thr Pro Val Lys Phe Val Tyr Glu Val Trp Arg
                290                 295                 300

Gly Gln
    305
```

(2) INFORMATION FOR SEQ ID NO:17:

(i) SEQUENCE CHARACTERISTICS:
      (A) LENGTH: 92 amino acids
      (B) TYPE: amino acid
      (D) TOPOLOGY: linear (ii) MOLECULE TYPE: protein (vii) IMMEDIATE SOURCE:
      (B) CLONE: tol.11

(ix) FEATURE:
      (A) NAME/KEY: Protein
      (B) LOCATION: 1..92
      (D) OTHER INFORMATION: /label= UL143

(xi) SEQUENCE DESCRIPTION: SEQ ID NO:17:

```
    Met Ala Arg Ser Val Lys Thr Ile Arg Ile Gln His Ile Tyr Ser Pro
    1               5                   10                  15

Arg Ser Ser Asn Thr Leu Gln His Met Ser Lys Lys Gln Glu Ser Ile
                20                  25                  30

Ala Thr Ile Thr Phe Gly Arg Ile Thr Cys Cys His Pro Leu Ala Ser
                35                  40                  45

Ile Asn Leu Met Phe Asn Gly Ser Cys Thr Val Thr Val Lys Ile Ser
            50                  55                  60

Met Gly Ile Asn Gly Ser Thr Asn Val His Gln Leu Val Ile Val Leu
    65                  70                  75                  80

His Leu Gly Asn Arg Cys Gln Pro Trp Arg Gln Val
                    85                  90
```

(2) INFORMATION FOR SEQ ID NO:18:

(i) SEQUENCE CHARACTERISTICS:
      (A) LENGTH: 176 amino acids
      (B) TYPE: amino acid
      (D) TOPOLOGY: linear (ii) MOLECULE TYPE: protein (vii) IMMEDIATE SOURCE:
      (B) CLONE: tol.12

```
     (ix) FEATURE:
           (A) NAME/KEY: Protein
           (B) LOCATION: 1..176
           (D) OTHER INFORMATION: /label= UL144

(xi) SEQUENCE DESCRIPTION: SEQ ID NO:18:

Met Lys Pro Leu Ile Met Leu Ile Cys Phe Ala Val Ile Leu Leu Gln
     1               5                   10                  15

Leu Gly Val Thr Lys Val Cys Gln His Asn Glu Val Gln Leu Gly Asn
                     20                  25                  30

Glu Cys Cys Pro Pro Cys Gly Ser Gly Gln Arg Val Thr Lys Val Cys
                 35                  40                  45

Thr Asp Tyr Thr Ser Val Thr Cys Thr Pro Cys Pro Asn Gly Thr Tyr
             50                  55                  60

Val Ser Gly Leu Tyr Asn Cys Thr Asp Cys Thr Gln Cys Asn Val Thr
     65                  70                  75                  80

Gln Val Met Ile Arg Asn Cys Thr Ser Thr Asn Asn Thr Val Cys Ala
                         85                  90                  95

Pro Lys Asn His Thr Tyr Phe Ser Thr Pro Gly Val Gln His His Lys
                     100                 105                 110

Gln Arg Gln Gln Asn His Thr Ala His Ile Thr Val Lys Gln Gly Lys
                 115                 120                 125

Ser Gly Arg His Thr Leu Ala Trp Leu Ser Leu Phe Ile Phe Leu Val
             130                 135                 140

Gly Ile Ile Leu Leu Ile Leu Tyr Leu Ile Ala Ala Tyr Arg Ser Glu
     145                 150                 155                 160

Arg Cys Gln Gln Cys Cys Ser Ile Gly Lys Ile Phe Tyr Arg Thr Leu
                         165                 170                 175

(2) INFORMATION FOR SEQ ID NO:19:

(i) SEQUENCE CHARACTERISTICS:
           (A) LENGTH: 100 amino acids
           (B) TYPE: amino acid
           (D) TOPOLOGY: linear (ii) MOLECULE TYPE: protein (vii) IMMEDIATE SOURCE:
           (B) CLONE: tol.13

(ix) FEATURE:
           (A) NAME/KEY: Protein
           (B) LOCATION: 1..100
           (D) OTHER INFORMATION: /label= UL145

(xi) SEQUENCE DESCRIPTION: SEQ ID NO:19:

Met Cys Thr Asp Pro Arg Arg Thr Ala Gly Trp Glu Arg Leu Thr His
     1               5                   10                  15

His Ala Ser Tyr His Ala Asn Tyr Gly Ala Tyr Ala Val Leu Met Ala
                     20                  25                  30

Thr Ser Gln Arg Lys Ser Leu Val Leu His Arg Tyr Ser Ala Val Thr
                 35                  40                  45

Ala Val Ala Leu Gln Leu Met Pro Val Glu Ile Val Arg Lys Leu Asp
             50                  55                  60

Gln Ser Asp Trp Val Arg Gly Ala Trp Ile Val Ser Glu Thr Phe Pro
     65                  70                  75                  80

Thr Ser Asp Pro Lys Gly Val Trp Ser Asp Asp Ser Ser Met Gly
                         85                  90                  95
```

```
     Gly Ser Asp Asp
             100

(2) INFORMATION FOR SEQ ID NO:20:

(i) SEQUENCE CHARACTERISTICS:
        (A) LENGTH: 117 amino acids
        (B) TYPE: amino acid
        (D) TOPOLOGY: linear (ii) MOLECULE TYPE: protein (vii) IMMEDIATE SOURCE:
        (B) CLONE: tol.14

(ix) FEATURE:
        (A) NAME/KEY: Protein
        (B) LOCATION: 1..117
        (D) OTHER INFORMATION: /label= UL146

(xi) SEQUENCE DESCRIPTION: SEQ ID NO:20:

Met Arg Leu Ile Phe Gly Ala Leu Ile Ile Phe Leu Ala Tyr Val Tyr
     1               5                  10                  15

His Tyr Glu Val Asn Gly Thr Glu Leu Arg Cys Arg Cys Leu His Arg
                 20                  25                  30

Lys Trp Pro Pro Asn Lys Ile Ile Leu Gly Asn Tyr Trp Leu His Arg
             35                  40                  45

Asp Pro Arg Gly Pro Gly Cys Asp Lys Asn Glu His Leu Leu Tyr Pro
         50                  55                  60

Asp Gly Arg Lys Pro Pro Gly Pro Gly Val Cys Leu Ser Pro Asp His
     65                  70                  75                  80

Leu Phe Ser Lys Trp Leu Asp Lys His Asn Asp Asn Arg Trp Tyr Asn
                     85                  90                  95

Val Asn Ile Thr Lys Ser Pro Gly Pro Arg Arg Ile Asn Ile Thr Leu
                 100                 105                 110

Ile Gly Val Arg Gly
             115

(2) INFORMATION FOR SEQ ID NO:21:

(i) SEQUENCE CHARACTERISTICS:
        (A) LENGTH: 159 amino acids
        (B) TYPE: amino acid
        (D) TOPOLOGY: linear (ii) MOLECULE TYPE: protein (vii) IMMEDIATE SOURCE:
        (B) CLONE: tol.15

(ix) FEATURE:
        (A) NAME/KEY: Protein
        (B) LOCATION: 1..159
        (D) OTHER INFORMATION: /label= UL147

(xi) SEQUENCE DESCRIPTION: SEQ ID NO:21:

Met Val Leu Thr Trp Leu His His Pro Val Ser Asn Ser His Ile Asn
     1               5                  10                  15

Leu Leu Ser Val Arg His Leu Ser Leu Ile Ala Tyr Met Leu Leu Thr
                 20                  25                  30

Ile Cys Pro Leu Ala Val His Val Leu Glu Leu Glu Asp Tyr Asp Arg
             35                  40                  45

Arg Cys Arg Cys Asn Asn Gln Ile Leu Leu Asn Thr Leu Pro Val Gly
         50                  55                  60
```

```
Thr Glu Leu Leu Lys Pro Ile Ala Ala Ser Glu Ser Cys Asn Arg Gln
 65                  70                  75                  80

Glu Val Leu Ala Ile Leu Lys Asp Lys Gly Thr Lys Cys Leu Asn Pro
                 85                  90                  95

Asn Ala Gln Ala Val Arg Arg His Ile Asn Arg Leu Phe Phe Arg Leu
             100                 105                 110

Ile Leu Asp Glu Glu Gln Arg Ile Tyr Asp Val Val Ser Thr Asn Ile
         115                 120                 125

Glu Phe Gly Ala Trp Pro Val Pro Thr Ala Tyr Lys Ala Phe Leu Trp
     130                 135                 140

Lys Tyr Ala Lys Arg Leu Asn Tyr His His Phe Arg Leu Arg Trp
145                 150                 155
```

(2) INFORMATION FOR SEQ ID NO:22:

(i) SEQUENCE CHARACTERISTICS:
        (A) LENGTH: 316 amino acids
        (B) TYPE: amino acid
        (D) TOPOLOGY: linear (ii) MOLECULE TYPE: protein (vii) IMMEDIATE SOURCE:
        (B) CLONE: tol.16

(ix) FEATURE:
        (A) NAME/KEY: Protein
        (B) LOCATION: 1..316
        (D) OTHER INFORMATION: /label= UL148

(xi) SEQUENCE DESCRIPTION: SEQ ID NO:22:

```
Met Leu Arg Leu Leu Phe Thr Leu Val Leu Ala Leu His Gly Gln
  1               5                  10                  15

Ser Val Gly Ala Ser Arg Asp Tyr Val His Val Arg Leu Leu Ser Tyr
             20                  25                  30

Arg Gly Asp Pro Leu Val Phe Lys His Thr Phe Ser Gly Val Arg Arg
         35                  40                  45

Pro Phe Thr Glu Leu Gly Trp Ala Ala Cys Arg Asp Trp Asp Ser Met
     50                  55                  60

His Cys Thr Pro Phe Trp Ser Thr Asp Leu Glu Gln Met Thr Asp Ser
 65                  70                  75                  80

Val Arg Arg Tyr Ser Thr Val Ser Pro Gly Lys Glu Val Thr Leu Gln
                 85                  90                  95

Leu His Gly Asn Gln Thr Val Gln Pro Ser Phe Leu Ser Phe Thr Cys
             100                 105                 110

Arg Leu Gln Leu Glu Pro Val Val Glu Asn Val Gly Leu Tyr Val Ala
         115                 120                 125

Tyr Val Val Asn Asp Gly Glu Arg Pro Gln Gln Phe Phe Thr Pro Gln
     130                 135                 140

Val Asp Val Val Arg Phe Ala Leu Tyr Leu Glu Thr Leu Ser Arg Ile
145                 150                 155                 160

Val Glu Pro Leu Glu Ser Gly Arg Leu Ala Val Glu Phe Asp Thr Pro
                165                 170                 175

Asp Leu Ala Leu Ala Pro Asp Leu Val Ser Ser Leu Phe Val Ala Gly
            180                 185                 190

His Gly Glu Thr Asp Phe Tyr Met Asn Trp Thr Leu Arg Arg Ser Gln
        195                 200                 205

Thr His Tyr Leu Glu Glu Met Ala Leu Gln Val Glu Ile Leu Lys Pro
    210                 215                 220
```

```
Arg Gly Val Arg His Arg Ala Ile Ile His His Pro Lys Leu Gln Pro
225                 230                 235                 240

Gly Val Gly Leu Trp Ile Asp Phe Cys Val Tyr Arg Tyr Asn Ala Arg
                245                 250                 255

Leu Thr Arg Gly Tyr Val Arg Tyr Thr Leu Ser Pro Lys Ala Arg Leu
            260                 265                 270

Pro Ala Lys Ala Glu Gly Trp Leu Val Ser Leu Asp Arg Phe Ile Val
        275                 280                 285

Gln Tyr Leu Asn Thr Leu Leu Ile Thr Met Met Ala Ala Ile Trp Ala
    290                 295                 300

Arg Val Leu Ile Thr Tyr Leu Val Ser Arg Arg
305                 310                 315
```

(2) INFORMATION FOR SEQ ID NO:23:

(i) SEQUENCE CHARACTERISTICS:
        (A) LENGTH: 214 amino acids
        (B) TYPE: amino acid
        (D) TOPOLOGY: linear (ii) MOLECULE TYPE: protein (vii) IMMEDIATE SOURCE:
        (B) CLONE: tol.19

(ix) FEATURE:
        (A) NAME/KEY: Protein
        (B) LOCATION: 1..214
        (D) OTHER INFORMATION: /label= UL130

(xi) SEQUENCE DESCRIPTION: SEQ ID NO:23:

```
Met Leu Arg Leu Leu Arg His His Phe His Cys Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Gln Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Val Ile Trp
            100                 105                 110

Tyr Leu Ser Gly Arg Asn Gln Thr Ile Leu Gln Arg Met Pro Gln Thr
    115                 120                 125

Ala Ser Lys Pro Ser Asp Gly Asn Val Gln Ile Ser Val Glu Asp Ala
130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
    195                 200                 205

His Pro Asn Leu Ile Ile
    210
```

(2) INFORMATION FOR SEQ ID NO:24:

(i) SEQUENCE CHARACTERISTICS:
        (A) LENGTH: 122 amino acids
        (B) TYPE: amino acid
        (D) TOPOLOGY: linear (ii) MOLECULE TYPE: protein (vii) IMMEDIATE SOURCE:
        (B) CLONE: tol.20

(ix) FEATURE:
        (A) NAME/KEY: Protein
        (B) LOCATION: 1..122
        (D) OTHER INFORMATION: /label= UL149

(xi) SEQUENCE DESCRIPTION: SEQ ID NO:24:

```
Met Val Asp Gln Cys Cys Tyr Arg His Leu His Arg Ser Leu Ser Gly
 1               5                  10                  15

Gly Pro Asp Val Leu Tyr Ala Ala Gly Thr Gln Arg Glu Gln Gln
             20                  25                  30

Arg Leu Asp Lys Ser Leu Ala Ala Thr Ala Pro Ser Ala Val Ala Gly
             35                  40                  45

Pro Pro Ala Asp Arg Asp Val Val Asp His Arg Thr Glu Thr His Ala
 50                      55                  60

Tyr Glu Thr Pro Arg Tyr Ala Thr Arg Cys Leu Thr Arg Tyr Thr Thr
 65                  70                  75                  80

Pro Val Arg Ser Ala Val Arg Arg Thr Thr Cys Gly Lys Arg Val Ala
                 85                  90                  95

Ser Gln Ser Pro Pro Arg Ser Cys Leu Val Ala Pro Gln Ser Ser Pro
            100                 105                 110

Ala His Pro Pro Arg His Pro Glu Gly Gly
            115                 120
```

(2) INFORMATION FOR SEQ ID NO:25:

(i) SEQUENCE CHARACTERISTICS:
        (A) LENGTH: 642 amino acids
        (B) TYPE: amino acid
        (D) TOPOLOGY: linear (ii) MOLECULE TYPE: protein (vii) IMMEDIATE SOURCE:
        (B) CLONE: tol.21

(ix) FEATURE:
        (A) NAME/KEY: Protein
        (B) LOCATION: 1..642
        (D) OTHER INFORMATION: /label= UL150

(xi) SEQUENCE DESCRIPTION: SEQ ID NO:25:

```
Met Gln Leu Cys Ser His Ser Ile Ser Ser Gln Arg His Val Ala Ser
 1               5                  10                  15

Ser Met His Cys Arg Ser Arg His Gln Arg Thr Pro Pro Ser Ala Thr
             20                  25                  30

Thr His Gly Pro Cys Ala Pro Thr Ser Arg Ile Leu Arg Arg Leu Leu
             35                  40                  45

Thr Thr Arg Arg Phe Leu Pro Arg Thr Pro Ser Pro Ser Asn Thr Val
 50                      55                  60

Cys Cys Ile Arg Arg Arg Leu His Glu Arg Thr Ile Arg His Ser Met
 65                  70                  75                  80
```

```
Arg Cys Arg Arg Arg Asp Met Ala Ser Ser Ala Ser Thr Pro Val Ser
                85                  90                  95

His Thr Gln Pro Leu Ala Ala Asn His Arg Arg Ser Arg Ile Thr Tyr
            100                 105                 110

Ala Thr Thr Asp Pro Thr Asn Ser Pro Thr Ala Ser Pro Ala Lys Ser
        115                 120                 125

Asp Lys Leu Glu Ala Asp Ala Asp Pro Ala Leu His Arg Arg Pro Ala
    130                 135                 140

Ser Leu Leu Arg His Leu Phe Gln Pro Cys His Ala Gln Arg Gly Thr
145                 150                 155                 160

Ser Asn Arg Ala Thr Ser Gln Arg Ala Ser Leu Asn Ala Val His His
                165                 170                 175

Lys Leu Cys Gly Ala Met Ile Ser Ser Cys Ser Thr Thr Cys Thr
            180                 185                 190

Pro Leu Ile Met Asp Leu Pro Ser Leu Ser Val Glu Leu Ser Ala Gly
        195                 200                 205

His Lys Lys Lys Glu Thr Pro Thr Glu Gly Gly Trp Gly Gly Glu Glu
    210                 215                 220

Gly Glu Asp Asp Val Leu Ala Thr Ile Arg Asn Thr Leu Ser Ala Pro
225                 230                 235                 240

Thr Ser Pro Ala Ala Ala Thr Thr His Arg Leu Ser Phe Pro Gly Glu
                245                 250                 255

Ser Thr Phe Cys Leu Thr Ala Val Ser Glu Cys Ser Gln Arg Arg Thr
            260                 265                 270

Ser Thr Ala Ala Leu Thr Pro Pro Pro Ala Val Ala Ala Ala Phe
        275                 280                 285

Ser Phe Ser Ser Thr Val Ser Glu Thr Gly Thr Phe Pro Gln Ser Thr
    290                 295                 300

Thr Gly Arg Thr Arg Val Asp Asp Thr Ala Val Val Thr Ala Gly Asp
305                 310                 315                 320

Pro Arg Ser Pro Val Thr His Val Thr Leu Leu Gln Ile Phe Arg Leu
                325                 330                 335

Arg Ser Ser Leu Leu Thr Ser Arg Ser Gly Gly Ala Leu Arg Gly Gly
            340                 345                 350

Glu His Glu Ala Ile Pro Lys Val Ala Ser Leu Phe Trp Thr Leu Leu
        355                 360                 365

Lys Ala Thr Gln Ile Val Glu Met Thr His Lys Thr Pro Ser Ala Asp
    370                 375                 380

Ser His Arg Asn Pro Gln Lys Tyr Thr Asp Arg Pro Gln Arg Leu Leu
385                 390                 395                 400

Leu Thr Ala Leu Ala Ile Trp Gln Arg Thr Tyr Asn Asp Thr Arg Ala
                405                 410                 415

Ala His Ala Pro Gln Val Arg Leu Leu Gly Asp Ile Leu Thr Tyr Arg
            420                 425                 430

Arg Pro Gln Thr Ala Thr Ala Ser Thr Lys Ala His Thr Gln Gln Gln
        435                 440                 445

Pro Glu Glu Pro Lys Gly Gln Gln Ile Trp Thr Gln Thr Ala Gly Gln
    450                 455                 460

Ala Ala Pro His Gly Asp Glu Pro His Ser Asp Gly Glu Leu Arg Arg
465                 470                 475                 480

Glu Ser His Ser Ala Pro Pro Thr Ser Arg Thr Leu Pro Asp Thr Ile
                485                 490                 495

Leu Ala Val Lys Arg Arg Ser Val Ala Gln Arg Ser His Val Arg Leu
            500                 505                 510
```

```
Asp Ala Lys Pro Gly Leu Asn Glu Arg Asp Gly Phe Arg Gln Arg Leu
    515                 520                 525

Leu Leu Pro Leu Ser Gly Tyr Phe Arg Ala Asn Glu Leu Arg Asn Gln
    530                 535                 540

Gln Phe Met Gly Tyr Gly Thr Lys Asn Gly Leu Lys Asn Thr Trp Leu
545                 550                 555                 560

Thr Arg Pro Leu Gly Val Ala Gly Gly Val Arg Glu Thr Ile Gly Glu
                565                 570                 575

Arg Gln Asp Arg Asn Val Ala Asp Ser Ala Thr Gln Arg Val Phe His
                580                 585                 590

Thr Leu Tyr Ala Ala Leu Gln Thr Val Arg Val Trp Tyr Thr Ala Leu
            595                 600                 605

Gly Thr Ala Trp Arg Thr Ser Gly Ser Arg Thr Arg Glu Ser Leu Phe
            610                 615                 620

Asp Gly Pro Arg Arg Asp Arg Gln Ala Ala Arg Leu Arg Arg Leu
625                 630                 635                 640

Glu Leu
```

(2) INFORMATION FOR SEQ ID NO:26:

(i) SEQUENCE CHARACTERISTICS:
        (A) LENGTH: 336 amino acids
        (B) TYPE: amino acid
        (D) TOPOLOGY: linear (ii) MOLECULE TYPE: protein (vii) IMMEDIATE SOURCE:
        (B) CLONE: tol.22

(ix) FEATURE:
        (A) NAME/KEY: Protein
        (B) LOCATION: 1..336
        (D) OTHER INFORMATION: /label= UL151

(xi) SEQUENCE DESCRIPTION: SEQ ID NO:26:

```
Met Val Phe Val Ser Gly Thr Ala Leu Gly Thr Gly Phe His Arg Ala
1               5                   10                  15

Glu Gly Ser Phe Cys Gly Cys Glu Gly Arg Ser Phe Pro Arg Thr Leu
                20                  25                  30

Gly Thr Gly Leu Gly Asp Gly Gly Cys Ala Gly Arg Arg Trp Xaa Arg
            35                  40                  45

Xaa Val Ala Gly Thr Gly Ile Thr Leu Gly Thr Gly Thr Arg Gly Pro
    50                  55                  60

Gly Leu Arg Asp Gly Gly Asp Gly Gly Val Cys Gly Glu Asp Gly Gly
65                  70                  75                  80

Leu Leu Arg Arg Gly Arg Gly Leu Ala Gly Pro Ala Val Ala Gly Val
                85                  90                  95

Cys Gly Asp Gly Gly Leu Leu Gln Arg Arg Gly Leu Arg Gly Gln Glu
                100                 105                 110

Cys Ala Xaa Pro Gly Gly Phe Ala Gly Gly His Gly Thr Gly Gly Gly
            115                 120                 125

Gly Asp Ser Thr Asn His Thr His Thr Gln Leu Thr Ser Ala Val Ala
            130                 135                 140

Leu Ser Glu Pro Pro Leu Phe Phe Ile Asn Val Leu Ile Pro Pro Ala
145                 150                 155                 160

Tyr Thr Arg Asn Ala Ala Cys Ser Tyr Ala His Thr Leu Ser Leu His
                165                 170                 175
```

```
          Ser Asp Met Leu Leu Arg Leu Cys Thr Ala Ala Ala Asp Thr Ser Gly
                      180                 185                 190

His Arg His Leu Pro Pro His Met Ala His Val Leu Arg Arg Pro Ala
                      195                 200                 205

Ser Tyr Val Val Cys Ser Gln His Gly Ala Phe Phe Pro Ala Arg His
                      210                 215                 220

Leu His Arg Thr Pro Ser Ala Ala Phe Ala Val Ala Ser Thr Arg Glu
          225                 230                 235                 240

Gln Tyr Ala Thr Ala Cys Ala Val Ala Ala Thr Trp Pro Pro Arg
                                  245                 250                 255

Leu Pro His Leu Phe Arg Thr Pro Asn Leu Trp Leu Pro Thr Thr Asp
                      260                 265                 270

Val Gln Gly Ser Arg Thr Arg Arg Pro Ile Pro Ile Leu Gln Arg
                          275                 280                 285

Pro Arg Pro Pro Ser Gln Thr Ser Trp Lys Pro Thr Gln Thr Gln His
                      290                 295                 300

Ser Ile Asp Ala Arg Pro Arg Cys Cys Ala Thr Ser Ser Pro Ala
          305                 310                 315                 320

Thr Pro Asn Ala Ala Leu Pro Thr Glu Pro His Pro Arg Gly Leu Pro
                      325                 330                 335

(2) INFORMATION FOR SEQ ID NO:27:

(i) SEQUENCE CHARACTERISTICS:
          (A) LENGTH: 270 amino acids
          (B) TYPE: amino acid
          (D) TOPOLOGY: linear (ii) MOLECULE TYPE: protein (vii) IMMEDIATE SOURCE:
          (B) CLONE: tol.23

(ix) FEATURE:
          (A) NAME/KEY: Protein
          (B) LOCATION: 1..270
          (D) OTHER INFORMATION: /label= UL132

(xi) SEQUENCE DESCRIPTION: SEQ ID NO:27:

Met Pro Ala Leu Arg Gly Pro Leu Arg Ala Thr Phe Leu Ala Leu Val
          1               5                   10                  15

Ala Phe Gly Leu Leu Leu Gln Ile Asp Leu Ser Asp Ala Thr Asn Val
                          20                  25                  30

Thr Ser Ser Thr Lys Val Pro Thr Ser Thr Ser Asn Arg Asn Asn Val
                      35                  40                  45

Asp Asn Ala Thr Ser Ser Gly Pro Thr Thr Gly Ile Asn Met Thr Thr
          50                  55                  60

Thr His Glu Ser Ser Val His Asn Val Arg Asn Asn Glu Ile Met Lys
          65                  70                  75                  80

Val Leu Ala Ile Leu Phe Tyr Ile Val Thr Gly Thr Ser Ile Phe Ser
                          85                  90                  95

Phe Ile Ala Val Leu Ile Ala Val Val Tyr Ser Ser Cys Cys Lys His
                      100                 105                 110

Pro Gly Arg Phe Arg Phe Ala Asp Glu Glu Ala Val Asn Leu Leu Asp
                      115                 120                 125

Asp Thr Asp Asp Ser Gly Gly Ser Ser Pro Phe Gly Ser Gly Ser Arg
          130                 135                 140

Arg Gly Ser Gln Ile Pro Ala Gly Phe Cys Ser Ser Ser Pro Tyr Gln
          145                 150                 155                 160
```

```
Arg Leu Glu Thr Arg Asp Trp Asp Glu Glu Glu Ala Ser Ala Ala
            165             170             175

Arg Glu Arg Met Lys His Asp Pro Glu Asn Val Ile Tyr Phe Arg Lys
            180             185             190

Asp Gly Asn Leu Asp Thr Ser Phe Val Asn Pro Asn Tyr Gly Arg Gly
        195             200             205

Ser Pro Leu Thr Ile Glu Ser His Leu Ser Asp Asn Glu Glu Asp Pro
    210             215             220

Ile Arg Tyr Tyr Val Ser Val Tyr Asp Glu Leu Thr Ala Ser Glu Met
225             230             235             240

Glu Glu Pro Ser Asn Ser Thr Ser Trp Gln Ile Pro Lys Leu Met Lys
            245             250             255

Val Ala Met Gln Pro Val Ser Leu Arg Asp Pro Glu Tyr Asp
            260             265             270
```

HUMAN CYTOMEGALOVIRUS DNA SEQUENCES

This is a divisional of application U.S. Ser. No. 08/414,926 filed on Mar. 31, 1995, U.S. Pat. No. 5,721,354.

TECHNICAL FIELD

This invention pertains to the field of virology, specifically to the diagnosis, treatment and prevention of viral infections in humans. More specifically, this invention relates to the diagnosis, treatment and prevention of human cytomegalovirus infections.

BACKGROUND

Human cytomegalovirus (HCMV) is a ubiquitous agent in human populations. Infections are generally asymptomatic, but there can be serious medical sequelae in immunocompromised individuals and in congenitally infected newborns. In immunocompromised individuals, HCMV infection can result in interstitial pneumonia, retinitis progressing to blindness and disseminated infection. Infections in newborns can be severely damaging, with multiple organ involvement including the central nervous system and may also result in auditory damage. The mechanisms of pathogenesis are not understood, although it is believed that host factors, such as cellular and/or hmunoral immune responses might be involved. See, Alford and Britt, "The Humnan Herpesviruses", eds Roizman, B., R. J. Whitley and C. Lopez, Raven Press, New York, 1993, pp 227–55. It has also been speculated that genetic variability (either structural or antigenic or both) among different strains of HCMV could be responsible for the variance in clinical manifestations observed. Pritchett, *J. Virol.* 36:152–61(1980), Lehner, *J. Clin. Microbiol.* 29:249–2502(1991); Fries, *J. Infect. Dis.* 169:769–74(1994).

Considerable attention has been focused recently on the analysis of strain variation among HCMV isolates. Some twenty different HCMV strains have been isolated and differentiated by restriction analysis of PCR amplified DNA fragments. Chou, *J. Infect. Dis.* 162:738–42(1990).

One strain, the Towne strain, has been developed into a live, attenuated vaccine and administered with some success in renal transplant patients. See Quinnan, *Annals of Int. Med.* 101:478–83(1984); Plotkin, *Lancet* 1:528–30(1984). However, Towne strain vaccines who were directly challenged by low-passaged Toledo strain wild-type virus in one study were found to resist challenge doses of only 10 plaque-forming units (pfu) or less. Plotkin, *J. Infect. Dis.* 159:860–65(1989). Therefore, it appears the Towne strain may be overly attenuated, i.e., genetically modified so extensively resulting from serial passage in cell culture that it has lost significant immunogenicity presumably due to the loss of genetic information during the cell passage. Advantageously however, the Towne strain has never been shown to reactivate.

DNA sequence heterogeneity between the Towne strain and another strain of HCMV, AD169, has been found. Pritchett, *J. Virol.* 36:152–61(1980). (A restriction map of the AD169 HCMV genome is disclosed in U.S. Pat. No. 4,762,780) Variation in the DNA content among other isolated strains of HCMV has also been detected. Huang, *Yale J. Biol. and Med.* 49:29–43(1976). Cleavage patterns of restriction enzyme digests of HCMV DNA of various strains has been analyzed. Kilpatrick, *J. Virol.* 18:1095–1105 (1976); LaFemina, "Structural Organization of the DNA Molecules from Human Cytomegalovirus" in *Animal Virus Genetics*, eds. Field, B N and R. Jaenish, Academic Press, N.Y. (1980); Chandler, *J. Gen. Virol.* 67:2179–92(1986); Zaia, *J. Clin. Microbiol.* 28:2602–07(1990). However, although the gross structural organization of the HCMV genome has been determined and strain-to-strain restriction site polymorphism mapped for many of the strains, strain-to-strain differences in the DNA sequences of the HCMV genome have not been determined. Only partial sequences have been deduced and compared, For example, the DNA and amino acid sequences of the envelope glycoprotein B [gpUL55(gB)] of both Towne and AD169 strains have been deduced, see Spaete, *Virology* 167:207–25(1988), and compared with various clinical isolates, see Chou, *J. Infect. Dis.* 163:1229–34(1991), to identify conserved regions and regions of variability. In addition, DNA sequence analysis of certain regions of the gp58/116 gene [gpUL55(gB)], the IMP gene and the IE-1/2 enhancer/promoter has been accomplished. Lehner, *J. Clin. Microbiol.* 29:2494–2502(1991).

Whereas the complete DNA sequence of the AD169 strain of HCMV has been deduced, (EMBL Accession No. X17403), the complete DNA sequence of the Towne strain has not to our knowledge been deduced. However, it has been speculated that AD169 and another laboratory strain, Davis, are missing two to four kilobase pairs (kb) of DNA sequence compared to the Towne strain at the extreme internal portions of both L repeats. LeFemina, supra, at 52–53.

The public health impact of HCMV infections has not been well controlled by current treatment strategies or available antiviral chemotherapies. Preventative vaccine strategies are likely to prove efficacious because of the observations that seropositive renal allograft recipients are protected from severe HCMV disease and maternal immunity protects the fetus from disease after intrauterine infection. Marshall and Plotkin, "Cytomegalovirus Vaccines" in The Human Herpesviruses, eds Roizman, B., R. J. Whitley and C. Lopez, Raven Press, New York, 1993, pps 381–95. However, an additional obstacle to the development of a vaccine for HCMV is the lack of an animal model system that can be used to test the safety and efficacy of vaccine candidates.

There remains a need in the art for efficacious vaccines for the prophylactic treatment of HCMV in humans.

SUMMARY OF THE INVENTION

In one aspect, the invention provides novel HCMV DNA sequences not heretofore recognized or known in the art. These novel HCMV sequences were isolated from the Toledo and Towne strains of HCMV and comprise DNA that is not shared by reference strain AD169 of HCMV. Accordingly, in this aspect the invention provides novel, isolated, Toledo strain HCMV DNA sequences. As used herein, "isolated" means substantially free from other viral DNA sequences with which the subject DNA is typically found in its native, i.e., endogenous, state. These novel Toledo HCMV DNA sequences are characterized by comprising the same or substantially the same nucleotide sequence as in FIG. 1 (SEQ ID NO:6), or active fragments thereof. The DNA sequences may include 5' and 3' non-coding sequences flanking the coding sequence. The DNA sequences may be in inverted orientation with respect to the orientation shown in FIG. 1. Segments or fragments of the DNA sequence shown in FIG. 1 (SEQ ID NO:6) may be rearranged or inverted internally. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 1. FIG. 1 (SEQ ID NO:6) illustrates the DNA sequence of the novel Toledo strain HCMV. Twenty one open reading frames (ORFs) were identified in this sequence. The putative amino acid sequences of these novel Toledo strain HCMV ORFs are enumerated in sequence identification numbers 7 through 27, pages 58 through 78, infra. In FIG. 1, the beginning and ending of the 21 ORFs are identified by the arrows and the designations "UL133", "UL134", etc. (see infra.). In rearranged sequences of the invention, novel open reading frames may be created or destroyed.

In another aspect, the invention provides additional novel HCMV DNA sequences not heretofore recognized or known in the art. These additional sequences were isolated from the Towne strain of HCMV and comprise DNA that is not shared by the AD169 strain or by the Toledo strain of HCMV. Accordingly, in this aspect the invention provides novel Towne strain HCMV sequences. These novel Towne HCMV DNA sequences are characterized by as comprising the same or substantially the same nucleotide sequence as m FIG. 2 (SEQ ID NO:1), or active fragments thereof. The DNA sequence may include 5' and 3' non-coding sequences flanking the coding sequence. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 2 (SEQ ID NO:1). FIG. 2 (SEQ ID NO:1) illustrates the DNA sequence of the novel Towne strain HCMV. Four ORFs were identified in this sequence. The putative amino acid sequences of these novel ORFs are enumerated in sequence identification numbers 2 through 5, pages 42 through 45 infra. In FIG. 2, the beginning and ending of the 4 ORFs are identified by the arrows and the designations UL147, UL152, UL153 and UL154.

It is understood that the DNA sequences of this invention may exclude some or all of the signal and/or flanking sequences. In addition, the DNA sequences of the present invention may also comprise DNA capable of hybridizing under stringent conditions, or which would be capable of hybridizing under such conditions but for the degeneracy of the genetic code, to an isolated DNA sequence of FIG. 1 or FIG. 2. (SEQ ID NOS:6 and 1). As used herein, "stringent conditions" means conditions of high stringency, for example 6× SSC, 0.2% polyvinylpyrrolidone, 0.2% Ficoll, 0.2% bovine serum albumin, 0.1% sodium dodecyl sulfate, 100 $\mu$g/ml salmon sperm DNA and 15% formamide at 68 degrees C. (See Materials and Methods, Part C, infra.)

Accordingly, the DNA sequences of this invention may contain modifications in the non-coding sequences, signal sequences or coding sequences, based on allelic variation, species or clinical isolate variation or deliberate modification. Using the sequences of FIG. 1 and 2 (SEQ ID NOS:6 and 1), it is within the skill in the art to obtain other modified DNA sequences: the sequences can be truncated at their 3'-tetmini and/or their 5'-termini, the gene can be manipulated by varying individual nucleotides, while retaining the original amino acid(s), or varying the nucleotides, so as to modify amino acid(s). Nucleotides can be substituted, inserted or deleted by known techniques, including for example, in vitro mutagenesis and primer repair. In addition, short, highly degenerate oligonucleotides derived from regions of imperfect amino acid conservation can be used to identify new members of related viral and cellular families. RNA molecules, transcribed from a DNA of the invention as described above, are an additional aspect of the invention.

In another aspect, the invention provides novel HCMV proteins, which are substantially free fromn other HCMV proteins with which they are typically found in their native state. These novel HCMV proteins comprise the open reading frames (ORFs) UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO:17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26) identified in the novel Toledo strain DNA sequence and UL147 (SEQ ID NO:2), UL152 (SEQ ID NO:3), UL153 (SEQ ID NO:4) and/or UL154 (SEQ ID NO:5) identified in the novel Towne strain DNA sequence. Two additional HCMV ORFs were identified in the novel Toledo stain DNA sequence, UL130 and UL132 (SEQ ID NOS:23 and 27). These two sequences are also present in AD169 (see FIG. 5). The proteins may be produced by recombinant genetic engineering techniques. They may additionally be purified from cellular sources infected with HCMV. They may also be synthesized by chemical techniques. One skilled in the art could apply a combination of the above-identified methodologies to synthesize the protein. Additionally, analogs of the HCMV proteins of the invention are provided and include truncated polypeptides, e.g., mutants in which there are variations in the amino acid sequence that retain activity, as defmed below, and preferably have a homology of at least 80%, more preferably 90%; and most preferably 95%, with the corresponding regions of the HCMV Towne or Toledo amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27). Examples include polypeptides with minor amino acid variations from the native amino acid sequences of HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27); in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on activity or functionality.

Using the Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27) it is within the skill in the art to obtain other polypeptides or other DNA sequences encoding the HCMV Toledo or Towne protein from clinical isolates of HCMV. For example, the structural gene can be manipulated by varying individual nucleotides, while retaining the correct amino acid(s), or varying the nucleotides, so as to modify the amino acids, without loss of activity. Nucleotides can be substituted, inserted, or deleted by known techniques, including, for example, in vitro mutagenesis and primer repair. The structural gene can be truncated at its 3'-terminus and/or its 5'-terminus while retaining its activity. It also may be desirable to remove the region encoding the signal sequence, and/or to replace it with a heterologous sequence. It may also be desirable to ligate a portion of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27), particularly that which includes the amino terminal domain to a heterologous coding sequence, and thus to create a fusion peptide of HCMV Toledo or Towne.

In designing such modifications, it is expected that changes to nonconserved regions of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27) will have relatively smaller effects on activity, whereas changes in the conserved regions, and particularly in or near the amino terminal domain are expected to produce larger effects. Amino acid residues that are conserved between the HCMV Toledo or Towne amino acid sequences (SEQ ID NOS:2, 3, 4, 5, 7, 8, 9, 10, 11, 12, 14, 15, 17, 18, 19, 21, 22, 23, 24, 25, 26, and 27) and at least two other sequences, for example, from HCMV clinical isolates are not expected to be candidates for substitution. A residue which shows conservative variations among the HCMV sequences and at least two of the other sequences is expected to be capable of similar conservative substitution of the HCMV sequences. Similarly, a residue which varies nonconservatively among the HCMV sequences and at least three of the other sequences is expected to be capable of either conservative or nonconservative substitution. When designing substitutions to the HCMV sequences, replacement by an amino acid which is found in the comparable aligned position of one of the other sequences is especially preferred.

Additionally provided by this invention is a recombinant DNA vector comprising vector DNA and a DNA sequence encoding an HCMV Toledo polypeptide or HCMV Towne polypeptide. The vector provides the HCMV Toledo or Towne DNA in operative association with a regulatory sequence capable of directing the replication and expression of an HCMV Toledo or Towne protein in a selected host cell. Host cells transformed with such vectors for use in expressing recombinant HCMV Toledo or Towne proteins are also provided by this invention. Also provided is a novel process for producing recombinant HCMV Toledo or Towne proteins or active fragments thereof. In this process, a host cell line transformed with a vector as described above containing a DNA sequence (SEQ ID NOS:1 and 6) encoding expression of an HCMV Toledo or Towne protein in operative association with a suitable regulatory sequence capable of directing replication and controlling expression of an HCMV Toledo or Towne protein is cultured under appropriate conditions permitting expression of the recombinant DNA. The expressed protein is then harvested from the host cell or culture medium using suitable conventional means. This novel process may employ various known cells as host cell lines for expression of the protein. Currently preferred cells are mammalian cell lines, yeast, insect and bacterial cells. Especially preferred are mammalian cell lines.

The practice of the invention will employ, unless otherwise indicated, conventional techniques of molecular biology, microbiology, recombinant DNA manipulation and production, and immunology, which are within the skill of the art. Such techniques are explained fully in the literature. See, e.g., Sambrook, *Molecular Cloning: A Laboratory Manual*, Second Edition (1989); *DNA Cloning*, Volumes I and II (D. N. Glover, Ed. 1985); *Oligonucleotide Synthesis* (M. J. Gait, Ed. 1984); *Nucleic Acid Hybridization* (B. D. Hames and S. J. Higgins, Eds. 1984); *Transcription and Translation* (B. D. Hames and S. J. Higgins, Eds. 1984); *Animal Cell Culture* (R. I. Freshney, Ed. 1986); *Immobilized Cells and Enzymes* (IRL Press, 1986); B. Perbal, *A Practical Guide to Molecular Cloning* (1984); the series, *Methods in Enzymology* (Academic Press, Inc.); *Gene Transfer Vectors for Mammalian Cells* (J. H. Miller and M. P. Calos, Eds. 1987, Cold Spring Harbor Laboratory), *Methods in Enzymology*, Volumes 154 and 155 (Wu and Grossman, and Wu, Eds., respectively), (Mayer and Walker, Eds.) (1987); *Immunochemical Methods in Cell and Molecular Biology* (Academic Press, London), Scopes, (1987); *Protein Purification: Principles and Practice*, Second Edition (Springer-Verlag, N.Y.); and *Handbook of Experimental Immunology*, Volumes I–IV (D. M. Weir and C. C. Blackwell, Eds 1986). All patents, patent applications and publications mentioned herein, both supra and infra, are hereby incorporated by reference.

Additionally provided by this invention are compositions for detecting HCMV infections in humans. These compositions comprise probes having at least one single-stranded fragment of at least 10 bases in length, more preferably 15 bases in length, of the novel Toledo sequence, and fragments hybridizing to these single-stranded fragments under stringent hybridization conditions and non-cross-hybridizing with human DNA. Additionally, these compositions comprise at least one single-stranded fragment of at least 10 bases in length, more preferably 15 bases in length, of the novel Towne sequence, and fragments hybridizing to these single-stranded fragments under stringent hybridizing with human DNA. Such probe compositions may additionally comprise a label, attached to the fragment, to provide a detectable signal, as is taught in U.S. Pat. No. 4,762,780.

Further provided by this invention are methods for detecting an HCMV infection in a human host. Such methods comprise combining under predetermined stringency conditions a clinical sample suspected of containing HCMV DNA with at least one single-stranded DNA fragment of the novel Toledo or Towne strain of HCMV having at least 10 bases, more preferably 15 bases, and being non-cross-hybridizing with human DNA, and detecting duplex formation between the single-stranded Toledo or Towne strain HCMV fragments and the sample DNA. Alternatively, PCR may be used to increase the viral nucleic acid copy number by amplification to facilitate the identification of HCMV in infected individuals. In such case, the single-stranded Toledo or Towne strain DNA sequence fragments of the present invention can be used to construct PCR primers for PCR-based amplification systems for the diagnosis of HCMV. Such systems are well known in the art. See for example, U.S. Pat. No. 5,008,182 (detection of AIDS associated virus by PCR) and Hedrum, PCR Methods and Applications 2:167–71(1992) (detection of Chlamydia trachomatis by PCR and immunomagnetic recovery).

The DNA sequences of this invention may also be used to prepare immunizing compositions. The novel Toledo DNA sequences are recombined into the Towne strain or AD169 strain of HCMV and these recombinant viruses tested for growth properties in endothelial cells or in human tissues transplanted into SCID mice or tested in the rat eye model. Mocarski, *Proc. Nat. Acad. Sci* 90:104–08(1993). Such recombinants will show increased immunogenicity over that shown by the Towne-125 strain currently in use in humans, without exhibiting the full virulence shown by the Toledo-1 strain. Therefore, a further aspect of the invention is immunizing compositions comprising either the Towne strain or the AD169 reference strain of HCMV to which the novel Toledo DNA sequence, or analogs or fragments thereof, have been added, resulting in increased immunogenicity of the recombinant virus. The invention also includes a method for the prophylactic treatment of HCMV in humans comprising administering to a human patient an immunogenically inducing effective amount of an immunizing composition of the invention in a suitable pharmaceutical carrier. Still another aspect of the invention is a method of stimulating an immune response against CMV by administering to a patient an immunogenically inducing effective amount of an immunizing composition of the invention in a suitable pharmaceutical vehicle.

Other aspects and advantages of this invention are described in the following detailed description.

BRIEF DESCRIPTION OF THE DRAWINGS

FIGS. 1A–1T illustrates the novel Toledo DNA sequence of the invention isolated from the Toledo strain of HCMV. The arrows indicate the beginnings and ends of nucleotide sequences encoding the 21 putative amino acid sequences identified.

FIGS. 2A–2E illustrates the novel Towne DNA sequence of the invention isolated from the Towne strain of HCMV. The arrows indicate the beginnings and ends of the nucleotide sequences encoding the 4 putative amino acid sequences identified.

FIG. 3 is a schematic representation of a Southern blot of restriction enzyme digested Towne and Toledo HCMV strain DNA as detailed in Example 1. The arrow indicates a 5 kbp (kilobase pair) band of Toledo DNA on the BamHI digest that is lacking in the Towne DNA, signifying the presence of additional Toledo DNA sequence.

FIG. 4 illustrates a composite autoradiograph of the restriction enzyme digested DNA from AD169, Towne, Toledo and five clinical isolates of HCMV as described in Example 3.

FIG. 5 is a schematic presentation of the novel open reading frames identified in the novel Toledo and Towne DNA sequences.

FIG. 6 is a schematic illustration of the relative positions of novel sequences identified in Toledo genomic DNA, Towne genomic DNA in a comparison with AD169 strain genomic DNA.

DETAILED DESCRIPTION

A. Introduction

The invention provides two novel HCMV DNA sequences, termed Toledo sequence and Towne sequence, not heretofore recognized or known in the art. The invention also provides immunization compositions and methods using the novel HCMV DNA sequences of the invention and also provides other diagnostic and therapeutic uses for the sequences and their protein products. The new DNA sequences were originally found in the Toledo and Towne strains of HCMV. Details of the sequences and structural characteristics are provided in the Examples below.

Most desirably, HCMV immunogenic compositions are provided that comprise reference strain AD169 or Towne to which the novel Toledo DNA sequences, or analogs or fragments thereof, have been added in order to increase the immunogenicity of the overly-attenuated strain. Thus, one aspect of this invention includes isolated DNA and corresponding RNA sequences as disclosed in FIGS. 1 and 2 (SEQ ID NOS:6 and 1). As used herein, "isolated" means substantially free from other nucleotide or polypeptide sequences with which the subject nucleotide sequence or polypeptide sequence is typically found in its native, i.e., endogenous, state. In another aspect, the invention comprises isolated HCMV Towne or Toledo protein encoded by the respective HCMV Towne or Toledo DNA sequences (SEQ ID NOS:2, 3, 4, 5, 7, 8, 9, 10, 11, 12, 13, 14, 15, 16, 17, 18, 19, 20, 21, 22, 23, 24, 25, 26, and 27).

Another aspect of this invention includes diagnostic assays for the detection of HCMV strain variants. In brief, such diagnostic assays include the use of DNA sequence fragments of the invention as primers for amplifying HCMV related nucleic acids in a polymerase chain reaction (PCR) or by direct detection by hybridization. The diagnostic assays of the invention may also include the use of specific antibodies against the novel ORFs encoded by the Toledo or Towne DNA sequences disclosed here. Yet another aspect of the invention is the use of the novel DNA sequences modified with a unique restriction site, to act as vaccine markers.

It is anticipated that the invention will enable the production of vaccines that offer advantages over the current HCMV vaccine, which is overly attenuated and therefore not consistently effective in eliciting an immune response. More specifically, the introduction or insertion of the novel Toledo strain sequences of the present invention into the Towne strain or into the AD169 strain will result in the introduction of specific DNA sequences in the HCMV Towne genome that are not possible using the cell passage vaccines. Importantly for vaccine production, this enables precise measurement of the degree of attenuation introduced by different fragments of the DNA sequences of the invention, thereby enabling the controlled modification in the attenuation of the Towne strain that is needed in the art to correct the Towne's strain's overly attenuated characteristic and improve its function as an immunogenic composition.

B. Recombinant AD169 or Towne HCMV

Recombinant AD169 or Towne DNA is derived by co-transfecting a plasmid containing the novel Toledo sequence, or analogs or fragments thereof, and a selectable marker such as gpt or β-galactosidase in primary fibroblast cells, or other cell lines known to be permissive for growth of CMV. Recombinant viruses are selected by growth in media containing mycophenolic acid or identified by blue plaque phenotypes after applying a chromogenic substrate such as X-gal. Recombinant viruses are plaque purified and characterized by restriction enzyme analysis and Southern blotting procedures. The novel HCMV Toledo sequence, or analogs or fragments thereof, may be used unmodified with respect to the endogenous promoter and transcription termination signals. Alternatively, the HCMV Toledo strain DNA coding region can be placed under transcriptional control of a promoter such as the CMV (cytomegalovirus) major immediate early promoter, the SV40 early promoter or some other viral or cellular promoter that generates adequate levels of expression, as discussed herein.

Modified Towne or AD169 strain HCMV is grown in tissue culture cells. For experiments with mammals, not including humans, cells such as human foreskin fibroblasts (HF) or MRC-5 cells are used to propagate the virus. The virus is harvested from cultures of these cells and the isolated recombinant virus is then be further studied for its ability to elicit an immune response and provide protection against HCMV infection.

For use in humans, the recombinant virus is produced from an FDA approved cell line in large scale amounts. Such cells include MRC-5 or WI-38 cells (both are primary human diploid fibroblasts). The recombinant virus is generated in the production cell line by transfection of viral DNA or capsids prepared from recombinant virus isolated from another cell line. The method of transfection should prevent the contamination of FDA approved cells with adventitious agents or contaminants from a non-qualified cell line. A HCMV virus produced from the above cell lines will be used to infect progressively larger flasks of tissue culture cells. Infected cells will be used as subsequent inoculums. Viable infected tissue culture cells are removed from the tissue culture vessels using trypsin and added to a 1 to 100 fold (or more) excess of uninfected cells to accomplish progressively larger inoculations. Once an optimal yield is obtained the virus will be harvested from the tissue culture cells. This process can be repeated until a large scale production is achieved. Infected cells will be removed from the tissue culture vessel and disrupted using for example, sonication, dounce homogenization or some combination of the above. The viruses are then isolated from cellular material using centrifugation techniques known in the art. Once the virus is isolated a stabilizing agent is added, such as a carbohydrate or carbohydrate derivative and the virus is then aliquoted and lyophilized.

C. Immunogenic Compositions

Immunogenic compositions can be administered to subjects to prevent HCMV infections. The immnunogenic compositions prevent HCMV infections by stimulating the immune system with an attenuated virus incapable of fully manifesting the disease. A major advantage of the HCMV immunogenic compositions provided herein is that its increased degree of immunogenicity will result in move effective prevention of an HCMV infection in the population.

The Towne strain of HCMV will preferably serve as the parent strain due to its proven inability to reactivate. To make HCMV immunogenic compositions, full, truncated and/or modified novel Toledo DNA sequences are introduced into a HCMV AD169 or Towne strain virus as discussed herein. The effectiveness of the immunogenic composition in preventing HCMV infections will be measured in humans. Humans will be first inoculated with PFU's ranging from 100–20,000 PFU of mutant virus per inoculation, PFUs are measured as discussed herein. After the first inoculation, a second booster injection of similar or increased dosage usually may be given. Subjects will be exposed to wild-type HCMV after the first or second inoculation and the occurrence of CMV infections observed. Potential side effects of the vaccine will be monitored in volunteer adults previously exposed to CMV, before inoculating subjects that have not ever developed CMV infections. Attenuated virus is used without an adjuvant and with a physiologically suitable carrier.

As is known in the art and discussed herein, the novel DNA is inserted into the Towne or AD169 viral genome using, for example, homologous recombination techniques. The insertion is generally made into a gene which is non-essential in nature. Plasmid shuttle vectors that greatly facilitate the construction of recombinant viruses have been described. See, for example, Spaete and Mocarski, *Proc. Nat. Acad. Sci* 84:7213–17(1987). Expression of the polypeptide encoded by the novel Toledo DNA then occurs in cells or individuals which are immunized with the live recombinant virus.

Alternatively, the purified novel HCMV proteins may be employed in therapeutic and/or subunit immunogenic compositions for preventing and treating HCMV related conditions. Such pharmaceutical compositions comprise an immunogenically-inducing effective amount of one or more of the proteins of the present invention in admixture with a pharmaceutically acceptable carrier, for example an adjuvant/antigen presentation system such as alum. Other adjuvant/antigen presentation systems, for instance, MF59 (Chiron Corp.), QS-21 (Cambridge Biotech Corp.), 3-DMPL (3-Deacyl-Monophosphoryl Lipid A) (RibiImmunoChem Research, Inc.), clinical grade incomplete Freund's adjuvant (IFA), fusogenic liposomes, water soluble polymers or Iscoms (Iminune stimulating complexes) may also be used. Other exemplary pharmaceutically acceptable carriers or solutions are aluminum hydroxide, saline and phosphate buffered saline. The composition can be systemically administered, preferably subcutaneously or intramuscularly, in the form of an acceptable subcutaneous or intramuscular solution. Also inoculation can be effected by surface scarification or by inoculation of a body cavity. The preparation of such solutions, having due regard to pH, isotonicity, stability and the like is within the skill in the art. The dosage regimen will be determined by the attending physician considering various factors known to modify the action of drugs such as for example, physical condition, body weight, sex, diet, severity of the condition, time of administration and other clinical factors. Exemplary dosage ranges comprise between about 1 $\mu$g to about 1000 $\mu$g of protein.

In practicing the method of treatment of this invention, an immunologically-inducing effective amount of protein is administered to a human patient in need of therapeutic or prophylactic treatment. An immunologically inducing effective amount of a composition of this invention is contemplated to be in the range of about 1 microgram to about 1 milligram per dose administered. The number of doses administered may vary, depending on the above mentioned factors.

D. Diagnostic Assays and Use as a Vaccine Marker

The novel Toledo and Towne DNA sequences of the present invention can be used in diagnostic assays to detect HCMV in a sample, to detect Toledo and Towne—like sequences and to detect strain differences in clinical isolates of HCMV using either chemically synthesized or recombinant Toledo or Towne DNA fragments. Additionally, the novel sequences can be used as a vaccine marker to differentiate between an individual or sample infected with or containing wild type HCMV and an individual or sample infected with or containing a HCMV vaccine, i.e., a live attenuated HCMV vaccine currently in use such as the Towne vaccine. In yet another embodiment, fragments of the DNA sequences can also be linked to secondary nucleic acids with sequences that either bind a solid support or other detection probes for use in diagnostic assays. In one aspect of the invention, fragments of the novel Toledo or Towne DNA sequences (SEQ ID NOS:1 and 3) comprising at least between 10 and 20 nucleotides can be used as primers to amplify nucleic acids using polymerase chain reaction (PCR) methods well known in the art and as probes in nucleic acid hybridization assays to detect target genetic material such as HCMV DNA in clinical specimens (with or without PCR). See for example, U.S. Pat. Nos. 4,683,202; 4,683,195; 5,091,310; 5,008,182 and 5,168,039. In an exemplary assay, a conserved region of the novel DNA sequence among virus variants is selected as the sequence to be amplified and detected in the diagnostic assay. Oligonucleotide primers at least substantially complementary to (but preferably identical with) the sequence to be amplified are constructed and a sample suspected of containing a HCMV nucleic acid sequence to be detected is treated with primers for each strand of HCMV nucleic acid sequence to be detected, four different deoxynucleotide triphosphates and a polymerization agent under appropriate hybridization conditions such that an extension product of each primer is synthesized that is complementary to the HCMV nucleic acid sequences suspected in the sample, which extension products synthesized from one primer, when separated from its complement can serve as a template for synthesis of the extension product of the other primer in a polymerase chain reaction. After amplification, the product of the PCR can be detected by the addition of a labeled probe, likewise constructed from the novel DNA sequence, capable of hybridizing with the amplified sequence as is well known in the art. See, e.g. U.S. Pat. No. 5,008,182.

In another embodiment the probes or primers can be used in a vaccine marker assay to detect a vaccine or wild type infection. Alternatively, introduction of a restriction site into the novel DNA sequence will provide a vaccine marker that can be used with PCR fragments to detect such differences in a restriction digest. Such procedures and techniques for detecting sequence variants, such as, point mutations with the expected location or configuration of the mutation, are known in the art and have been applied in the detection of sickle cell anemia, hemoglobin C disease, diabetes and other diseases and conditions as disclosed in U.S. Pat. No. 5,137,806. These methods are readily applied by one skilled in the art to detect and differentiate between wild type and vaccine infections in HCMV.

In another embodiment the novel Toledo or Towne DNA sequences can be used in their entirety or as fragments to detect the presence of DNA sequences, related sequences, or transcription products in cells, tissues, samples and the like using hybridization probe techniques known in the art or in conjunction with one of the methods discussed herein. When used as a hybridization probe, fragments of the novel DNA sequences of the invention are preferably 50–200 nucleotides long, more preferably 100–300 nucleotides long and most preferably greater than 300 nucleotides long.

E. Vectors and Chimeric Virus Production

The novel DNA sequences of the invention can be expressed in different vectors using different techniques known in the art resulting in the generation of chimeric virus. Useful and known techniques include marker transfer or homologous recombination, direct in vitro ligation, defective vector technology and amplicon generation (see, e.g., Frenkel, N. et al., *Gene Transfer and Cancer*, edited by M. L. Pearson and N. L. Sternberg (1984), Kwong, A. D. and Frenkel, *Virology* 142,421–425(1985); U.S. patent (Ser. No. 07/923,015 by Roizman). Vectors used in such techniques include cosmids, plasmids, and infective or defective viruses. Such vectors are known in the art. (A cosmid as used herein is a plasmid containing a lambda bacteriophage cos site. The cos site is the cis signal for packaging lambda DNA. Therefore, a cosmid, unlike a plasmid, can be packaged with high efficiency into a lambda head in vitro. This technique allows cloning of very large (30–45 kbp) fragments of DNA.) The vectors can be either single stranded or double stranded and made of either DNA or RNA.

Generally, the DNA sequence is inserted into the vector alone or linked to other HCMV genomic DNA. In direct in vitro ligation applications, the isolated sequence alone is used. In homologous recombination and marker transfer flanking nucleic acid sequences are required to effect transfer of the sequence into a HCMV viral genome. For use in viral complementation using cosmids and other vectors discussed herein the sequence (or a fragment thereof) in a vector is preferably operatively linked to at least 1 kb of HCMV genomic nucleic acid and more preferably at least 5 kb of HCMV nucleic acid. The HCMV genomic nucleic acid can be on one side or both sides of the open reading frame. If only a specific region of the open reading frame is to be used to generate a mutant virus, an open reading frame or fragment thereof is inserted into a vector.

F. Novel Toledo and Towne Protein

Another aspect of the invention includes the isolated proteins encoded by the Toledo or Towne DNA sequence as taught herein. The proteins can be used to study and modify the life cycle of HCMV because they may encode surface glycoproteins that may be immunogenic and responsible for tissue tropism or influence the immune response in an infected individual. Such proteins could therefore be used in the production of a subunit vaccine against CMV. The construction of such CMV subunits vaccine candidates is known in the art. See, for example, Spaete, *Virology* 167:207–25(1988).

Twenty-one novel Toledo and four novel Towne proteins have been identified by ORF analysis. The novel Toledo proteins include UL130 (SEQ ID NO:23), UL132 (SEQ ID NO:27), UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO:17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26). UL130 is encoded by nucleotides 13109 through 13753, as shown in FIG. 1. UL132 is encoded by nucleotides 11673 through 12485, as shown in FIG. 1. UL133 is encoded by nucleotides 51 through 824, as shown in FIG. 1. UL134 is encoded by nucleotides 541 through 1068, as shown in FIG. 1. UL135 is encoded by nucleotides 941 through 1927, as shown in FIG. 1. UL136 is encoded by nucleotides 2018 through 2740, as shown in FIG. 1. UL137 is encoded by nucleotides 2599 through 2890, as shown in FIG. 1. UL138 is encoded by nucleotides 2823 through 3332, as shown in FIG. 1. UL139 is encoded by nucleotides 3895 through 4302, as shown in FIG. 1. UL140 is encoded by nucleotides 4484 through 4828, as shown in FIG. 1. UL141 is encoded by nucleotides 5098 through 6375, as shown in FIG. 1. UL142 is encoded by nucleotides 6448 through 7368, as shown in FIG. 1. UL143 is encoded by nucleotides 7353 through 7631, as shown in FIG. 1. UL144 is encoded by nucleotides 8008 through 8538, as shown in FIG. 1. UL145 is encoded by nucleotides 8867 through 9169, as shown in FIG. 1. UL146 is encoded by nucleotides 9450 through 9803, as shown in FIG. 1. UL147 is encoded by nucleotides 9868 through 10347, as shown in FIG. 1. UL148 is encoded by nucleotides 10646 through 11596, as shown in FIG. 1. UL149 is encoded by nucleotides 15756 through 16124, as shown in FIG. 1. UL150 is encoded by nucleotides 15874 through 17802, as shown in FIG. 1. UL151 is encoded by nucleotides 17289 through 18299, as shown in FIG. 1.

The novel Towne proteins include UL147, UL152, UL153 and UL154 (SEQ ID NOS:2, 3, 4 and 5, respectively). UL147 is encoded by nucleotides 841 through 1321, as shown in FIG. 2. UL152 is encoded by nucleotides 1365 through 1721, as shown in FIG. 2. UL153 is encoded by nucleotides 2501 through 3337, as shown in FIG. 2. UL154 is encoded by nucleotides 3512 through 4711, as shown in FIG. 2.

"Toledo and/or Towne protein or proteins" as used herein refer to the above sequences, also enumerated in the sequence listing. "Toledo and/or Towne protein or proteins"

also refers to an homologous protein from any strain or clinical isolate of HCMV, including HCMV proteins that are at least 90% homologous to the Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27). The Toledo or Towne protein can be modified to affect HCMV life cycle by deletion, insertion and substitution into the DNA sequence, as discussed herein, or by chemical synthesis of different amino acid sequence or by chemical modification. Truncated proteins can be formed by deletion of a portion of the DNA sequence or the introduction of termination signal(s) into the DNA sequence. Preferred deletions to the protein correspond to deleted amino acid sequence or sequences that contain at least one amino acid selected from the group consisting of Glu, Asp, Arg, Lys, Cys and Pro. More preferably at the deleted amino acid sequence or sequences contain at least two amino acids selected from the group consisting of Glu, Asp, Arg, Lys, Cys and Pro. More preferably the deleted amino acid sequence or sequences contain at least two prolines.

Other mutations of the protein useful in modifying HCMV life cycle include, but are not limited to, modification of cAMP phosphorylation (Arg/Lys-Arg/Lys-X-X-Asp/Glu) and/or, myristylization sites (Glycine-X1-X2-X3-Ser/Thr-X-X-Asp/Glu; where X1 is not Glu, Asp, Arg, Lys, His Pro, Phe, Tyr, Trp, where X2 is any amino acid and where X3 is not Pro), or modification of the PKC phosphorylation sites (Ser/Thr-X-Arg/Lys) and/or N-linked glycosylation sites (Asn-X-Ser/Thr; where X is not Pro).

The Toledo or Towne DNA sequences, analogs or fragments thereof can be expressed in a mammalian, insect, or microorganism host. The polynucleotide is inserted into a suitable expression vector compatible with the type of host cell employed and is operably linked to the control elements within that vector. Vector construction employs techniques which are known in the art. Site-specific DNA cleavage involved in such construction is performed by treating with suitable restriction enzymes under conditions which generally are specified by the manufacturer of these commercially available enzymes. A suitable expression vector is one that is compatible with the desired function (e.g., transient expression, long term expression, integration, replication, amplification) and in which the control elements are compatible with the host cell.

Mammalian Cell Expression

Vectors suitable for replication in mammalian cells are known in the art, and can include viral replicons, or sequences that ensure integration of the sequence encoding the Toledo or Towne DNA into the host genome. Exemplary vectors include those derived from SV40, retroviruses, bovine papilloma virus, vaccinia virus, other herpesviruses and adenovirus.

Such suitable mammalian expression vectors contain a promoter to mediate transcription of foreign DNA sequences and, optionally, an enhancer. Suitable promoters are known in the art and include viral promoters such as those from SV40, cytomegalovirus (CMV), Rous sarcoma virus (RSV), adenovirus (ADV), and bovine papilloma virus (BPV).

The optional presence of an enhancer, combined with the promoter described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when placed upstream or downstream from the transcription initiation site, in either normal or flipped orientation, or at a distance of more than 1000 nucleotides from the promoter. See Maniatis, *Science* 236:1237(1987), Alberts, *Molecular Biology of the Cell*, 2nd Ed. (1989). Enhancers derived from viruses may be particularly useful, because they typically have a broader host range. Examples include the SV40 early gene enhancer (see Dijkema, *EMBO J*. 4:761(1985)) and the enhancer/promoters derived from the long terminal repeat (LTR) of the RSV (see Gorman, *Proc. Natl. Acad. Sci*. 79:6777(1982b)) and from human cytomegalovirus (see Boshart, *Cell* 41:521(1985)). Additionally, some enhancers are regulatable and become active only in the presence of an inducer, such as a hormone or metal ion (see Sassone-Corsi and Borelli, *Trends Genet*. 2:215(1986)); Maniatis, *Science* 236:1237(1987)). In addition, the expression vector can and will typically also include a termination sequence and poly(A) addition sequences which are operably linked to the Toledo or Towne coding sequence.

Sequences that cause amplification of the gene may also be desirably included in the expression vector or in another vector that is co-translated with the expression vector containing a Towne or Toledo DNA sequence, as are sequences which encode selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes a novel Toledo or Towne protein or polypeptide of this invention can be used for transformation of a suitable mammalian host cell. Transformation can be by any known method for introducing polynucleotide into a host cell, including, for example packaging the polynucleotide in a virus and transducing a host cell with the virus. The transformation procedure used depends upon the host to be transformed. Methods for introduction of heterologous polynucleotide into marmalian cells are known in the art and include dextran-mediated transfection, calcium phosphate precipitation, polybrene mediated transfection, protoplast fuision, electroporation, encapsulation of the polynucleotide (s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLA cells, baby hamster kidney (BHK) cells, monkey kidney cells (COS), human hepatocellular carcinoma cells (e.g., Hep G2), and a number of other cell lines.

Insect Cell Expression

The components of an insect cell expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media. Exemplary transfer vectors for introducing foreign genes into insect cells include pAc373 and pVL985. See Luckow and Summers, *Virology* 17:31(1989).

The plasmid can also contains the polyhedron polyadenylation signal and a procaryotic ampicillin-resistance (amp) gene and origin of replication for selection and propagation in *E. coli*. See Miller, *Ann, Rev. Microbiol*. 42:177(1988).

Baculovirus transfer vectors usually contain a baculovirus promoter, i.e., a DNA sequence capable of binding a baculovirus RNA polymerase and initiating the downstream (5' to 3') transcription of a coding sequence (e.g., structural gene) into mRNA. The promoter will have a transcription initiation region which is usually placed proximal to the 5' end of the coding sequence and typically includes an RNA polymerase binding site and a transcription initiation site. A baculovirus transfer vector can also have an enhancer, which, if present, is usually distal to the structural gene. Expression can be either regulated or constitutive.

Yeast And Bacteria Expression

A yeast expression system can typically include one or more of the following: a promoter sequence, fusion partner sequence, leader sequence, transcription termination sequence. A yeast promoter, capable of binding yeast RNA polymerase and initiating the downstream (3') transcription of a coding sequence (e.g. structural gene) into mRNA, will have a transcription initiation region usually placed proximal to the 5' end of the coding sequence. This transcription initiation region typically includes an RNA polymerase binding site (a "TATA Box") and a transcription initiation site. The yeast promoter can also have an upstream activator sequence, usually distal to the structural gene. The activator sequence permits inducible expression of the desired heterologous DNA sequence. Constitutive expression occurs in the absence of an activator sequence. Regulated expression can be either positive or negative, thereby either enhancing or reducing transcription.

Particularly useful yeast promoters include alcohol dehydrogenase (ADH) (EP Patent Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK)(EP Patent Pub. No. 329 203). The yeast PHO5 gene, encoding acid phosphatase, also provides useful promoter sequences. See Myanohara, *Proc. Natl. Acad. Sci. USA* 80:1(1983).

A Toledo or Towne DNA sequence, analog or an active fragment thereof can be expressed intracellularly in yeast. A promoter sequence can be directly linked with the sequence or fragment, in which case the first amino acid at the N-terminus of the recombinant protein will always be a methionine, which is encoded by the ATG start codon. If desired, methionine at the N-terminus can be cleaved from the protein by in vitro incubation with cyanogen bromide.

Intracellularly expressed fusion proteins provide an alternative to direct expression of a sequence. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of a sequence and expressed in yeast. The DNA sequence at the junction of the two amino acid sequences may or may not encode a clearable site. See, e.g., EP Patent Pub. No. 196 056. Alternatively, the polypeptides can also be secreted from the cell into the growth media by creating a fusion protein comprised of a leader sequence fragment that provides for secretion in yeast or bacteria of the polypeptides. Preferably, there are processing sites encoded between the leader fragment and the sequence that can be cleaved either in vivo or in vitro. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (EP Patent Pub. No. 12 873) and the A-factor gene (U.S. Pat. No. 4,588,684). Alternatively, leaders of non-yeast origin, such as an interferon leader, can be used to provide for secretion in yeast (EP Patent Pub. No. 60057). Transcription termination sequences recognized by yeast are regulatory regions located 3' to the translation stop codon. Together with the promoter they flank the desired heterologous coding sequence. These flanking sequences direct the transcription of an mRNA which can be translated into the polypeptide encoded by the DNA.

Typically, the above described components, comprising a promoter, leader (if desired), coding sequence of interest, and transcription termination sequence, are put together in plasmids capable of stable maintenance in a host, such as yeast or bacteria. The plasmid can have two replication systems, so it can be maintained as a shuttle vector, for example, in yeast for expression and in a procaryotic host for cloning and amplification. Examples of such yeast-bacteria shuttle vectors include YEp24 (see Botstein, *Gene* 8:17–24 (1979)), pCl/1 (see Brake, *Proc. Natl. Acad. Sci. USA* 81:4642–4646(1984)), and YRp17 (see Stinchcomb, *J. Mol. Biol.* 158:157(1982)). In addition, the plasmid can be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect on the host of the vector and the polypeptides. See, e.g., Brake, et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. See Orr-Weaver, *Methods In Enzymol.* 101:228–245(1983) and Rine, *Proc. Natl. Acad. Sci. USA* 80:6750(1983).

Typically, extrachromosomal and integrating expression vectors can contain selectable markers to allow for the selection of yeast strains that have been transformed. Selectable markers can include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker can also provide yeast with the ability to grow in the presence of toxic compounds, such as metal. For example, the presence of CUP1 allows yeast to grow in the presence of copper ions. See Butt, *Microbiol. Rev.* 51:351(1987).

Alternatively, some of the above described components can be put together into transformation vectors. Transformation vectors are typically comprised of a selectable marker that is either maintained in a replicon or developed into an integrating vector, as described above. Expression and transformation vectors, either extrachromosomal or integrating, have been developed for transformation into many yeasts. Exemplary yeasts cell lines are *Candida albicans* (Kurtz, *Mol. Cell. Biol.* 6:142(1986), *Candida maltosa* (Kunze, *J. Basic Microbiol.* 25:141(1985), *Hansenula polymorpha* (Gletson, *J. Gen. Microbiol.* 132:3459(1986) and Roggenkamp, *Mol. Gen. Genet.* 202:302(1986), *Kluyveromyces frailis* (Das, *J. Bacteriol.* 158:1165(1984), *Kluyveromyces lactis* (De Louvencourt, *J. Bacteriol.* 154:737(1983) and Van den Berg, *Bio/Technology* 8:135(1990), *Pichia*

*guillerimondii* (Kunze, *J. Basic Microbiol.* 25:141(1985), *Pichia pastoris* (Cregg, *Mol. Cell. Biol.* 5:3376 (1985), *Saccharomyces cerevisiae* (Hinnen, *Proc. Natl. Acad. Sci. USA* 75:1929(1978) and Ito, *J. Bacteriol.* 153:163(1983), *Schizosaccharomyces pombe* (Beach and Nurse, *Nature* 300:706(1981), and *Yarrowia lipolytica* (Davidow, *Curr. Genet.* 10:380471(1985) and Gaillardin, *Curr. Genet.* 10:49 (1985).

Methods of introducing exogenous DNA into yeast hosts are well-known in the art, and typically include either the transformation of spheroplasts or of intact yeast cells treated with alkali cations. Transformation procedures usually vary with the yeast species to be transformed. See the publications listed in the foregoing paragraph for appropriate transformation techniques.

Additionally, the gene or fragment thereof can be expressed in a bacterial system. In such system, a bacterial promoter is any DNA sequence capable of binding bacterial RNA polymerase and initiating the downstream (3') transcription of a coding sequence (e.g. a desired heterologous gene) into mRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*). See Raibaud, *Ann. Rev. Genet.* 18:173(1984). Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (see Chang, *Nature* 198:1056(1977), and maltose. Additional examples include promoter sequences derived from biosynthetic enzymes such as tryptophan (trp) (see Goeddel, *Nuc. Acids Res.* 8:4057(1981), Yelverton, *Nuc. Acids Res.* 9:731(1981), U.S. Pat. No. 4,738,921 and EP Patent Pub. Nos. 36 776 and 121 775). The lactomase (bla) promoter system (see Weissmann, *Interferon* 3 (ed. I. Gresser), the bacteriophage lambda PL promoter system (see Shimatake, *Nature* 292:128(128) and the T5 promoter system (U.S. Pat. No. 4,689,406) also provides useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter such as the tac promoter (see U.S. Pat. No. 4,551,433, Amann, *Gene* 25:167 (1983) and de Boer, *Proc. Natl. Acad. Sci.* 80:21(1983)). A bacterial promoter can include naturally occurring promoters of non-bacterial origin that have the ability to bind bacterial RNA polymerase and initiate transcription. A naturally occurring promoter of non-bacterial origin can be coupled with a compatible RNA polymerase to produce high levels of expression of some genes in prokaryotes. The bacteriophage T7 RNA polymerase/promoter system is exemplary. (see Studier, *J. Mol. Biol.* 189:113(1986) and Tabor, *Proc. Natl. Acad. Sci.* 82:1074(1985)).

In addition to a functioning promoter sequence, an efficient ribosome binding site is also useful for the expression of the DNA sequence or fragment thereof in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon (see Shine, *Nature* 254:34(1975). The SD sequence is thought to promote binding of MRNA to the ribosome by the pairing of bases between the SD sequence and the 3' and of *E. coli* 16S rRNA (see Steitz, *Biological Regulation and Development: Gene Expression* (ed. R. F. Goldberger)(1979)).

The novel Toledo or Towne proteins of the invention can be expressed intracellularly. A promoter sequence can be directly linked with a novel Toledo or Towne DNA sequence, analog or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase. See EP Patent Pub. No. 219 237.

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of an sequence fragment thereof and expressed in bacteria. The resulting fusion protein preferably retains a site for a processing enzyme (factor Xa) to cleave the bacteriophage protein from the sequence or fragment thereof (see Nagai, *Nature* 309:810(1984). Fusion proteins can also be made with sequences from the lacZ gene (Jia, *Gene* 60:197 (1987),the trpE gene (Allen, *J. Biotechnol.* 5:93(1987) and Makoff, *J. Gen. Microbiol.* 135:11(1989), and the Chey gene (EP Patent Pub. No. 324 647) genes. The DNA sequence at the junction of the two amino acid sequences may or may not encode a clearable site. Another example is a ubiquitin fusion protein. Such a fusion protein is made with the ubiquitin region that preferably retains a site for a processing enzyme (e.g., ubiquitin specific processing-protease) to cleave the ubiquitin from the polypeptide. Through this method, mature Towne or Toledo polypeptides can be isolated. See Miller, *Bio/Technology* 7:698(1989).

Alternatively, proteins or polypeptides can also be secreted from the cell by creating chimeric DNA molecules that encode a fusion protein comprised of a signal peptide sequence fragment that provides for secretion of the proteins or polypeptides in bacteria. (See, for example, U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the protein or polypeptide.

DNA encoding suitable signal sequences can be derived from genes for secreted bacterial proteins, such as the E. coli outer membrane protein gene (ompA) (Masui, Experimental Manipulation of Gene Expression (1983) and Ghrayeb, EMBO J. 3:2437(1984)) and the E. coli alkaline phosphatase signal sequence (phoA) (see Oka, Proc. Natl. Acad. Sci. 82:7212(1985). The signal sequence of the alpha-amylase gene from various Bacilus strains can be used to secrete heterologous proteins from B. subtilis (see Palva, Proc. Natl. Acad. Sci. 79:5582(1982) and EP Patent Pub. No. 244 042).

Transcription termination sequences recognized by bacteria are regulatory regions located 3' to the translation stop codon. Together with the promoter they flank the coding sequence. These sequences direct the transcription of an mRNA which can be translated into the Towne or Toledo protein or polypeptide encoded by the DNA sequence. Transcription termination sequences frequently include DNA sequences of about 50 nucleotides capable of forming stem loop structures that aid in terminating transcription. Examples include transcription termination sequences derived from genes with strong promoters, such as the trp gene in E. coli as well as other biosynthetic genes.

Typically, the promoter, signal sequence (if desired), coding sequence of interest, and transcription termination sequence are maintained in an extrachromosomal element (e.g., a plasmid) capable of stable maintenance in the bacterial host. The plasmid will have a replication system, thus allowing it to be maintained in the bacterial host either for expression or for cloning and amplification. In addition, the plasmid can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. See e.g., EP Patent Pub. No. 127 328.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline (see Davies, Ann. Rev. Microbiol. 32:469(1978). Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in an extrachromosal vector or an integrating vector, as described above.

Expression and transformation vectors, either extra-chromosomal or integrating, have been developed for transformation into many bacteria. Exemplary are the expression vectors disclosed in Palva, Proc. Natl. Acad. Sci. 79:5582 (1982), EP Patent Pub. Nos. 036 259 and 063 953 and PCT Patent Publication WO 84/04541 (for B.subtilis); in Shimatake, Nature 292:128(1981), Amann, Gene 40:183 (1985), Studier, J. Mol. Biol. 189:113(1986) and EP Patent Pub. Nos. 036 776, 136 829 and 136 907 (for E. coli); in Powell, Appl. Environ. Microbiol. 54:655(1988) and U.S. Pat. No. 4,745,056 (for Streptococcus).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Exemplary methodologies can be found in Masson, FEMS Microbiol. Let. 60:273(1989), Palva, Proc. Natl. Acad. Sci. 79:5582(1982), EP Patent Pub. Nos. 036 259 and 063 953 and PCT Patent Pub. WO 84/04541 for Bacillus transformation. For campylobacter transformation, see e.g., Miller, Proc. Natl. Acad. Sci. 85:856(1988) and Wang, J. Bacteriol. 172:949(1990). For E. coli, see e.g., Cohen, Proc. Natl. Acad. Sci. 69:2110(1973), Dower, Nuc. Acids Res. 16:6127 (1988), Kushner, Genetic Engineering: Proceedings of the International Symposium on Genetic Engineering (eds. H. W. Boyer and S. Nicosia), Mandel, J. Mol. Biol. 53:159 (1970) and Taketo, Biochem. Biophys. Acta 949:318(1988). For Lactobacillus and Pseudomonas, see e.g., Chassy, FEMS Microbiol. Let. 44:173(1987) and Fiedler, Anal. Biochem. 170:38(1988), respectively. For Streptococcus, see e.g., Augustin, FEMS Microbiol. Let. 66:203(1990), Barany, J. Bacteriol. 144:698(1980), Harlander, Streptococcal Genetics (ed. J. Ferretti and R. Curtiss III)(1987), Perry, Infec. Immun. 32:1295(1981), Powell, Appl. Environ. Microbiol, 54:655(1988) and Somkuti, Proc. 4th Evr. Cons. Biotechnology 1:412(1987).

The present invention is illustrated by the following examples.

MATERIALS AND METHODS

A. Cells and Virus

Human CMV strains AD169, Towne and Toledo were obtained from E. S. Mocarski (Stanford University) and were used for all experiments. Two of these strains are also available through the ATCC, Accession Nos. VR-538 (AD169) and VR-977 (Towne). Virus was grown in cultures of human foreskin fibroblast (HF) cells with Dulbecco's modified Eagle's medium (DME) (JRH Biosciences, Lenexa, KS) as previously described in Spaete and Mocarski, J. Virol 56:135–43(1985), but supplemented with 10% fetal calf serum (FCS) (JRH Biosciences, Lenexa, Kans.), L-glutamine (2 mM), penicillin (100 units/ml), streptomycin (0.1 mg/ml) and pyruvate (1 mM). To prepare AD169, Towne and Toledo strain CMV DNAs by centrifugation to equilibrium on NaI gradients as previously described in Spaete and Mocarski, J. Virol 54:817–24(1985), roller bottles were infected with the CMV strains at a multiplicity of infection (MOI) of 0.001 plaque forming units (pfu)/cell to minimize the production of defective virus particles. The infected cells were refed at four days post infection with medium. At eight days post infection when the monolayer was well infected, cells were scraped into a 50 ml conical tube in 10 mls media per roller bottle and pelleted at 1000 revolutions per minute (rpm) for 10 minutes. Pellets were resuspended in 2.0 ml 0.01M Tris and 0.01 EDTA (TE) (pH 7.4) with 1% NP40, 1% deoxycholate and incubated on ice until all cellular nuclei were lysed when viewed under a microscope. Lysates were transferred to a 2059 tube (Falcon) and spun at 2600 rpm for 5 minutes at 4° C. Supernatants were transferred to another 2059 tube and RNAse (Worthington-DNase free) was added at 50 μg/ml followed immediately by Proteinase K (200 μmg/ml) and 1% sodium dodecyl sulfate (SDS). Supernatants were incubated in a 65° C. water bath for 60 minutes, brought to 16 ml with TE, pH 7.4, added to 24 mls of saturated NaI and 0.15 ml ethidium bromide (5 mg/ml). Samples were centrifuged to equilibrium at 55,000 rpm at 20° C. for 24 hours in a Beckman Ti70 rotor. Fractions containing the viral DNA were extracted with butanol equilibrated with TE with gentle rocking followed by centrifugation at 3,000 rpm for 10 min at 20° C. and further extracted 2 to 3 times with butanol to reduce volume. Samples were extracted with an equal volume of isoamyl alcohol equilibrated with TE, spun and re-extracted. DNA was dialyzed against three changes of TE with 1% phenol and 1M NaCl. The $OD_{260}$ and $OD_{280}$ were read to determine purity of the AD169, Toledo and Towne DNA.

Clinical isolates were obtained from M. Fiala (Rancho Mirage, Calif.), and S. Chou (Oregon Health Sciences University). Rapid isolation of HCMV infected cell viral DNA was carried out as previously described in Spaete and Frenkel, *Cell* 30:295–304(1982), except that DNA was not radiolabeled before purification. Briefly, infected cell monolayers (25 cm² flasks) were rinsed twice with phosphate-buffered saline (PBS) and lysed in a 1.0 ml solution of 0.1M NaCl, TE, pH 8.0, 0.05% SDS and 0.1 mg/ml Proteinase K. Lysates were incubated 2–24 hours at 37° C., extracted twice with 1 volume of phenol, 1 volume of chloroform followed by centrifugation at 2500 rpm for 5 minutes to separate phases. The aqueous phase was extracted twice with 1 volume of ether and the DNA was precipitated with 0.1 volume 3M NaAC and two volumes of ethanol or isopropanol. DNA was chilled, collected by centrifugation or spooled on a glass rod, dried and resuspended in TE.

B. Plasmid DNA

Plasmids pXbaI E, pXbaI T and pXbaI Q (Thomsen and Stinski, 1981), representing Towne strain map units 0.69 to 0.8, were obtained from M. Stinski (University of Iowa).

Clone 65 was derived by cloning a gel extracted BamHI digested Toledo DNA fragment into the BamHI site of plasmid, pGEM®-3Zf+ (Promega, Madison, Wis.). Briefly, five μg of Toledo DNA was digested with 40 units of BamHI and electrophoresed in a preparative 1% low-melting-point agarose gel for 490 volt hours in 1× TAE buffer. Toledo DNA migrating at ca. 5 kilobase pairs (kbp) was excised and the agarose was digested with 2 units of β-agarase I (New England BioLabs, Beverly, Mass.). This DNA fragment was precipitated with 2 volumes of isopropanol, chilled to −20° C., spun in an Eppendorf centrifuge for 15 minutes, dried and resuspended in 50 μl TE. The gel extracted fragment was ligated to BamHI digested pGEM®-3Zf+ using T4 DNA ligase (New England BioLabs, Berverly, Mass.), and an aliquot of the ligation mixture was used to transform competent *Escherichia coli* XL-1, Blues (Stratagene, La Jolla, Calif.) by the calcium shock method (Mandel and Higa, 1970), or by electroporation using methods as written in the Pulse Controller Guide published by BioRad (Richmond, Calif.).

Cosmid 1 is a ca. 53 kbp partially digested HindIII fragment of Toledo DNA spanning 0.69 to 0.87 map units cloned into cosmid pHC79 (Hohn and Collins, 1980) obtained from E. S. Mocarski (Stanford University). Subcloned from cosmid 1 were the following:

Clones 4 and C1300 were derived by cloning BamH1 digested fragments from Cosmid 1 cloned into a Bluescript M13+ plasmid vector. As such, these clones represent Toledo DNA sequence spanning portions of Cosmid 1.

Clone C23K was derived as a complete BanH1 digested fragment of Cosmid 1 DNA and circularized by ligation.

C. Preparation of Radioactively Labeled Probes and Hybridization.

Plasmid or viral DNA was radioactively labeled in vitro by nick translation (Rigby et al., 1977) with a kit (Boehringer Mannheim), and using [α³²P]dCTP (Amersham Corp.). Hybridizations to immobilized CMV DNA were performed essentially as described by Spaete and Mocarski, *J. Virol* 54:817–24 (1985), but at 68° C. in a solution of 6× SSC (1× SSC is 0.15M NaCl plus 0.015M sodium citrate), 0.2% polyvinylpyrrolidone, 0.2% Ficoll, 0.2% bovine serum albumin, and 0.1% sodium dodecyl sulfate, with the amount of salmon sperm DNA being changed from 25 μg/ml to 100 μg/ml and 30% formamide being reduced to 15%.

DNA was transferred to Hybond-N+ nylon transfer membranes (Amershan Corp.), after restriction enzyme digestion and electrophoresis in 1% agarose gels by standard techniques (Maniatis et al., 1982). DNA was cross-linked to the membrane with 120,000 microjoules/cm² of UV irradiation using a UV Crosslinker 1000 (Hoefer Scientific Instruments, San Francisco, Calif.). Membranes were prehybridized 1 hour at 68° C. in solution A (6× SSC, 0.2% polyvinylpyrrolidone, 0.2% Ficoll, 0.2% bovine serum albumin, 0.1% sodium dodecyl sulfate, 100 μg/ml salmon sperm DNA and 15% formamide), then nick-translated [α³²P]-labeled probe in a solution containing 100 μg/ml salmon sperm DNA was denatured by boiling for five minutes, snap-cooled on ice, added to the membrane and allowed to hybridize overnight at 68° C. After hybridization, unannealed probe was removed by rinsing the membrane 3× with 2× SSC followed by reincubation in solution A lacking salmon sperm DNA at 68° C. for 15 minutes. The washing procedure was repeated, the blot was rinsed in a large volume of 2× SSC at room temperature, the membrane was air dried and autoradiographed using Kodak X-AR film.

D. Nucleotide Sequence Determination and Analysis.

All nucleic acid sequences were determined by the dideoxynucleotide chain termination method (Sanger et al., 1977). A variety of templates were prepared for sequencing; they included single-stranded phage DNA, double-stranded plasmid and cosmid DNA, viral genomic DNA, and PCR products. Manual and automated sequencing (with an ABI 373A instrument) were employed. Both one-cycle and multi-cycle sequencing protocols were used. The sequence was determined for both strands. Ambiguous regions were corrected by additional sequencing after proofreading. The primers used for sequencing were synthesized on an ABI 392 instrument (Applied Biosystems). The contig and analysis of the sequence were performed using MacDNASIS (Hitachi). The homology searches were performed using the BLAST program through NCBI services.

EXAMPLE 1

Identification of Novel Sequences in the Genomes of CMV Towne and Toledo Strain Isolates.

To determine the cross representation of DNA sequences in the Towne and Toledo strains of CMV, viral DNA from each strain was digested to completion with XbaI, ClaI, BamHI, BglII, EcoRI, and HindIII. After electrophoresis through a 1% agarose gel, the CMV DNAs were denatured in 0.2M NaCl/0.6M NaOH, neutralized in 0.6M NaCl/1M Tris, pH 7.5, in situ, and the gel was soaked in 20× SSC for 30 minutes. Stereo blots were prepared by placing identically sized Hybond-N+ nylon membranes (Amersham Corp.), on either side of the gel and transferring the DNAs to the membranes in both directions using the capillary action of paper towels. After blotting overnight in 20× SSC, the membranes were washed in 2× SSC and the DNA was immobilized on the membrane by UV irradiation as described above.

DNA probes of Towne and Toledo DNA with an average size of 500 bp were prepared by sonicating 10 μg of each DNA in a 2063 tube (Falcon Plastics) using 4 pulses of 10 seconds each at a setting of 3 on a Heat Systems, Inc. sonicator (Farmingdale, N.Y.). Following sonication, the viral DNAs were digested with the restriction enzymes AvaI, BanI and BfaI, to further reduce the size complexity of the probe DNA. These enzymes were chosen because a search of the AD169 DNA database sequences (EMBL accession number X17403), revealed abundant cut sites (326, 386, and 341, respectively); their restriction enzyme digestion buffers are compatible; and their sites do not overlap. Ethidium bromide stained gels of the sheared viral DNAs prepared in this manner revealed a range of DNA sizes from 1300 bp to less than 100 bp, with the majority of DNA migrating at approximately 300 bp as judged by comigration with a HaeIII digested ØX174 DNA standard marker (New England BioLabs, Beverly, Mass.). The Towne and Toledo sheared probe DNA was then nick translated using $[\alpha^{32}P]$ dCTP (Amersham Corp.) as described above and each probe was applied to stereo blots of immobilized, restriction enzyme digested, Towne and Toledo DNAs. After hybridization and autoradiography, the hybridization patterns were analyzed to determine the fragments on each DNA profile which did not hybridize with the heterologous strain probe but did hybridize with the homologous strain probe. For example, the loss of a signal for a prominent 5 kbp band on the BamHI digest of Toledo DNA when using the Towne probe, which was present when the Toledo DNA was used to probe itself, revealed a region of sequence divergence between the two isolates (see FIG. 3).

This 5 kbp fragment was cloned by gel extraction as described above and designated clone 65. The clone 65 Toledo DNA was sequenced in its entirety and compared to Towne DNA sequence generated from the pXbaI T clone which was shown to be divergent from AD169 DNA sequences (see Example 2 below). The full sequence of clone 65 is shown in FIG. 1. In FIG. 1, Clone 65 begins with nucleotide 4664 and ends with nucleotide 9327. Surprisingly, the DNA from the pXbaI T clone of Towne DNA (1,856 bp) and clone 65 of Toledo DNA (4,668 bp) shared 104 bp of sequence identity. This small stretch of sequence homology allowed mapping of the region of Toledo DNA divergence to the boundary of the Unique Long ($U_1$) component and the inverted repeats (alternatively termed IRL or b' sequences) on the AD169 and Towne DNA maps. These newly isolated Toledo strain nucleotide sequences from clone 65 were not represented in the reference laboratory strain, AD169, which has been sequenced in its entirety by Chee and colleagues (EMBL accession number X17403).

EXAMPLE 2

Identification of Novel Sequences in the Genome of CMV Towne Not Found in Reference Strain AD169.

DNA sequence heterogeneity between the Towne strain and the AD169 strain has been found. See, Pritchett, *J. Virology* 36:152–61 (1980). However, although the gross structural organization of the CMV genome has been determined and strain to strain restriction site polymorphisms have been mapped for many strains, strain-to-strain differences on the nucleotide level have not been determined. The laboratory strain AD169 was the first CMV isolate to be sequenced and has served as the reference strain in defining the genetic complexity of the CMV genome.

In order to examine nucleotide sequence differences between Towne and AD169, we focused on the region shown to be divergent in the Toledo strain, i.e. the boundary between the $U_L$ component and the b' sequences, as explained in detail in Example 1. Plasmid pXbaI T was labeled using the NEBlot™ Phototope™ Detection Kit (New England Biolabs, Beverly, Mass.), and used as a probe on blots of immobilized restriction enzyme digested Towne, Toledo and AD169 DNAs. Briefly, pXbaI T was linearized with PvuII, ethanol precipitated and resuspended in 34 µl of nuclease free water. The plasmid was denatured in boiling water for five minutes, snap cooled on ice for five minutes and centrifuged briefly at 4° C. The following reagents were added to the tube in the order listed: 10 µl of 5× labeling mix, 5 µl of dNTP mix, 1 µl of DNA polymerase I (Klenow fragment). The mix was incubated at 37° C. for 6 hours and the reaction was terminated by adding 5 µl of 0.2M EDTA, pH. 8.0. The probe was precipitated by adding 5 µl of 4M LiCl and 150 µl of ethanol, chilling to −80° C. for 30 minutes, pelleted in an Eppendorf centrifuge, washed with 70% ethanol and resuspended in 20 µl of Resuspension Buffer as supplied by the kit. The hybridization reaction was essentially as described above except that after hybridization the membrane was washed twice in 2× SSC, 0.1% SDS at room temperature for 5 minutes each followed by two washes in 0.1× SSC, 0.1% SDS at 68° C. for 15 minutes. The detection reactions link the biotinylated probes to alkaline phosphatase through a strepavidin bridge and the hybridized probe was visualized by cleavage of the Lurnigen-PPD substrate. The blocking steps, strepavidin incubation, alkaline phosphatase incubation and Lumigen-PPD reaction were carried out as described in the kit manual. Exposure of the blots to Kodak XAR film revealed that, as expected, (i) an XbaI digested fragment of sized 1.85 kbp (XbaI T) was hybridized on Towne DNA probed with pXbaI T and (ii) a comigrating XbaI digested fragment was present in Toledo DNA. The AD169 DNA failed to show any hybridization signal on any of the restriction enzyme digestion patterns. Nucleotide sequence of pXbaI T confirmed the total lack of identity of the Towne DNA and AD169 DNA. Nucleotide sequencing of cosmid 1 DNA (see B. Plasmid DNA in Material and Methods, above) from Toledo revealed extensive sequence identity between the newly identified Towne DNA and the Toledo DNA of cosmid 1 in this region. Surprisingly, the orientation of the sequence was reversed in Toledo relative to Towne.

EXAMPLE 3

Identification of Novel Toledo DNA Sequences in the Genomes of Recent Clinical Isolates and not Found in Reference Strain AD169.

To determine the penetrance of sequences represented by clone 65 in recent clinical isolates, five representative clinical isolates (HCMVF, C128, C354, C793 and C980) were digested with restriction enzymes BamHI and XbaI along with the Toledo, Towne and AD169 DNAs prepared as described in the Materials and Methods section above, electrophoresed through agarose, transferred to a Hybond-N+ nylon transfer membrane, and probed with nick-translated $[\alpha^{32}P]$-labeled clone 65 according to the procedures outlined in the Materials and Methods section. As can be seen in FIG. 4, the autoradiographs revealed that homology was detected in all of the clinical isolates. In FIG. 4, a band at ca. 5 kbp is visible in lane 1 (the Toledo DNA), appears in Towne DNA (lane 2), is missing from lane 3 (the AD169 DNA), and visible in lanes 4 through 8 (the clinical isolates HCMVF, C128, C354, C793 and C980). These results demonstrate that the newly isolated sequence found in the Toledo strain of HCMV is also present in the recent clinical isolates but is not present in the AD169 reference strain. Nucleotide sequence analysis reveals the reason for the weak hybridization signal to the Towne DNA fragment is due to the existence of only 151 nucleotides of sequence identity with Towne DNA. The shared 104 bp sequence identity in Example 1 is responsible for a weak hybridization signal to XbaI "T" sized fragments from both Towne and Toledo DNAs seen in the XbaI digests (lanes 9 and 10). The XbaI digest of the clinical isolates (lanes 12 through 16) also reveals hybridization to multiple high molecular weight bands. Analysis of these and other clinical isolate genomes with other probes in the region has revealed that the shared sequences may be in inverted orientation in some isolates relative to the orientation in the Toledo strain.

FIG. 6 is a schematic illustration of the relative positions of novel sequences identified in Toledo genomic DNA, Towne genomic DNA in a comparison with AD169 strain genomic DNA. The dashed lines delimit the region of the genome where homologous and divergent sequences are found. The top line illustrates a Toledo DNA restriction map showing BamHII (indicated by "B") and XbaI (indicated by "X") restriction enzyme sites extending between the homology breakpoints identified by inverted triangles at nucleotides 175068 and 188843 (numbered with reference to the AD169 DNA sequence—EMBL accession number X17403). Subclones 4, 1300, C23K and 65 of the Toledo DNA sequence are shown in boxes above the map. An inverted region of homology with respect to Towne is shown by the inverted triangles between nucleotides 178221 and 175082. Unique sequences are shown by a thin line, and inverted repeat sequences denoted by thick lines, b'a'c'. The end of the c' repeats is shown with an arrow at nucleotide 191412. The middle line illustrates a Towne DNA restriction map showing BamHI (B) and XbaI (X) restriction enzyme sites as described above for Toledo and showing XbaI clones E, T. and Q in boxes below. Shaded area refers to homologous regions shared with Toledo DNA but inverted in orientation. Nucleotide numbers shown are with reference to the AD169 DNA sequence. Undetermined extent of b' repeat sequences in the Towne strain is shown by thin lines at AD169 strain nucleotide reference 180034. The bottom line illustrates the AD169 genome displayed in the prototype orientation. Unique sequences are displayed by a thin line, and inverted repeats of the long ($U_L$) and short ($U_S$) components are denoted by boxes, ab-b'a', and a'c'-ca. The a sequence, is a terminal direct repeat with an inverted copy (a'), at the junction of the long and short components. The length of the AD169 DNA sequence is indicated as 229354 nucleotides and the map position of the internal repeats are shown with the nucleotide reference numbers and arrows.

EXAMPLE 4

Open Reading Frame Analysis of the Novel Toledo and Towne DNA Sequences

The novel Toledo and Towne sequences encoded potential open reading frames (ORFs). Using an arbitrarily chosen parameter of 10 kiloDaltons as the minimum calculated protein molecular weight, a total of 36 ORFs were identified in the novel Toledo sequence and a total of 4 ORFs were identified in the novel Towne sequence. The putative amino acid sequences of these ORFs are set forth in the sequence listing (SEQ ID NOS:2, 3, 4, 5, 7, 8, 9, 10, 11, 12, 13, 14, 15, 16, 17, 18, 19, 20, 21, 22, 23, 24, 25, 26, and 27). FIG. 5 shows the schematic presentation of these ORFs in the novel Toledo and Towne DNA sequences, together with previously reported AD169 ORFs of the corresponding region. Names were assigned for these ORFs starting from UL133 as the first ORF at the left side of the UL in Toledo sequence. The first ORF in the novel Towne sequence was assigned as UL147, which was determined to be present in the novel Toledo sequence disclosed here. UL130 and UL132 in AD169 were determined to be present in the novel Toledo sequence. Additionally, UL153 and UL154 exhibited regions of homology to IRL14 and IRL12, respectively. All ORFs were searched for homologous sequence in the non-redundant databases of NCBI using the BLASTP program. Among all ORFs searched, only UL132 identified a homologue in the database, which was HCMV mtrIII (GenBank Accession No. X75606), exhibiting 76% identity at the amino acid level. The solid circle identified the ORFs that contained the potential N-linked glycosylation site sequence, N-X(-P)-S/T. These potential glycoproteins may be biologically significant as antigenic or immunogenic molecules.

The present investigation is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. An isolated DNA sequence comprising the nucleotide sequence of SEQ ID NO:1, which encodes at least a part of a human cytomegalovirus.

2. An RNA molecule transcribed from said DNA sequence of claim 1.

3. A vector comprising said DNA sequence of claim 1.

4. A host cell transformed with said DNA sequence of claim 1, in operative association with an expression control sequence capable of directing replication and expression of said DNA sequence.

5. A method of producing a human cytomegalovirus protein comprising culturing said host cell of claim 4 in a suitable culture medium and isolating said protein from said medium.

* * * * *